United States Patent
Harashima et al.

(10) Patent No.: US 11,517,528 B2
(45) Date of Patent: Dec. 6, 2022

(54) LIPID MEMBRANE STRUCTURE FOR DELIVERY INTO SIRNA CELL

(71) Applicant: NATIONAL UNIVERSITY CORPORATION HOKKAIDO UNIVERSITY, Sapporo (JP)

(72) Inventors: Hideyoshi Harashima, Sapporo (JP); Yusuke Sato, Sapporo (JP)

(73) Assignee: NATIONAL UNIVERSITY CORPORATION HOKKAIDO UNIVERSITY, Sapporo (JP)

(*) Notice: Subject to any disclaimer, the term of this patent is extended or adjusted under 35 U.S.C. 154(b) by 221 days.

(21) Appl. No.: 16/622,109

(22) PCT Filed: Jun. 15, 2018

(86) PCT No.: PCT/JP2018/022940
§ 371 (c)(1),
(2) Date: Dec. 12, 2019

(87) PCT Pub. No.: WO2018/230710
PCT Pub. Date: Dec. 20, 2018

(65) Prior Publication Data
US 2020/0129431 A1 Apr. 30, 2020

(30) Foreign Application Priority Data
Jun. 15, 2017 (JP) .............................. JP2017-117708

(51) Int. Cl.
| A61K 31/713 | (2006.01) |
| C07D 211/32 | (2006.01) |
| A61K 9/127 | (2006.01) |
| C07D 295/03 | (2006.01) |

(52) U.S. Cl.
CPC ............ *A61K 9/127* (2013.01); *A61K 31/713* (2013.01); *C07D 211/32* (2013.01); *C07D 295/03* (2013.01)

(58) Field of Classification Search
None
See application file for complete search history.

(56) References Cited

U.S. PATENT DOCUMENTS

| 10,182,987 B2 * | 1/2019 | Harashima ............ C07C 215/08 |
| 2009/0305409 A1 | 12/2009 | Kogure et al. |
| 2012/0172411 A1 | 7/2012 | Heyes et al. |
| 2013/0122054 A1 | 5/2013 | Harashima et al. |
| 2017/0273905 A1 | 9/2017 | Harashima et al. |

FOREIGN PATENT DOCUMENTS

| CN | 103167866 A | 6/2013 |
| EP | 1676588 A1 | 7/2006 |
| EP | 3147277 A1 | 3/2017 |
| EP | 3275448 A1 | 1/2018 |
| JP | 2006-028030 A | 2/2006 |
| JP | 2014-500233 A | 1/2014 |
| JP | 2016-084297 A | 5/2016 |
| WO | WO 2005/032593 A1 | 4/2005 |
| WO | WO 2006/101201 A1 | 9/2006 |
| WO | WO 2007/102481 A1 | 9/2007 |
| WO | WO 2011/132713 A1 | 10/2011 |
| WO | WO 2012/040184 A2 | 3/2012 |
| WO | WO 2015/178343 A1 | 11/2015 |
| WO | WO-2015178343 | * 11/2015 ........... A61K 9/1272 |
| WO | WO-2015178343 A1 | * 11/2015 ........... A61K 9/1272 |
| WO | 2016/153012 | 9/2016 |

OTHER PUBLICATIONS

International Search Report dated Sep. 11, 2018, in connection with International Application No. PCT/JP2018/022940.
Akita et al., Nanoparticles for ex vivo siRNA delivery to dendritic cells for cancer vaccines: programmed endosomal escape and dissociation. J Control Release. May 10, 2010;143(3):311-7. doi:10.1016/j.jconrel.2010.01.012. Epub Jan. 15, 2010.
Akita et al., Development of multifunctional envelope-type nano-device (MEND) based on the regulation of intracellular trafficking. Drug Delivery System. 2007;22-2:115-22.
Belliveau et al., Microfluidic Synthesis of Highly Potent Limit-size Lipid Nanoparticles for In Vivo Delivery of siRNA. Mol Ther Nucleic Acids. Aug. 14, 2012;1:e37. doi: 10.1038/mtna.2012.28.
Cabral et al., Accumulation of sub-100 nm polymeric micelles in poorly permeable tumours depends on size. Nat Nanotechnol. Oct. 23, 2011;6(12):815-23. doi: 10.1038/nnano.2011.166.
Chen et al., Influence of particle size on the in vivo potency of lipid nanoparticle formulations of siRNA. J Control Release. Aug. 10, 2016;235:236-244. doi: 10.1016/j.jconrel.2016.05.059. Epub May 26, 2016.
Dong et al., Lipopeptide nanoparticles for potent and selective siRNA delivery in rodents and nonhuman primates. Proc Natl Acad Sci U S A. Mar. 18, 2014;111(11):3955-60. doi: 10.1073/pnas.1322937111. Epub Feb. 10, 2014. Erratum in: Proc Natl Acad Sci U S A. Apr. 15, 2014;111(15):5753.

(Continued)

*Primary Examiner* — Celeste A Roney
(74) *Attorney, Agent, or Firm* — Wolf, Greenfield & Sacks, P.C.

(57) ABSTRACT

A lipid membrane structure includes, as lipid components, a lipid compound represented by Formula (I):

$$(R^1)(R^2)C(OH)-(CH_3)_a-(O-CO)_b-X \qquad (I)$$

[in the formula, a represents an integer of 3 to 5; b represents an integer of 0 or 1; $R^1$ and $R^2$ each independently represents a linear hydrocarbon group that may have —CO—O—; and X represents a 5- to 7-membered non-aromatic heterocyclic group or a group represented by Formula (B) (in the formula, d represents an integer of 0 to 3, and $R^3$ and $R^4$ each independently represents a $C_{1-4}$ alkyl group or a $C_{2-4}$ alkenyl group, where, $R^3$ and $R^4$ may be bonded to each other to form a 5- to 7-membered non-aromatic heterocycle (where, one or two $C_{1-4}$ alkyl groups or $C_{2-4}$ alkenyl groups may be substituted on the ring)].

16 Claims, 17 Drawing Sheets

(56) References Cited

OTHER PUBLICATIONS

Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.

Jayaraman et al., Maximizing the potency of siRNA lipid nanoparticles for hepatic gene silencing in vivo. Angew Chem Int Ed Engl. Aug. 20, 2012;51(34):8529-33. doi: 10.1002/anie.201203263. Epub Jul. 10, 2012.

Kakudo et al., Transferrin-modifted liposomes equipped with a pH-sensitive fusogenic peptide: an artificial viral-like delivery system. Biochemistry. May 18, 2004;43(19):5618-28.

Kogure et al., Development of a non-viral multifunctional envelope-type nano device by a novel lipid film hydration method. J Control Release. Aug. 11, 2004;98(2):317-23.

Leung et al., Lipid Nanoparticles Containing siRNA Synthesized by Microfluidic Mixing Exhibit an Electron-Dense Nanostructured Core. J Phys Chem C Nanomater Interfaces. Aug. 30, 2012;116(34):18440-18450. Epub Jul. 18, 2012.

Maier et al., Biodegradable lipids enabling rapidly eliminated lipid nanoparticles for systemic delivery of RNAi therapeutics. Mol Ther. Aug. 2013;21(8):1570-8. doi: 10.1038/mt.2013.124. Epub Jun. 25, 2013.

Nakamura et al., Chemical Industry. Jul. 2016; 477-82.

Sato et al., Elucidation of the physicochemical properties and potency of siRNA-loaded small-sized lipid nanoparticles for siRNA delivery. J Control Release. May 10, 2016;229:48-57. doi: 10.1016/j.jconrel.2016.03.019. Epub Mar. 17, 2016.

Sato et al., Relationship Between the Physicochemical Properties of Lipid Nanoparticles and the Quality of siRNA Delivery to Liver Cells. Mol Ther. Apr. 2016;24(4):788-95. doi: 10.1038/mt.2015.222. Epub Dec. 18, 2015.

Sawant et al., Challenges in development of targeted liposomal therapeutics. Aaps J. Jun. 2012;14(2):303-15. doi: 10.1208/s12248-012-9330-0. Epub Mar. 14, 2012. Review.

Shen et al., Silencing of SOCS1 enhances antigen presentation by dendritic cells and antigenspecific anti-tumor immunity. Nat Biotechnol. Dec. 2004;22(12): 1546-53. Epub Nov. 21, 2004.

Song et al., A20 is an antigen presentation attenuator, and its inhibition overcomes regulatory T cell-mediated suppression. Nat Med. Mar. 2008;14(3):258-65. doi: 10.1038/nm1721. Epub Mar. 2, 2008.

Subbarao et al., pH-dependent bilayer destabilization by an amphipathic peptide. Biochemistry. Jun. 2, 1987;26(11):2964-72.

Warashina et al., A20 silencing by lipid envelope-type nanoparticles enhances the efficiency of lipopolysaccharide-activated dendritic cells. Biol PharmBull. 2011;34(8):1348-51.

Warashina et al., A lipid nanoparticle for the efficient delivery of siRNA to dendritic cells. J Control Release. Mar. 10, 2016;225:183-91. doi: 10.1016/j.jconrel.2016.01.042. Epub Jan. 26, 2016.

Watanabe et al., In vivo therapeutic potential of Dicer-hunting siRNAs targeting infectious hepatitis C virus. Sci Rep. Apr. 23, 2014;4:4750. doi: 10.1038/srep04750.

Wittrup et al., Visualizing lipid-formulated siRNA release from endosomes and target gene knockdown. Nat Biotechnol. Aug. 2015;33(8):870-6. doi: 10.1038/nbt.3298. Epub Jul. 20, 2015.

Wyman et al., Design, synthesis, and characterization of a cationic peptide that binds to nucleic acids and permeabilizes bilayers. Biochemistry. Mar. 11, 1997;36(10):3008-17.

Xu et al., Quantitation of physiological and biochemical barriers to siRNA liver delivery via lipid nanoparticle platform. Mol Pharm. May 5, 2014;11(5):1424-34. doi: 10.1021/mp400584h. Epub Apr. 1, 2014.

Yamamoto et al., Novel pH-sensitive multifunctional envelope-type nanodevice for siRNAbased treatments for chronic HBV infection. J Hepatol. Mar. 2016;64(3):547-55. doi: 10.1016/j.jhep.2015.10.014. Epub Oct. 24, 2015.

Chinese Office Action date Sep. 24, 2021 for Application No. 201880038874.2.

Nakamura et al., Small-sized, stable lipid nanoparticle for the efficient delivery of siRNA to human immune cell lines. Sci Rep. Nov. 28, 2016;6:37849. doi: 10.1038/srep37849. PMID: 27892533; PMCID: PMC5124971.

\* cited by examiner

LIPID MEMBRANE STRUCTURE FOR DELIVERY INTO SIRNA CELL

CROSS REFERENCE TO RELATED APPLICATIONS

This Application is a National Stage filing under 35 U.S.C. 371 of International Patent Application No. PCT/JP2018/022940, filed Jun. 15, 2018, which claims priority to Japan Application Number 2017-117708, filed Jun. 15, 2017. The entire contents of these applications are incorporated herein by reference in their entirety.

TECHNICAL FIELD

The present invention relates to a lipid membrane structure for delivery into cells such as a small interfering RNA (siRNA). More specifically, the present invention relates to a lipid membrane structure such as a liposome capable of easily delivering siRNA or the like into the nucleus of an immune cell, particularly into a dendritic cell.

Priority is claimed on Japanese Patent Application No. 2017-117708, filed Jun. 15, 2017, the content of which is incorporated herein by reference.

BACKGROUND ART

As a means for specifically transporting a drug to an affected area, a method of sealing a drug in a liposome that is a lipid membrane structure has been proposed. In particular, the efficacy of liposomes in which an antitumor agent is sealed has been widely reported in the field of malignant tumor treatment. In addition, as a lipid membrane structure that can be used for gene expression, a multifunctional envelope-type nano device (MEND, hereinafter may be abbreviated as "MEND" in the present specification, and for example, refer to Non-Patent Literature 1 and the like) has been proposed. This structure can be used as a drug delivery system for selectively delivering a gene or the like into a specific cell, and is known to be useful for, for example, tumor gene treatment.

As a means for delivering target substances such as drugs, nucleic acids, peptides, polypeptides, and sugars to specific sites such as target organs and tumor tissues using a lipid membrane structure, a number of methods of modifying a surface of a lipid membrane structure with a functional molecule have been proposed. A lipid membrane structure in which a drug such as an anti-tumor agent is enclosed is in a state where, when it reaches a target cell, it is taken into the cell by endocytosis to become enclosed in the endosome, and thereafter, it undergoes lysosomal enzymatic hydrolysis, and thereby a drug is released into the cytoplasm. A liposome (Non-Patent Literature 3) and a MEND (Patent Literature 4) in which a surface of a liposome is modified with a peptide (GALA: Non-Patent Literature 2) have been proposed in order to enhance drug release performance from the liposome incorporated into the endosome.

In addition, as a means for transferring a lipid membrane structure enclosing a target substance such as a nucleic acid into the nucleus of a target cell, for example, a liposome of which an outer surface is modified with octaarginine (Patent Literature 1 and Non-Patent Literature 4), a bilamellar liposome having a lipid membrane modified with a nuclear translocation peptide (Patent Literature 2), and a liposome of which a surface is modified with a monosaccharide such as galactose or mannose (Patent Literature 3) have been proposed. It has been reported that a multi-lipid membrane structure (T-MEND) modified with a monosaccharide showed fusion performance with a lipid membrane and a nuclear membrane, and was able to improve gene expression efficiency in in vitro test results. Furthermore, it has been reported that a lipid membrane structure modified with a KALA peptide (Non-Patent Literature 5) can efficiently deliver a substance such as a nucleic acid into the nucleus of a cell (Patent Literature 5).

Meanwhile, dendritic cells are antigen-presenting cells that play a central role in immune responses, and are therefore important target cells in cancer immunotherapy. Immune cell therapy (dendritic cell therapy) is also performed in which dendritic cells are collected from a cancer patient, in vitro antigen introduction and activation are performed, and then the cells are administered to the patient again. Immunosuppressive factors in dendritic cells have been discovered in recent years, and dendritic cells are also attracting attention as a target of siRNA drugs. By combining dendritic cell therapy with immunotherapy, more powerful cancer immunity induction is expected to be performed.

In the related art, regarding the introduction of an RNA into the nucleus of dendritic cells, there are reports (Non-Patent Literature 6 and Non-Patent Literature 7) that an immunosuppressive factor was knocked down using a lentiviral vector that expresses an shRNA. However, there are few reports of siRNA introduction into dendritic cells using artificial delivery systems. Although use of a viral vector can achieve highly efficient knockdown of a target gene, it has a safety problem.

R8/GALA-D-MEND (D-MEND) has been reported as an artificial delivery system for introducing siRNA (Non-Patent Literature 8). D-MEND is a nanocarrier in which the number of envelope membranes of MEND is controlled by modifying an octaarginine (R8) peptide that is a cytophilic element, and a GALA peptide that is an endosomal escape element to MEND. D-MEND shows about 70% knockdown at a low siRNA concentration of 12 nM in HeLa cells, which are commonly used cancer cells, and a level of its activity is double or more that of Lipofectamine 2000 (LFN2000), which is widely used as a general introduction reagent.

However, in a case where transfection of dendritic cells derived from mouse bone marrow cells is performed with D-MEND, an siRNA concentration needs to be set at a high concentration (80 to 120 nM) to achieve 70% to 80% knockdown efficiency, and there is also a problem of knockdown efficiency being only about 40% depending on siRNA target factors (Non-Patent Literature 9). In a case of using artificial delivery systems of the related art as described above, knockdown efficiency in dendritic cells tends to be greatly reduced compared to general cancer cells, and this hinders development of siRNA drugs in the field of immunotherapy.

So far, many cationic lipids have been developed in order to achieve efficient in vivo delivery of functional nucleic acids, particularly siRNA capable of inhibiting expression of a specific target gene. In particular, pH-sensitive cationic lipids, which are electrically neutral at physiological pH and change cationically in a weakly acidic pH environment, such as endosomes have been extensively developed. Jayaraman et al. developed DLin-MC3-DMA and achieved 0.005 mg siRNA/kg as $ED_{50}$ in factor 7 (F7) knockdown in the mouse liver (Non-Patent Literature 10). The inventors of the present invention have also developed unique pH-sensitive cationic lipids, namely YSK05 and YSK13-C3, and achieved 0.06 mg siRNA/kg and 0.015 mg siRNA/kg as $ED_{50}$ in F7 knockdown (Non-Patent Literature 11, Non-Patent Literature 12, and Non-Patent Literature 13). In addition, Maier et al. developed L319 obtained by imparting biodegradability to MC3-DMA, and reported on the compatibility of 0.01 mg siRNA/kg as $ED_{50}$ and high safety (Non-Patent Literature 14, Non-Patent Literature 15, and Non-Patent Literature 16). However, it has been clarified that the efficiency of endosomal escape of lipid nanoparticles containing the abovementioned lipid is still only a few percent (Non-Patent Literature 17), and therefore development of a technology that can further improve bioavailability is desired.

Furthermore, Dong et al. found a unique lipid-like substance, namely cKK-E12, through high-throughput screening, and achieved 0.002 mg siRNA/kg as $ED_{50}$ in F7 knockdown (Non-Patent Literature 18). Although this technique is the best in the literature in terms of activity, there is no information on safety aspects such as toxicity at high doses, biodegradability of lipids, and the like.

In recent years, it has been clarified that many cancer tissues, particularly cancer tissues of a human patient, are very rich in interstitial components including collagen, and these components significantly impede the permeability of nanoparticles in cancer tissues. Miniaturization of nanoparticles is perceived to be a very effective strategy to solve this problem. In fact, Cabral et al. have reported that by controlling the diameter of polymer micelles enclosed in platinum preparations to about 30 nm, permeation into cancer tissue is improved, and an antitumor effect is improved (Non-Patent Literature 19). The same strategy is perceived to be very effective for siRNA delivery, but it is technically difficult to control lipid nanoparticles (LNPs) to be small, and there are very few reports regarding this. In recent years, it has been reported that LNPs having a diameter of about 30 nm can be manufactured with favorable reproducibility by using a microchannel with a built-in micromixer that can achieve instantaneous mixing of two liquids (Non-Patent Literature 20 and Non-Patent Literature 21). Meanwhile, it has been found that siRNA delivery activity is significantly reduced by miniaturizing LNPs (Non-Patent Literature 22 and Non-Patent Literature 23). While overcoming this problem is extremely important in realizing an excellent siRNA delivery technology for cancer treatment, there is no information at present about how to overcome this problem.

CITATION LIST

Patent Literature

[Patent Literature 1]
PCT International Publication No. WO2005/32593
[Patent Literature 2]
PCT International Publication No. WO2006/101201
[Patent Literature 3]
PCT International Publication No. WO2007/102481
[Patent Literature 4]
Japanese Unexamined Patent Application, First Publication No. 2006-28030
[Patent Literature 5]
PCT International Publication No. WO2011/132713
[Patent Literature 6]
PCT International Publication No. WO2015/178343

Non-Patent Literature

[Non-Patent Literature 1]
Drug Delivery System, vol. 22-2, pp. 115-122, 2007
[Non-Patent Literature 2]
Biochemistry, vol. 26, pp. 2964-2972, 1987
[Non-Patent Literature 3]
Biochemistry, vol. 43, pp. 5618-5628, 2004
[Non-Patent Literature 4]
Journal of Controlled Release, vol. 98, pp. 317-323, 2004
[Non-Patent Literature 5]
Biochemistry, vol. 36, pp. 3008-3017, 1997
[Non-Patent Literature 6]
Nature Biotechnology, vol. 22, pp. 1546-1553, 2004
[Non-Patent Literature 7]
Nature Medicine, vol. 14, pp. 258-265, 2008
[Non-Patent Literature 8]
Journal of Controlled Release, vol. 143, pp. 311-317, 2010
[Non-Patent Literature 9]
Biological and Pharmaceutical Bulletin, vol. 34, pp. 1348-1351, 2011
[Non-Patent Literature 10]
Angewandte Chemie International Edition, vol. 51, pp. 8529-8533, 2012
[Non-Patent Literature 11]
Scientific Reports, 4: 4750, DOI: 10.1038/srep04750, 2014
[Non-Patent Literature 12]
Journal of Hepatology, vol. 64, pp. 547-555, 2016
[Non-Patent Literature 13]
Molecular Therapy, vol. 24, pp. 788-795, 2016
[Non-Patent Literature 14]
Molecular Therapy, vol. 21 (8), pp. 1570-1578, 2013
[Non-Patent Literature 15]
Nature Biotechnology, vol. 33 (8), pp. 870-876, 2015
[Non-Patent Literature 16]
Molecular Pharmaceutics, vol. 11, pp. 1424-1434, 2014
[Non-Patent Literature 17]
Nature Biotechnology, vol. 31 (7), pp. 638-646, 2013
[Non-Patent Literature 18]
Proceedings of the National Academy of Sciences of the United States of America, vol. 111 (11), pp. 3955-3960, 2014
[Non-Patent Literature 19]
Nature Nanotechnology, vol. 6, pp. 815-823, 2011
[Non-Patent Literature 20]
Journal of Physical Chemistry C Nanomater Interfaces, vol. 116 (34), pp. 18440-18450, 2012
[Non-Patent Literature 21]
Molecular Therapy-Nucleic Acids, vol. 1, e37, 2012
[Non-Patent Literature 22]
Journal of Controlled Release, vol. 229, pp. 48-57, 2016
[Non-Patent Literature 23]
Journal of Controlled Release, vol. 235, pp. 236-244, 2016
[Non-Patent Literature 24]
Journal of Controlled Release, vol. 225, pp. 183-191, 2016
[Non-Patent Literature 25]
American Association of Pharmaceutical Scientists Journal, vol. 14 (2), pp. 303-315, 2012

SUMMARY OF INVENTION

Technical Problem

An object of the present invention is to provide means for efficiently delivering siRNA or the like into a cell, particularly an immune cell such as a dendritic cell having antigen-presenting ability. More specifically, an object of the present invention is to provide a lipid membrane structure capable of efficiently delivering siRNA into various cells including an immune cell such as a dendritic cell, and a novel compound useful for manufacturing the lipid membrane structure.

In particular, an object of the present invention is to provide a novel compound and a lipid membrane structure which achieve both excellent efficiency of delivering siRNA or the like and high safety, thereby making it possible to overcome a decrease in activity when delivering siRNA or the like which is associated with a decrease in a particle diameter of LNPs.

Solution to Problem

The inventors of the present invention have intensively studied means for efficiently delivering siRNA into cells in order to achieve efficient knockdown of a target gene in an immune cell, particularly a dendritic cell having an antigen-presenting ability. As a result, they have found that significantly improved endosomal escape characteristics are achieved in formation of a lipid membrane structure such as a MEND by using, as lipid components, a lipid compound such as YSK12 in which the pKa has been increased by incorporating two unsaturated bonds in two fatty acid chains and extending a carbon chain in a hydrophilic part. They have also found that, in a lipid membrane structure prepared with a lipid composition including this lipid compound, target gene knockdown with siRNA can be extremely efficiently performed (Non-Patent Literature 24 and Patent Literature 6). In dendritic cells in which SOCS1 has been knocked down using this lipid membrane structure, a noticeable increase in cytokine production has been recognized, and in a mouse group to which these dendritic cells were administered, engraftment and/or proliferation of a transplanted tumor was completely inhibited.

The inventors of the present invention have further intensively studied a novel compound that can impart biodegradability, excellent endosomal escape ability, and LNP stabilization ability in order to provide, based on a structure of YSK12, and a novel compound and a lipid membrane structure which achieve both excellent efficiency of delivering a target substance such as siRNA to be delivered to cells (hereinafter referred to as a "delivery target substance") and high safety, thereby making it possible to overcome a decrease in activity when delivering a delivery target substance which is associated with a decrease in a particle diameter of LNPs. As means for obtaining these, first, two hydrocarbon chains having an appropriate length were extended from a tertiary hydroxyl group of YSK12, and medium to long chain fatty acids were bonded thereto via ester bonds. As a result, endosomal escape ability was improved by increasing a chain length of a hydrophobic scaffold, LNP stabilization ability was imparted by increasing hydrophobic interactions between lipid molecules, and biodegradability was imparted. In addition, in order to adjust an acid dissociation constant (pKa) of a pH-sensitive lipid as a parameter that greatly affects the dynamics of LNPs, a chemical structure around an amino group that is a hydrophilic site was optimized. As a result, it was confirmed that a compound represented by Formula (I) had desired properties, and therefore the present invention was completed.

That is, the present invention provides a lipid compound represented by Formula (I) or a salt thereof.

[Chem. 1]

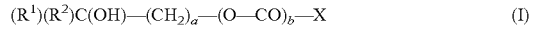

$(R^1)(R^2)C(OH)-(CH_2)_a-(O-CO)_b-X$  (I)

[In the formula, a represents an integer of 3 to 5; b represents an integer of 0 or 1; and $R^1$ and $R^2$ each independently represents a group represented by Formula (A):

[Chem. 2]

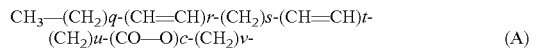

$CH_3-(CH_2)_q-(CH=CH)_r-(CH_2)_s-(CH=CH)_t-(CH_2)_u-(CO-O)_c-(CH_2)_v-$  (A)

(in the formula, q represents an integer of 1 to 9; r represents 0 or 1; s represents an integer of 1 to 3; t represents 0 or 1; u represents an integer of 1 to 8; c represents 0 or 1; and v represents an integer of 4 to 12, where, a case in which q is an integer of 3 to 5, r and t are 1, s is 1, and u+v is an integer of 6 to 10 is excluded in a case where both b and c are 0); and X represents a 5- to 7-membered non-aromatic heterocyclic group (where, the group is bonded to $(O-CO)_b-$ by a carbon atom, and one or two $C_{1-4}$ alkyl groups or $C_{2-4}$ alkenyl groups may be substituted on the ring), or X represents a group represented by Formula (B):

[Chem. 3]

$-(CH_2)_d-N(R^3)(R^4)$  (B)

(in the formula, d represents an integer of 0 to 3, and $R^3$ and $R^4$ each independently represents a $C_{1-4}$ alkyl group or a $C_{2-4}$ alkenyl group (where, the $C_{1-4}$ alkyl group or $C_{2-4}$ alkenyl group may be substituted by one or two phenyl groups), but $R^3$ and $R^4$ may be bonded to each other to form a 5- to 7-membered non-aromatic heterocycle (where, one or two $C_{1-4}$ alkyl groups or $C_{2-4}$ alkenyl groups may be substituted on the ring.)]

According to a preferable embodiment of the above-described invention, the above-described lipid compound or a salt thereof is provided in which r and t are 0, and q+s+u is an integer of 8 to 18 and is preferably an integer of 10 to 16 in Formula (A); the above-described lipid compound or a salt thereof is provided in which r is 1, t is 0, q is an integer of 5 to 9 and is preferably an integer of 6 to 8, and s+u is an integer of 5 to 9 and is preferably an integer of 6 to 8 in Formula (A); and the above-described lipid compound or a salt thereof is provided in which v is an integer of 5 to 12 and is preferably an integer of 6 to 10 in Formula (A). More preferably, the above-described lipid compound or a salt thereof is provided in which r and t are 0, q+s+u is an integer of 8 to 18 and is preferably an integer of 10 to 16, and v is an integer of 5 to 12 and is preferably an integer of 6 to 10 in Formula (A); and the above-described lipid compound or a salt thereof is provided in which r is 1, t is 0, q is an integer of 5 to 9 and is preferably an integer of 6 to 8, s+u is an integer of 5 to 9 and is preferably an integer of 6 to 8, and v is an integer of 5 to 12 and is preferably an integer of 6 to 10 in Formula (A).

According to a preferable embodiment of the above-described invention, the above-described lipid compound or a salt thereof is provided in which a is 4, and b is 0 or 1 in Formula (I). In a more preferable embodiment, the above-described lipid compound or a salt thereof is provided in which, in Formula (I), a is 4; b is 0 or 1; and $R^1$ and $R^2$ each independently represents, among groups represented by Formula (A), a group in which r and t are 0, q+s+u is an integer of 8 to 18 and is preferably an integer of 10 to 16, and v is an integer of 5 to 12 and is preferably an integer of 6 to 10, or a group in which r is 1, t is 0, q is an integer of 5 to 9 and is preferably an integer of 6 to 8, s+u is an integer of 5 to 9 and is preferably an integer of 6 to 8, and v is an integer of 5 to 12 and is preferably an integer of 6 to 10.

In addition, according to another preferable embodiment, the above-described lipid compound or a salt thereof is provided in which, in Formula (I), b is 0, and X is a group represented by Formula (B) (where, d is 0, and $R^3$ and $R^4$ each independently represents a $C_{1-4}$ alkyl group (where, the $C_{1-4}$ alkyl group represented by $R^3$ may be substituted by one phenyl group), or $R^3$ and $R^4$ form, by being bonded to each other, a 1-pyrrolidinyl group, a 1-piperidinyl group, a 1-morpholinyl group, or a 1-piperazinyl group (where, the 1-pyrrolidinyl group, 1-piperidinyl group, 1-morpholinyl group, or 1-piperazinyl group may be substituted by one $C_{1-4}$ alkyl group)); the above-described lipid compound or a salt thereof is provided in which, in Formula (I), b is 1, and X is a group represented by Formula (B) (where, d is integer of 1 to 3, and $R^3$ and $R^4$ each independently represents a $C_{1-4}$ alkyl group (where, the $C_{1-4}$ alkyl group represented by $R^3$ may be substituted by one phenyl group), or $R^3$ and $R^4$ form, by being bonded to each other, a 1-pyrrolidinyl group, a 1-piperidinyl group, a 1-morpholinyl group, or a 1-piperazinyl group (where, the 1-pyrrolidinyl group, 1-piperidinyl group, 1-morpholinyl group, or 1-piperazinyl group may be substituted by one or two same or different $C_{1-4}$ alkyl groups)); and the above-described lipid compound or a salt thereof is provided in which, in Formula (I), a 5- to 7-membered non-aromatic heterocyclic group (where, the group is bonded to $(O-CO)_b$— by a carbon atom) which is represented by X is a pyrrolidinyl group, a piperidinyl group, a morpholinyl group, or a piperazinyl group (where, the pyrrolidinyl group, piperidinyl group, morpholinyl group, or piperazinyl group may be substituted by one or two same or different $C_{1-4}$ alkyl groups).

In another aspect, the present invention provides a lipid compound represented by Formula (I) or a salt thereof which are used as lipid components of a lipid membrane structure for delivering a delivery target substance such as siRNA into a cell. According to a preferable embodiment of this invention, the above-described lipid compound is provided in which the cell is an immune cell or a cancer cell, and it is more preferably a dendritic cell, a monocyte, a macrophage, or a cancer cell; the above-described lipid compound or a salt thereof is provided in which the lipid membrane structure is a liposome; and the above-described lipid compound or a salt thereof is provided in which the lipid membrane structure is a multifunctional envelope-type nano device (MEND).

In still another aspect, the present invention provides a lipid membrane structure including a lipid compound represented by Formula (I) as lipid components. This lipid membrane structure is, for example, a liposome. In addition, according to a preferable embodiment of this present invention, the lipid membrane structure is a lipid membrane structure for delivering a substance, preferably siRNA, into a cell, and a delivery target substance such as siRNA is sealed therein. The lipid membrane structure can be used for target gene knockdown in a cell. According to a preferable embodiment of this invention, the cell is an immune cell or a cancer cell, and is more preferably a dendritic cell, a monocyte, a macrophage, or a cancer cell. For example, the lipid membrane structure can be used for knockdown of a target gene in dendritic cells having an antigen-presenting ability. Accordingly, from the above-mentioned viewpoint, the present invention also provides the above-described lipid membrane structure which is used for target gene knockdown in a cell, preferably an immune cell or a cancer cell, and more preferably a dendritic cell, a monocyte, a macrophage, or a cancer cell.

In addition, according to another preferable embodiment, a lipid membrane structure is provided which includes, as lipid components, one or two or more compounds selected from the group consisting of a lipid compound of Formula (I), 1-palmitoyl-2-oleyl-sn-glycero-3-phosphoethanolamine (POPE), cholesterol (Chol), 1,2-dimyristoyl-sn-glycerol, and methoxypolyethylene glycol 2000 dimyristoyl glycerol (PEG-DMG 2000); a lipid membrane structure is provided which includes, as lipid components, one or two or more compounds selected from the group consisting of a lipid compound of Formula (I), cholesterol (Chol), 1,2-dimyristoyl-sn-glycerol, and methoxypolyethylene glycol 2000 dimyristoyl glycerol (PEG-DMG 2000); the above-described lipid membrane structure is provided in which the cell is an immune cell, preferably a dendritic cell, a monocyte, or a macrophage; the above-described lipid membrane structure that is a liposome; and the above-described lipid compound that is multifunctional envelope-type nano device (MEND).

In addition, the present invention provides a method for delivering a delivery target substance such as siRNA into a cell, preferably an immune cell, and particularly preferably a dendritic cell, the method including a step of bringing, into a cell, the above-described lipid membrane structure which contains a lipid compound represented by Formula (I) as lipid components, and in which a delivery target substance is sealed therein. This method may be performed in vivo in mammals including humans, or may be performed in vitro using cells separated and collected from a living body.

For example, in a case of using a dendritic cell, dendritic cell therapy can be performed by introducing a delivery target substance into dendritic cells separated and collected from a patient by the above-described method, and then administering dendritic cells in which a target gene has been knocked down to the patient. Accordingly, the present invention provides an immunotherapy method in which dendritic cells are separated and collected from a patient, a delivery target substance is introduced into the dendritic cells in vitro, and then dendritic cells in which a target gene has been knocked down are administered to the patient. In addition, the present invention provides a lipid membrane structure which is used for target gene knockdown in a dendritic cell in immunotherapy in which dendritic cells are separated and collected from a patient, a delivery target substance is introduced into the dendritic cells in vitro, and then dendritic cells in which a target gene has been knocked down are administered to the patient.

Advantageous Effects of Invention

The lipid compound of the present invention can provide a lipid membrane structure that achieves both excellent efficiency of delivering a delivery target substance such as siRNA and high safety, thereby making it possible to overcome a decrease in activity when delivering siRNA or the like which is associated with a decrease in a particle diameter of LNPs. In addition, biodegradability, excellent endosomal escape ability, and LNP stabilization ability can be imparted to the lipid membrane structure. The lipid membrane structure provided by the invention can efficiently transfer into any cell, for which introduction of a delivery target substance such as siRNA is difficult, such as an immune cell including a dendritic cell, and can efficiently escape from endosomes. Accordingly, the lipid membrane structure can efficiently release a sealed delivery target substance in a cell, and a target gene can be knocked out by the delivery target substance. Therefore, using the lipid membrane structure of the present invention, it is possible to perform effective immunotherapy, preferably dendritic cell therapy, in which a substance such as siRNA is used in cancer treatment for example. In addition, in a case where a lipid membrane structure such as a liposome is prepared using the lipid compound provided by the present invention as lipid components, significantly improved endosomal escape characteristics are achieved, and thereby it is possible to efficiently deliver a delivery target substance such as siRNA from a lipid membrane structure including this lipid compound into cytoplasm.

DESCRIPTION OF EMBODIMENTS

Figure 1:
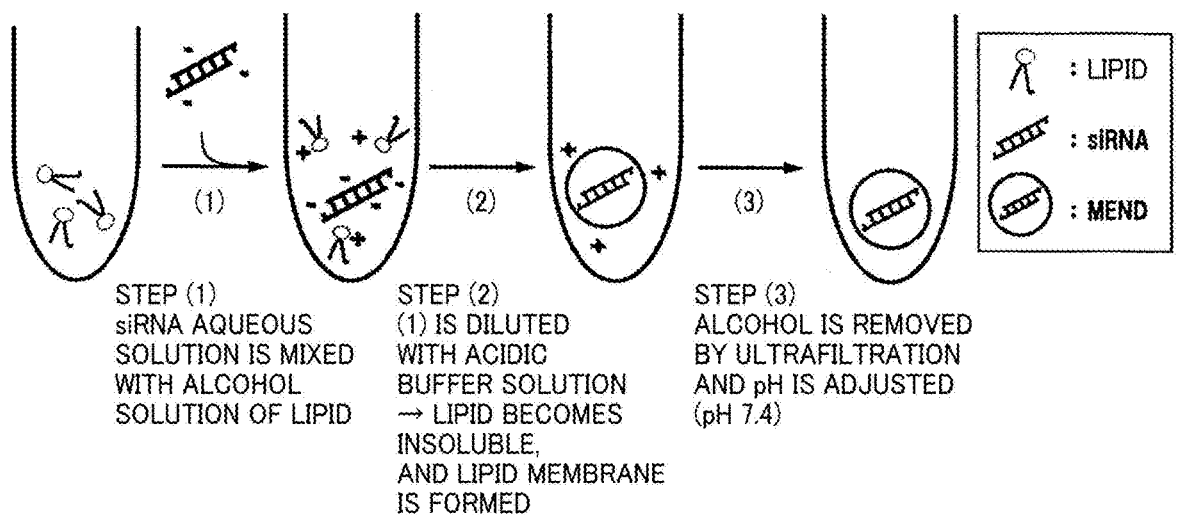
FIG. 1 is a schematic diagram of a procedure for preparing LNPs by an alcohol dilution method.

Hereinafter, embodiments of the present invention will be specifically described. In the specification of the present application, "X1 to X2 (X1 and X2 being real numbers satisfying X1<X2)" means "X1 or more and X2 or less."

A lipid compound according to an embodiment of the present invention (the lipid compound of the present invention) is represented by Formula (I).

[Chem. 4]

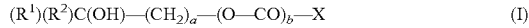

$(R^1)(R^2)C(OH)$—$(CH_2)_a$—$(O$—$CO)_b$—$X$     (I)

In Formula (I), a represents an integer of 3 to 5, and is preferably 4.

b represents an integer of 0 or 1. In a case where b is 0, this means that the —O—CO— group is not present and b is a single bond.

In Formula (I), $R^1$ and $R^2$ each independently represents a group represented by Formula (A).

[Chem. 5]

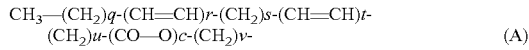

$CH_3$—$(CH_2)_q$-$(CH$=$CH)_r$-$(CH_2)_s$-$(CH$=$CH)_t$-$(CH_2)_u$-$(CO$—$O)_c$-$(CH_2)_v$-     (A)

In Formula (A), q represents an integer of 1 to 9; r represents 0 or 1; s represents an integer of 1 to 3; t represents 0 or 1; u represents an integer of 1 to 8; and v represents an integer from 4 to 12. c represents 0 or 1. A case where b is 0 and c is 1, or b is 1 and c is 0 is preferable.

In a preferable embodiment, r and t are 0, and q+s+u is an integer of 8 to 18 and is preferably an integer of 10 to 16. In another preferable embodiment, r is 1, t is 0, q is an integer of 5 to 9 and is preferably an integer of 6 to 8, and s+u is an integer of 5 to 9 and is preferably an integer of 6 to 8. In still another preferable embodiment, v is an integer of 4 to 12, is preferably an integer of 6 to 10, and is more preferably 6. An embodiment in which a is 4, and b is 0 or 1 is also preferable.

However, in a case where both b and c are 0, a case where q is an integer of 3 to 5, r and t are 1, s is 1, and u+v is an integer of 6 to 10 is excluded.

In Formula (I), X represents a 5- to 7-membered non-aromatic heterocyclic group or a group represented by Formula (B).

[Chem. 6]

—$(CH_2)_d$-$N(R^3)(R^4)$     (B)

The 5- to 7-membered non-aromatic heterocyclic group represented by X is bonded to (O—CO)$_b$— by a carbon atom, and one or two $C_{1-4}$ alkyl groups (an alkyl group having 1 to 4 carbon atoms) or a $C_{2-4}$ alkenyl group (an alkenyl group having 2 to 4 carbon atoms) may be substituted on the ring. Examples of heteroatoms contained in the 5- to 7-membered non-aromatic heterocyclic group include a nitrogen atom, an oxygen atom, and a sulfur atom. One ring-constituting heteroatom may be contained, or two or more heteroatoms that are the same as or different from each other may be contained. A heterocyclic ring constituting the heterocyclic group may contain one or two or more double bonds, but the heterocyclic ring does not become an aromatic ring. There in a case where a saturated hetero ring is preferable. In addition, among substituents in which one or two hydrogen atoms in the 5- to 7-membered non-aromatic heterocyclic group are substituted, examples of $C_{1-4}$ alkyl groups include a methyl group, an ethyl group, an n-propyl group, an n-butyl group, an isopropyl group, an isobutyl group, a tert-butyl group, and the like, and examples of $C_{2-4}$ alkenyl groups include an ethenyl group (a vinyl group), a propenyl group, a butenyl group, and the like.

In Formula (B), d represents an integer of 0 to 3, and $R^3$ and $R^4$ each independently represents a $C_{1-4}$ alkyl group or a $C_{2-4}$ alkenyl group. Examples of $C_{1-4}$ alkyl groups and $C_{2-4}$ alkenyl groups are the same as those described above. The $C_{1-4}$ alkyl group or $C_{2-4}$ alkenyl group represented by $R^3$ and $R^4$ may each be substituted with one or two phenyl groups. In addition, $R^3$ and $R^4$ may be bonded to each other to form a 5- to 7-membered non-aromatic heterocycle. The 5- to 7-membered non-aromatic heterocycle may be substituted by one or two $C_{1-4}$ alkyl groups or $C_{2-4}$ alkenyl groups.

According to another preferable embodiment, in the lipid compound represented by Formula (I), b is 0, and X represents a group represented by Formula (B). In this embodiment, d is preferably 0, and $R^3$ and $R^4$ may each independently represent a $C_{1-4}$ alkyl group (where, the $C_{1-4}$ alkyl group represented by $R^3$ is substituted by one phenyl group), or they may be bonded to each other to form a 5- to 7-membered non-aromatic heterocycle. In a case where $R^3$ and $R^4$ are bonded to each other, they preferably form a 1-pyrrolidinyl group, a 1-piperidinyl group, a 1-morpholinyl group, or a 1-piperazinyl group, and the 1-pyrrolidinyl group, the 1-piperidinyl group, the 1-morpholinyl group, or the 1-piperazinyl group may be substituted by one $C_{1-4}$ alkyl group.

According to still another preferable embodiment, b represents 1, and X represents a group represented by Formula (B). In this embodiment, d is preferably an integer of 1 to 3, and $R^3$ and $R^4$ may each independently represent a $C_{1-4}$ alkyl group (where, the $C_{1-4}$ alkyl group represented by $R^3$ may be substituted by one phenyl group), and they may be bonded to each other to form a 5- to 7-membered non-aromatic heterocycle. In a case where $R^3$ and $R^4$ are bonded to each other, they preferably form a 1-pyrrolidinyl group, a 1-piperidinyl group, a 1-morpholinyl group, or a 1-piperazinyl group, and the 1-pyrrolidinyl group, the 1-piperidinyl group, the 1-morpholinyl group, or the 1-piperazinyl group may be substituted by one or two same or different $C_{1-4}$ alkyl groups.

In addition, according to another preferable embodiment, b is 1, and X is a 5- to 7-membered non-aromatic heterocyclic group (where, the group is bonded to (O—CO)$_b$— by a carbon atom), in which the 5- to 7-membered non-aromatic heterocyclic group is preferably a pyrrolidinyl group, a piperidinyl group, a morpholinyl group, or a piperazinyl group, where, the pyrrolidinyl group, piperidinyl group, morpholinyl group, or piperazinyl group may be substituted by one or two same or different $C_{1-4}$ alkyl groups.

The lipid compound represented by Formula (I) may be present as an acid addition salt. The kind of acid constituting the salt is not particularly limited, and any of mineral acids or organic acids may be used. For example, mineral salts such as hydrochlorides, nitrates, or sulfates, or organic acid salts such as tartrates, oxalates, maleates, malates, p-toluenesulfonates, or methanesulfonates can be exemplified, but examples are not limited thereto. The lipid compound represented by Formula (I) or a salt thereof may be present as a hydrate or a solvate in some cases, and these substances are also included in the scope of the present invention. In addition, in a case where $R^1$ and $R^2$ are different from each other, optical isomers may be present in some cases, and pure forms of optical isomers, mixtures of any optically active isomers, racemates, and the like are also included in the scope of the present invention.

Examples of particularly preferable compounds among compounds of Formula (I) include a compound in which $R^1$ and $R^2$ are the same as each other, and a is 4. The compounds of Formula (I) including this compound can be easily manufactured by a method specifically shown in the examples of the present specification. By appropriately selecting raw material compounds, reagents, reaction conditions, and the like with reference to the manufacturing method of the examples, those skilled in the art can easily manufacture any compound included in the range of Formula (I). A pKa of the compound of Formula (I) is not particularly limited, but it can be selected, for example, such that it is about 4.0 to 9.0, preferably about 4.5 to 8.5. It is preferable that the type of each substituent be selected so that a pKa is within these ranges. The uptake of lipid structures such as liposomes into cells by endocytosis is affected by a pKa of the lipid structure. Depending on the cell type, a pKa of lipid structures at which they are easily taken up by endocytosis differs. For this reason, it is preferable to adjust a pKa of the compound of Formula (I) so that a pKa of the lipid structure is within a range in which it can be easily taken into a target cell.

Examples of lipids constituting the lipid membrane structure of the present invention include phospholipids, glycolipids, sterols, saturated or unsaturated fatty acid esters, saturated or unsaturated fatty acids, and the like.

Examples of phospholipids and phospholipid derivatives include phosphatidylethanolamine, phosphatidylcholine, phosphatidylserine, phosphatidylinositol, phosphatidylglycerol, cardiolipin, sphingomyelin, ceramide phosphorylethanolamine, ceramide phosphorylglycerol, ceramide phosphorylglycerol phosphate, 1,2-dimyristoyl-1,2-deoxyphosphatidylcholine, plasmalogen, phosphatidic acid, and the like. These can be used alone or in combination of two or more kinds thereof. Fatty acid residues in these phospholipids are not particularly limited, and examples thereof include saturated or unsaturated fatty acid residues having 12 to 20 carbon atoms. Specific examples thereof include acyl groups derived from fatty acids such as lauric acid, myristic acid, palmitic acid, stearic acid, oleic acid, and linoleic acid. In addition, phospholipids derived from natural products such as egg yolk lecithin and soybean lecithin can also be used.

Examples of glycolipids include glyceroglycolipids (for example, sulfoxyribosyl glyceride, diglycosyl diglyceride, digalactosyl diglyceride, galactosyl diglycerides, glycosyl diglycerides), glycosphingolipids (for example, galactosyl cerebroside, lactosyl cerebroside, ganglioside), and the like.

Examples of sterols include animal-derived sterols (for example, cholesterol, cholesterol succinic acid, lanosterol, dihydrolanosterol, desmosterol, dihydrocholesterol), plant-derived sterols (phytosterol) (for example, stigmasterol, sitosterol, campesterol, brush castrol), sterols derived from microorganisms (for example, timosterol, ergosterol), and the like.

Examples of saturated or unsaturated fatty acids include saturated or unsaturated fatty acids having 12 to 20 carbon atoms, such as palmitic acid, oleic acid, stearic acid, arachidonic acid, myristic acid, and the like.

Examples of saturated or unsaturated fatty acid esters include glycerin fatty acid esters in which one or two hydroxyl groups of glycerol are ester-bonded with a fatty acid. Examples of fatty acid residues in a glycerin fatty acid ester include acyl groups derived from saturated or unsaturated fatty acids having 12 to 20 carbon atoms, such as palmitic acid, oleic acid, stearic acid, arachidonic acid, myristic acid, and the like. Specific examples thereof include dimyristoyl glycerol (DMG), distearoyl glycerol (DSG), and the like.

The form of the lipid membrane structure is not particularly limited. Examples thereof include, as a form dispersed in an aqueous solvent, single membrane liposomes, multi membrane liposomes, an O/W type emulsion, a W/O/W type emulsion, spherical micelles, string micelles, layered structures of an atypical form, and the like. A preferable form of the lipid membrane structure of the present invention is a liposome. Hereinafter, although a liposome may be described as a preferable embodiment of the lipid membrane structure of the present invention, the lipid membrane structure of the present invention is not limited to liposomes.

The lipid membrane structure of the present invention is a lipid membrane structure for delivering a delivery target substance such as siRNA into a cell, in which the delivery target substance is sealed therein, and the lipid membrane structure is characterized by containing a lipid compound represented by Formula (I). The type of cell (a target cell) to which the delivery target substance is delivered by the lipid membrane structure of the present invention is not particularly limited. The lipid membrane structure of the present invention can deliver the delivery target substance to a wide variety of cells such as various cells constituting animals, such as immune cells, endothelial cells, epithelial cells, fibroblasts, hepatocytes (liver parenchymal cells), pancreatic cells, nerve cells, smooth muscle cells, and cardiomyocytes; cancer cells that have become cancerous; stem cells having differentiation ability; and the like. In addition, a target cell may be a cell in an animal body or a cell cultured in vitro such as a cultured cell or a primary cultured cell. Examples of immune cells include dendritic cells, macrophages, lymphocytes (T cells, B cells, NK cells), granulocytes, monocytes, and the like. Suitable examples of cells to which the lipid membrane structure of the present invention can be delivered include immune cells and cancer cells, and particularly suitable examples include dendritic cells, monocytes, macrophages, and cancer cells.

Hereinafter, siRNA will be described as a preferable example of a substance to be delivered (a delivery target substance), but the delivery target substance is not limited to siRNA. For example, in addition to nucleic acids such as microRNA, mRNA, and plasmids, active ingredients of any medicine such as an antitumor agent, an anti-inflammatory agent, an antibacterial agent, and an antiviral agent; and any substances such as saccharides, peptides, low-molecular-weight compounds, and metal compounds can be sealed in the lipid membrane structure of the present invention.

siRNA (small interfering RNA) is low-molecular-weight double-stranded RNA consisting of 21 to 23 base pairs, is involved in RNA interference (RNAi), and inhibits gene expression in a sequence-specific manner by destroying mRNA. Synthetic siRNA has been reported to cause RNA interference in human cells, and a gene can be knocked down by RNA interference using siRNA. Accordingly, it can be expected that siRNA will be able to be used as a medicine and used in therapeutic fields such as in cancer treatment. The type of siRNA that can be used in the present invention is not particularly limited, and any siRNA may be used as long as it can cause RNA interference. In general, double stranded RNA consisting of 21 to 23 base pairs which is RNA having a structure in which the 3' part of the RNA strand protrudes by 2 bases, and each strand has a structure with a phosphate group at the 5' end and a hydroxyl group at the 3' end can be used as the siRNA in the present invention. In addition, examples thereof include siRNA in which hydroxyl groups at the 2' position of a ribose skeleton are partially substituted with methoxy groups, fluoro groups, or methoxyethyl groups, and phosphodiester bonds are partially substituted with phosphorothioate bonds.

The lipid membrane structure of the present invention can be used to deliver siRNA into cells, preferably immune cells or cancer cells, particularly preferably dendritic cells, monocytes, macrophages, or cancer cells. This method may be performed in vivo in mammals including humans, or may be performed in vitro using cells separated and collected from a living body. For example, in a case of using a dendritic cell, dendritic cell therapy can be performed by introducing siRNA into dendritic cells separated and collected from a patient using the lipid membrane structure of the present invention, and then administering dendritic cells in which a target gene has been knocked down to the patient. Without being bound by any particular theory, the double-stranded siRNA delivered into a cell by the lipid membrane structure of the present invention is dissociated into a single strand under the action of an enzyme called helicase, and forms a complex (RISC) with an Argonaute protein that shows endonuclease activity against a target mRNA, and thereby a target gene can be knocked down by RNA interference.

The lipid compound of Formula (I) may be used alone as lipid components of the lipid membrane structure of the present invention, but generally, it is preferable that one or two or more kinds of the lipids described above be used, and the lipid compound of Formula (I) be combined to form a lipid membrane structure. A combination of a plurality of lipids, and a blending ratio thereof are not particularly limited, but as will be specifically shown in the examples, for example, the type and blending ratio of lipids to be used can be optimized using knockdown activity with respect to a target gene, or the like as an index. For example, regarding a combination of a compound of Formula (I), 1-palmitoyl-2-oleyl-sn-glycero-3-phosphoethanolamine (POPE), cholesterol (Chol), 1,2-dimyristoyl-sn-glycerol, and methoxypolyethylene glycol 2000 dimyristoyl glycerol (PEG-DMG 2000) as lipid components, knockdown activity can be increased by setting a content of the compound of Formula (I) to 80 to 90 mol %, preferably to about 85 mol %, setting a content of PEG-DMG 2000 to about 1 to 2 mol %, preferably to about 1 mol %, and/or setting a POPE/Chol ratio (a molar ratio) to about 0/15 to 4/11, preferably to 0/15 when there is 85 mol % of the compound of Formula (I), but examples of these specific lipids and their blending ratios therebetween are not limited thereto.

A particle diameter of the lipid membrane structure of the present invention is not particularly limited, but in a preferable embodiment, an average particle diameter is about 60 to 140 nm and is more preferably about 80 to 120 nm, and in another preferable embodiment, an average particle diameter is about 20 to 50 nm, which is preferable from the viewpoint of knockdown efficiency. A polydispersity index (PDI) is about 0.05 to 0.1, is preferably about 0.06 to 0.08, and is more preferably about 0.07. A zeta potential can be within a range of 5.5 mV to 6.0 mV and is preferably about 5.8 mV.

The lipid membrane structure of the present invention can be subjected to appropriate surface modification as required.

For example, in order to promote the nuclear translocation of the lipid membrane structure of the present invention, for example, the lipid membrane structure can be surface-modified with an oligosaccharide compound having 3 or more sugars. The type of oligosaccharide compound having 3 or more sugars is not particularly limited. For example, an oligosaccharide compound having 3 to about 10 sugar units bound thereto can be used, and an oligosaccharide compound having 3 to about 6 sugar units bound thereto can be preferably used.

More specifically, examples of oligosaccharide compounds include trisaccharide compounds such as cellotriose (β-D-glucopyranosyl-(1→4)-β-D-glucopyranosyl-(1→4)-D-glucose), chacotriose (α-L-rhamnopyranosyl-(1→2)-[α-L-rhamnopyranosyl-(1→4)]-D-glucose), gentianose (β-D-fructofuranosyl β-D-glucopyranosyl-(1→6)-α-D-glucopyranoside), isomaltotriose (α-D-glucopyranosyl-(1→6)-α-D-glucopyranosyl-(1→6)-D-glucose), isopanose (α-D-glucopyranosyl-(1→4)-[α-D-glucopyranosyl-(1→6)]-D-glucose), maltotriose (α-D-glucopyranosyl-(1→4)-α-D-glucopyranosyl-(1→4)-D-glucose), manninotriose (α-D-galactopyranosyl-(1→6)-α-D-galactopyranosyl-(1→6)-D-glucose), melezitose (α-D-glucopyranosyl-(1→3)-β-D-fructofuranosyl=α-D-glucopyranoside), panose (α-D-glucopyranosyl-(1→6)-α-D-glucopyranosyl-(1→4)-D-glucose), planteose (α-D-galactopyranosyl-(1-6)-β-D-fructofuranosyl=α-D-glucopyranoside), raffinose (β-D-fructofuranosyl=α-D-galactopyranosyl-(1-6)-α-D-glucopyranoside), solatriose (α-L-rhamnopyranosyl-(1→2)-[3-D-glucopyranosyl-(1→3)]-D-galactose), and umbelliferose (β-D-fructofuranosyl=α-D-galactopyranosyl-(1→2)-α-D-galactopyranoside); tetrasaccharide compounds such as lycotetraose (β-D-glucopyranosyl-(1→2)-[β-D-xylopyranosyl-(1→3)]-β-D-glucopyranosyl-(1→4)-β-D-galactose), maltotetraose (α-D-glucopyranosyl-(1→4)-α-D-glucopyranosyl-(1→4)-α-D-glucopyranosyl-(1→4)-D-glucose), and stachyose (β-D-fructofuranosyl=α-D-galactopyranosyl-(1→6)-α-D-galactopyranosyl-(1→6)-α-D-glucopyranoside); pentasaccharide compounds such as maltopentaose (α-D-glucopyranosyl-(1→4)-α-D-glucopyranosyl-(1→4)-α-D-glucopyranosyl-(1→4)-α-D-glucopyranosyl-(1→4)-D-glucose), and verbascose (β-D-fructofuranosyl=α-D-galactopyranosyl-(1-6)-α-D-galactopyranosyl-(1→6)-α-D-galactopyranosyl-(1→6)-α-D-glucopyranoside); and hexasaccharide compounds such as maltohexaose (α-D-glucopyranosyl-(1→4)-α-D-glucopyranosyl-(1→4)-α-D-glucopyranosyl-(1→4)-α-D-glucopyranosyl-(1→4)-α-D-glucopyranosyl-(1→4)-D-glucose), but examples are not limited thereto.

An oligosaccharide compound that is a trimer or hexamer of glucose is suitably used, and an oligosaccharide compound that is a trimer or tetramer of glucose is more suitably used. More specifically, isomaltotriose, isopanose, maltotriose, maltotetraose, maltopentaose, maltohexaose, or the like can be suitably used. Among them, maltotriose, maltotetraose, maltopentaose, or maltohexaose in which glucose is α1-4 bonded is even more preferable. Maltotriose or maltotetraose is particularly preferable, and maltotriose is most preferable. An amount of surface modification of a lipid membrane structure with an oligosaccharide compound is not particularly limited. For example, it may be about 1 to 30 mol %, is preferably about 2 to 20 mol %, and is more preferably about 5 to 10 mol % with respect to a total amount of lipid.

A method of modifying a surface of a lipid membrane structure with an oligosaccharide compound is not particularly limited. For example, a liposome (Patent Literature 3) in which a surface of a lipid membrane structure is modified with a monosaccharide such as galactose or mannose is known, and a method of modifying a surface described in this publication can be employed. The entire disclosure of the above publication is incorporated herein by reference. This means is a method in which a monosaccharide compound is bonded to a polyalkylene glycolated lipid to modify a surface of a lipid membrane structure, and this means is preferable because a surface of a lipid membrane structure can be modified with a polyalkylene glycol at the same time.

Modification of a surface of a lipid membrane structure with a hydrophilic polymer such as polyalkylene glycol improves stability of retention of liposomes in the blood in some cases. This means is described in, for example, Japanese Unexamined Patent Application, First Publication No. H1-249717, Japanese Unexamined Patent Application, First Publication No. H2-149512, Japanese Unexamined Patent Application, First Publication No. H4-346918, Japanese Unexamined Patent Application, First Publication No. 2004-10481, and the like. As the hydrophilic polymer, a polyalkylene glycol is preferable. As a polyalkylene glycol, for example, polyethylene glycol, polypropylene glycol, polytetramethylene glycol, polyhexamethylene glycol, and the like can be used. A molecular weight of the polyalkylene glycol is, for example, about 300 to 10,000, is preferably about 500 to 10,000, and is more preferably about 1,000 to 5,000.

Surface modification of a lipid membrane structure with polyalkylene glycol can be easily performed by constructing a lipid membrane structure using, for example, a polyalkylene-glycol-modified lipid as a lipid constituting lipid membrane. For example, in a case where modification with polyethylene glycol is performed, stearyl polyethylene glycol (for example, PEG45 stearate (STR-PEG45) or the like) can be used. In addition, it is also possible to use polyethylene glycol derivatives such as N-[carbonyl-methoxypolyethylene glycol-2000]-1,2-dipalmitoyl-sn-glycero-3-phosphoethanolamine, n-[carbonyl-methoxypolyethyleneglycol-5000]-1,2-dipalmitoyl-sn-glycero-3-phosphoethanolamine, N-[carbonyl-methoxypolyethyleneglycol-750]-1,2-distearoyl-sn-glycero-3-phosphoethanolamine, N-[carbonyl-methoxypolyethyleneglycol-2000]-1,2-distearoyl-sn-glycero-3-phosphoethanolamine, and N-[carbonyl-methoxypolyethyleneglycol-5000]-1,2-distearoyl-sn-glycero-3-phosphoethanolamine, but the polyalkylene glycolated lipid is not limited to these examples.

In addition, surface modification with polyalkylene glycol and an oligosaccharide compound can be achieved at the same time by bonding an oligosaccharide compound to a polyalkylene glycol. However, a method of modifying a surface of a lipid membrane structure with a polyalkylene glycol or an oligosaccharide compound is not limited to the above-described method, and for example, in some cases, surface modification can be performed by using lipidated compounds such as stearylated polyalkylene glycols and oligosaccharide compounds as a constituent lipid of a lipid membrane structure.

In manufacture of the lipid membrane structure of the present invention, as lipid derivatives for enhancing retention in blood, it is also possible to use glycophorin, ganglioside GM1, phosphatidylinositol, ganglioside GM3, glucuronic acid derivatives, glutamic acid derivatives, polyglycerin phospholipid derivatives, and the like. Furthermore, as hydrophilic polymers for enhancing retention in blood, in addition to polyalkylene glycol, it is also possible to use dextran, pullulan, ficoll, polyvinyl alcohol, a styrene-maleic anhydride alternating copolymer, a divinyl ether-maleic anhydride alternating copolymer, amylose, amylopectin, chitosan, mannan, cyclodextrin, pectin, carrageenan, and the like for surface modification.

The lipid membrane structure of the present invention may include one or two or more substances selected from the group consisting of membrane stabilizers such as sterols or glycerin or fatty acid esters thereof; antioxidants such as tocopherol, propyl gallate, ascorbyl palmitate, or butylated hydroxytoluene; charged substances; membrane polypeptides; and the like. Examples of charged substances that impart a positive charge include saturated or unsaturated aliphatic amines such as stearylamine and oleylamine; saturated or unsaturated cationic synthetic lipids such as dioleoyltrimethylammoniumpropane; cationic polymers; and the like. Examples of charged substances that impart a negative charge include dicetyl phosphate, cholesteryl hemisuccinate, phosphatidylserine, phosphatidylinositol, phosphatidic acid, and the like. Examples of membrane polypeptides include a membrane superficial polypeptide, an membrane integral polypeptide, and the like. A formulation amount of these substances is not particularly limited, and it can be appropriately selected according to the purpose.

In addition, to the lipid membrane structure of the present invention, for example, it is possible to impart any one or two or more functions such as a temperature change sensitivity function, a membrane permeation function, a gene expression function, and a pH sensitivity function. By appropriately adding these functions, for example, retention of a lipid membrane structure having a nucleic acid containing a gene, and the like in blood can be improved, and a rate of capturing by reticuloendothelial tissues such as the liver and spleen can be reduced. In addition to these results, the lipid membrane structure that has been taken up into a target cell by endocytosis can efficiently escape from the endosome and transfer into the nucleus, and thereby it is possible to achieve high gene expression activity in the nucleus.

Examples of temperature change-sensitive lipid derivatives capable of imparting a temperature change-sensitive function include dipalmitoyl phosphatidylcholine and the like. Examples of pH-sensitive lipid derivatives capable of imparting a pH-sensitive function include dioleoylphosphatidylethanolamine and the like.

The lipid membrane structure of the present invention can also be modified with substances such as antibodies that can specifically bind to receptors and antigens of a cell surface.

This modification can improve efficiency of substance delivery into the nucleus of a cell. For example, on a surface of a lipid membrane structure, it is preferable to dispose a monoclonal antibody against a biological component specifically expressed in a target tissue or organ. This technique is described in Non-Patent Literature 25 and the like, for example. Regarding a structural component of a lipid membrane structure, by incorporating a lipid derivative capable of reacting with a mercapto group in monoclonal antibodies and their fragments (for example, a Fab fragment, a F(ab')$_2$ fragment, a Fab' fragment, or the like), for example, a lipid derivative having a maleimide structure such as poly(ethylene glycol)-α-distearoylphosphatidylethanolamine-ω-maleimide, and α-[N-(1,2-distearoyl-sn-glycero-3-phosphorylethyl)carbamyl)-ω-[3-[2-(2,5-dihydro-2,5-dioxo-1H-pyrrol-1-yl)ethanecarboxamido]propyl}-poly(oxy-1,2-ethanediyl), a monoclonal antibody can be bound to a surface of a membrane of the lipid membrane structure.

The surface of the lipid membrane structure of the present invention may be modified with a polypeptide containing a plurality of consecutive arginine residues (hereinafter referred to as "polyarginine"). Regarding the polyarginine, a polypeptide containing 4 to 20 consecutive arginine residues is preferably used, a polypeptide consisting of only 4 to 20 consecutive arginine residues is more preferable, and octaarginine is particularly preferable. By modifying a surface of a lipid membrane structure such as a liposome with polyarginine such as octaarginine, the efficiency of intracellular delivery of a target substance sealed in a liposome can be improved (Non-Patent Literature 4 and Patent Literature 1). Modification of a surface of a lipid membrane structure with polyarginine can be easily performed by using, for example, a lipid-modified polyarginine such as stearylated octaarginine as a constituent lipid of the lipid membrane structure according to the method described in the above-mentioned publications. The disclosures of the above-mentioned publications and the disclosures of all documents cited in these publications are incorporated herein by reference.

In addition, in a case of sealing siRNA in the lipid membrane structure of the present invention, a compound having a function of introducing a nucleic acid can be added as necessary. Examples of such compounds include O,O'—N-didodecanoyl-N-(α-trimethylammonioacetyl)-diethanolamine chloride, O,O'—N-ditetradecanoyl-N-(α-trimethylammonioacetyl)-diethanolamine chloride, O,O'—N-dihexadecanoyl-N-(α-trimethylammonioacetyl)-diethanolamine chloride, O,O'—N-dioctadecenoyl-N-(α-trimethylammonioacetyl)-diethanolamine chloride, O,O', O"-tridecanoyl-N-(ω-trimethylammoniodecanoyl)aminomethane bromide and N-[α-trimethylammonioacetyl]-didodecyl-D-glutamate, dimethyl dioctadecyl ammonium bromide, 2,3-dioleoyloxy-N-[2-(sperminecarboxamido)ethyl)-N,N-dimethyl-1-propaneammonium trifluoroacetate, 1,2-dimyristyloxypropyl-3-dimethyl-hydroxyethylammonium bromide, 3-β-[N—(N',N'-dimethylaminoethane)carbamoyl]cholesterol, and the like. These compounds having a function of introducing a nucleic acid may be disposed at any position on a membrane of the lipid membrane structure, and/or may be filled in the lipid membrane structure.

A multifunctional envelope-type nano device (MEND) is known, and it can be suitably used as the lipid membrane structure of the present invention. As a MEND, for example, a device having a structure in which a complex of a nucleic acid such as a plasmid DNA and a cationic polymer such as protamine is used as a core, and the core is sealed inside a lipid envelope membrane in a liposome form has been reported. In addition, it has also been reported that a peptide for adjusting pH responsiveness and membrane permeability can be disposed on the lipid envelope membrane of a MEND as needed, and an outer surface of the lipid envelope membrane can be modified with an alkylene glycol such as polyethylene glycol. A MEND is also known to be able to have a design in which a condensed DNA and cationic polymers are sealed inside the lipid envelope of a MEND so that gene expression can be achieved efficiently. Regarding the MEND, for example, summary section of, for example, Non-Patent Literature 1 and the like can be referred to. The disclosures of the above-mentioned publications and the disclosures of all documents cited in these summary sections are incorporated herein by reference.

The form of the lipid membrane structure is not particularly limited, and examples thereof include a form dispersed in an aqueous solvent (for example, water, physiological saline solution, phosphate-buffered saline, and the like), a form obtained by freeze-drying this aqueous dispersion, and the like.

A method for manufacturing a lipid membrane structure is not particularly limited, and any method available to those skilled in the art can be adopted. For example, a lipid membrane structure can be manufactured by dissolving all lipid components in an organic solvent such as chloroform, forming a lipid membrane by vacuum drying with an evaporator or spray drying with a spray dryer, thereafter, adding an aqueous solvent to the above dried mixture, and furthermore, emulsifying with emulsifiers such as a homogenizer, an ultrasonic emulsifier, or a high-pressure jet emulsifier. In addition, it can also be manufactured by a method well-known as a method for manufacturing a liposome, for example, a reverse-phase evaporation method or the like. In a case where it is desired to control a size of a lipid membrane structure, extrusion (extrusion filtration) may be performed under high pressure using a membrane filter having a uniform pore diameter. A size of the lipid membrane structure in a dispersed state is not particularly limited, but for example, in a case of a liposome, an average particle diameter is about 60 to 140 nm and is preferably about 80 to 120 nm, and in another preferable embodiment, an average particle diameter is about 20 to 50 nm, which is preferable from the viewpoint of knockdown efficiency. A particle diameter can be measured by, for example, a dynamic light scattering (DLS) method. In the specification of the present application, an average particle diameter of the lipid membrane structure means the number average particle diameter measured by DLS. The measurement by DLS can be performed by a general method using a commercially available DLS apparatus or the like.

A composition of an aqueous solvent (a dispersion medium) is not particularly limited, and examples thereof include a buffer solution such as a phosphate buffer solution, a citrate buffer solution, and a phosphate-buffered saline solution, a physiological saline solution, a medium for cell culture, and the like. These aqueous solvents (dispersion media) can stably disperse a lipid membrane structure, but also monosaccharide sugars (aqueous solutions) such as glucose, galactose, mannose, fructose, inositol, ribose, and xylose sugar, disaccharides such as lactose, sucrose, cellobiose, trehalose, and maltose, trrisaccharides such as raffinose and merezinose, polysaccharides such as cyclodextrins, and sugar alcohols such as erythritol, xylitol, sorbitol, mannitol, and maltitol; polyhydric alcohols (aqueous solutions) such as glycerin, diglycerin, polyglycerin, propylene glycol, polypropylene glycol, ethylene glycol, diethylene glycol, triethylene glycol, polyethylene glycol, ethylene glycol monoalkyl ether, diethylene glycol monoalkyl ether, and 1,3-butylene glycol; and the like may be added. In order to stably store a lipid membrane structure dispersed in an aqueous solvent for a long period of time, it is desirable to eliminate an electrolyte in the aqueous solvent as much as possible from the viewpoint of physical stability such as aggregation inhibition. In addition, from the viewpoint of chemical stability of a lipid, it is desirable to set a pH of the aqueous solvent from weakly acidic to near neutral (about pH 3.0 to 8.0) and/or to remove dissolved oxygen by nitrogen bubbling or the like.

In a case where the obtained aqueous dispersion of a lipid membrane structure is freeze-dried or spray-dried, for example, in some cases, stability can be improved by using sugars (aqueous solutions) such as monosaccharides such as glucose, galactose, mannose, fructose, inositol, ribose, and xylose sugars; disaccharides such as lactose, sucrose, cellobiose, trehalose, and maltose; trisaccharides such as raffinose and merezinose; polysaccharides such as cyclodextrins; sugar alcohols such as erythritol, xylitol, sorbitol, mannitol, and maltitol; and the like. In addition, in a case where the aqueous dispersion is frozen, for example, in some cases, stability can be improved by using the above-described sugars; or polyhydric alcohols (aqueous solutions) such as glycerin, diglycerin, polyglycerin, propylene glycol, polypropylene glycol, ethylene glycol, diethylene glycol, triethylene glycol, polyethylene glycol, ethylene glycol monoalkyl ether, diethylene glycol monoalkyl ether, and 1,3-butylene glycol.

Other substances can be sealed in the lipid membrane structure of the present invention as long as the functions of the siRNA are not inhibited. The types of substance that can be sealed in are not particularly limited, but active ingredients of any medicine such as an antitumor agent, an anti-inflammatory agent, an antibacterial agent, and an antiviral agent; and any substances such as saccharides, peptides, nucleic acids, low-molecular-weight compounds, and metal compounds can be sealed in. Examples of nucleic acids include a nucleic acid containing a gene, and more specifically, examples thereof include a gene incorporated in a plasmid, but examples are not limited to this specific aspect.

Patent Literature 6 specifically discloses a method for synthesizing a lipid compound containing YSK12; a method for preparing a lipid membrane structure using the lipid compound; and a gene expression inhibitory effect on THP-1 cells (a human monocyte line) and a gene expression inhibitory effect on Jurkat cells (a human T cell line) in the obtained lipid membrane structure. The entire disclosures of Patent Literature 6 are incorporated in the disclosures of the present specification by reference.

EXAMPLES

Hereinafter, the present invention will be further specifically described with reference to examples, but the scope of the present invention is not limited to the following examples.

Example 1

The lipid compound of the present invention was synthesized according to the following scheme. In a case where a hydrophobic scaffold is the same as that of YSK12 (Patent Literature 6), that is, in a case where a lipid in which c in General Formula (A) is 0 is synthesized, a linoleic acid (a compound A) was used as a starting material. A linoleic acid was reduced with lithium aluminum hydride (a compound B), activated by mesylating a hydroxyl group (a compound C), and brominated by the action of magnesium bromide (a compound D). Two linoleic-acid-derived hydrophobic scaffolds were linked by performing the Grignard reaction using 6-valerolactone as a substrate (a compound E). In a case where a tertiary amino group was directly bonded to a hydrocarbon chain, a primary hydroxyl group was activated through tosylation (a compound F), and the amino group was introduced by a nucleophilic substitution reaction.

Meanwhile, in a case where a tertiary amino group is bonded via an ester bond, an amino acid was linked to a primary hydroxyl group through dehydration condensation. For synthesis of a lipid containing an ester bond in the hydrophobic scaffold, for example, a lipid which contains an ester bond in $R^1$ and $R^2$ and in which c in General Formula (A) is 1, a substance (a compound G) in which hydrogen atoms bonded to both carbon atoms at both ends of a linear alkane (having 6 to 10 carbon atoms) was substituted by a bromine atom and a hydroxyl group one by one was used as a starting material. A hydroxyl group was protected by tert-butyldimethylsilyl etherification (a example, a lipid which contains an ester bond in $R^1$ and $R^2$ and in which c in General Formula (A) is 1, a substance (a compound G) in which hydrogen atoms bonded to both carbon atoms at both ends of a linear alkane (having 6 to 10 carbon atoms) was substituted by a bromine atom and a hydroxyl group one by one was used as a starting material. A hydroxyl group was protected by tert-butyldimethylsilyl etherification (a compound H), and two molecules were linked by the Grignard reaction (a compound I) as described above. As in the above description, after introducing a tertiary amino group directly into a primary hydroxyl group or via an ester bond (compounds J and M), a silyl ether was deprotected (compounds K and N), and optional linear fatty acids were linked thorough dehydration condensation.

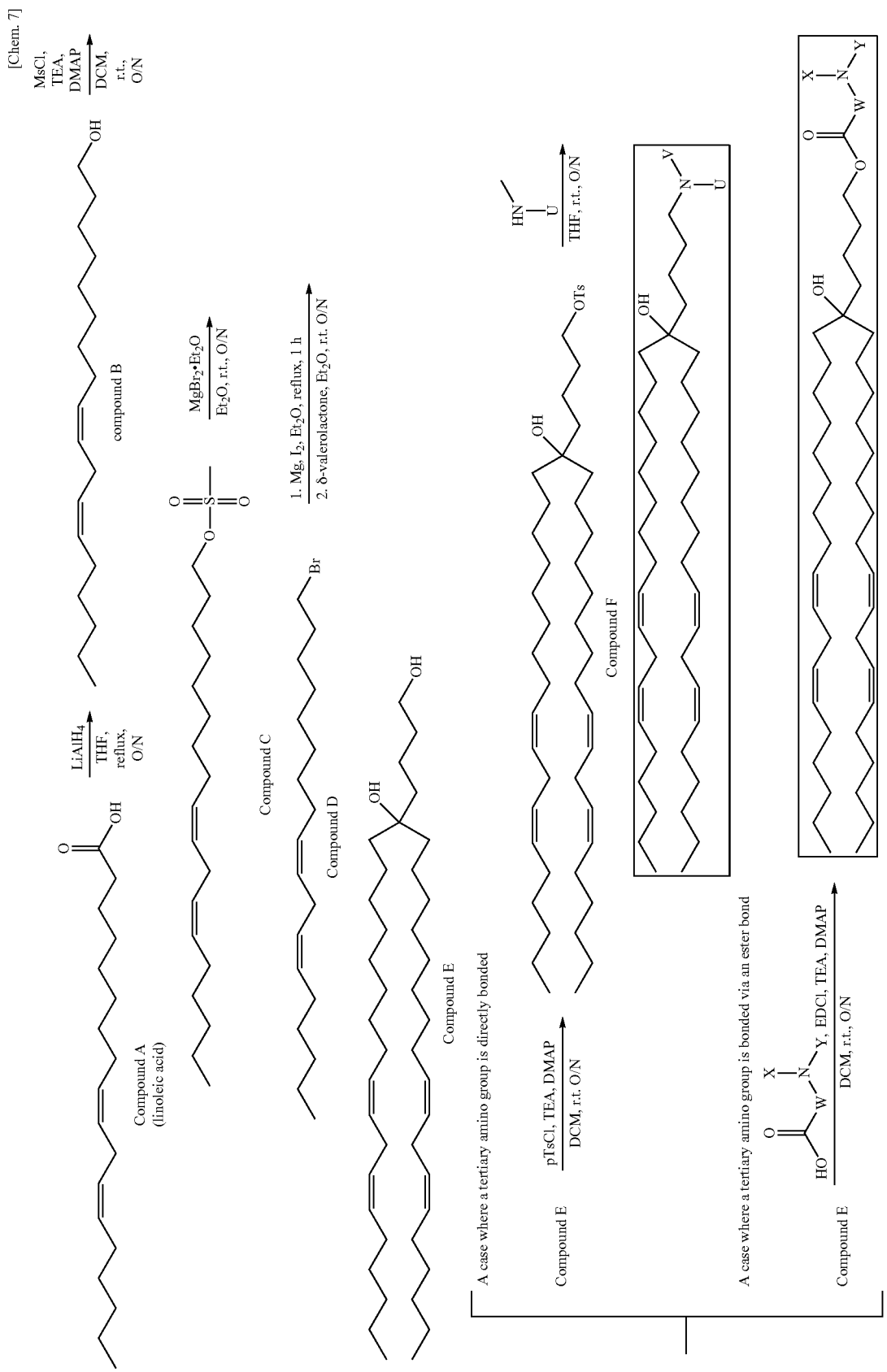

[Chem. 8]
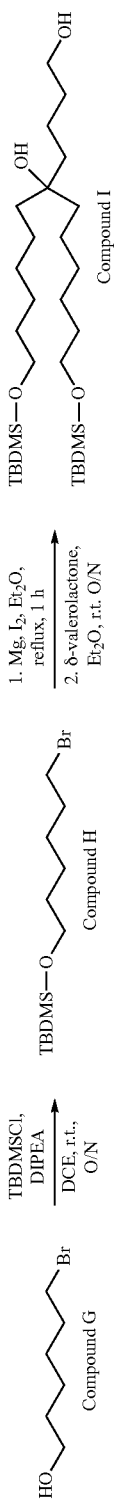
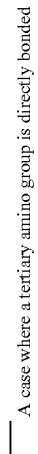
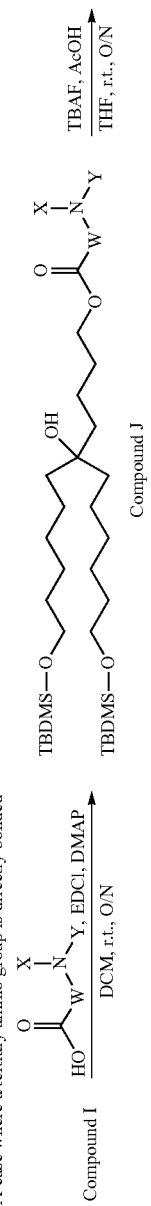
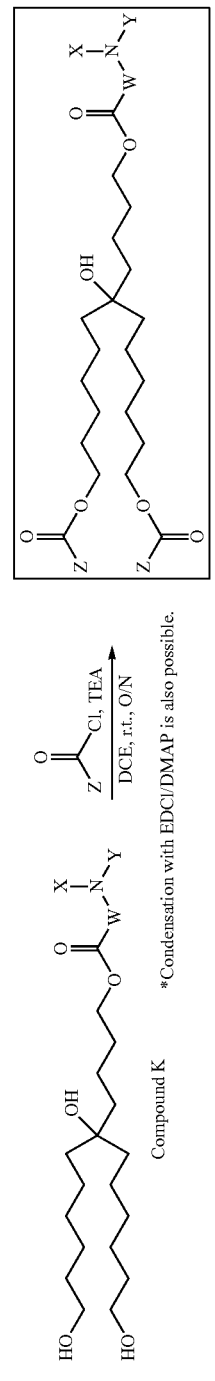
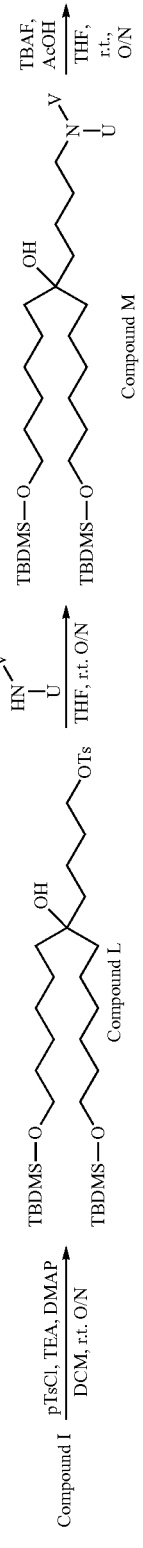
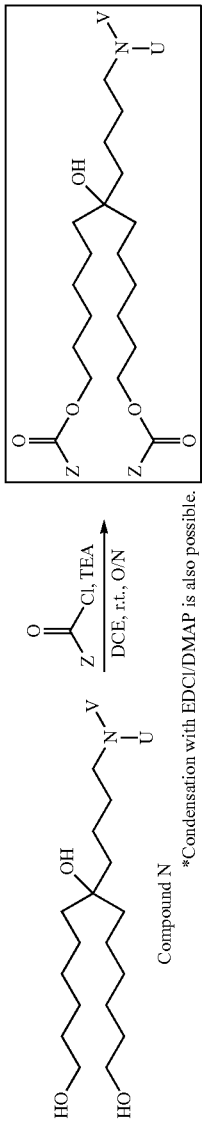

In the following examples, the nomenclature of lipid compounds is denoted as "Cationic Lipid (CL)-hydrophilic site number-hydrophobic scaffold 2 number-hydrophobic scaffold 1 number" according to the following partial structure. For example, YSK12 disclosed in Patent Literature 6 is denoted as "CL1A6."

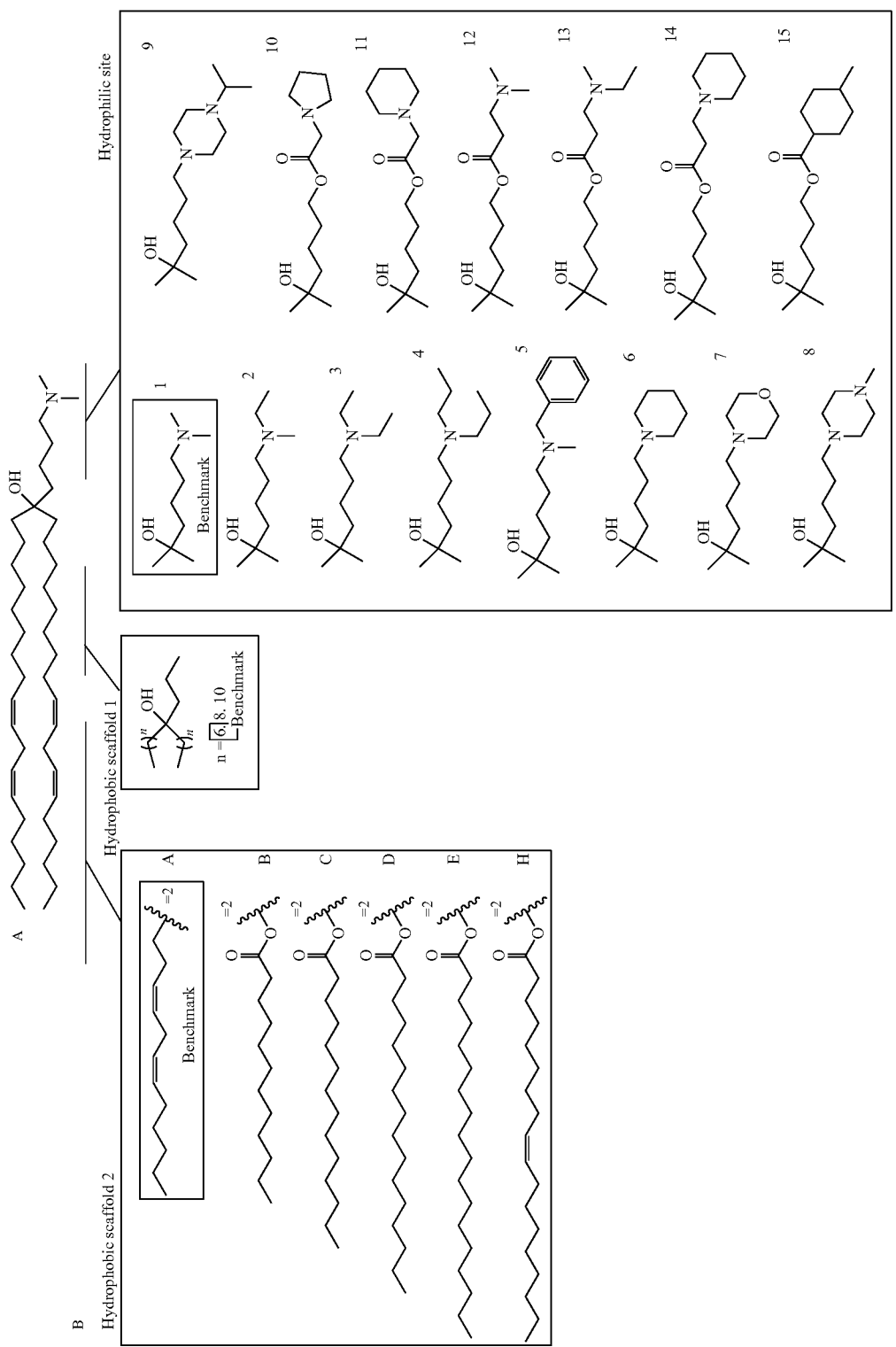

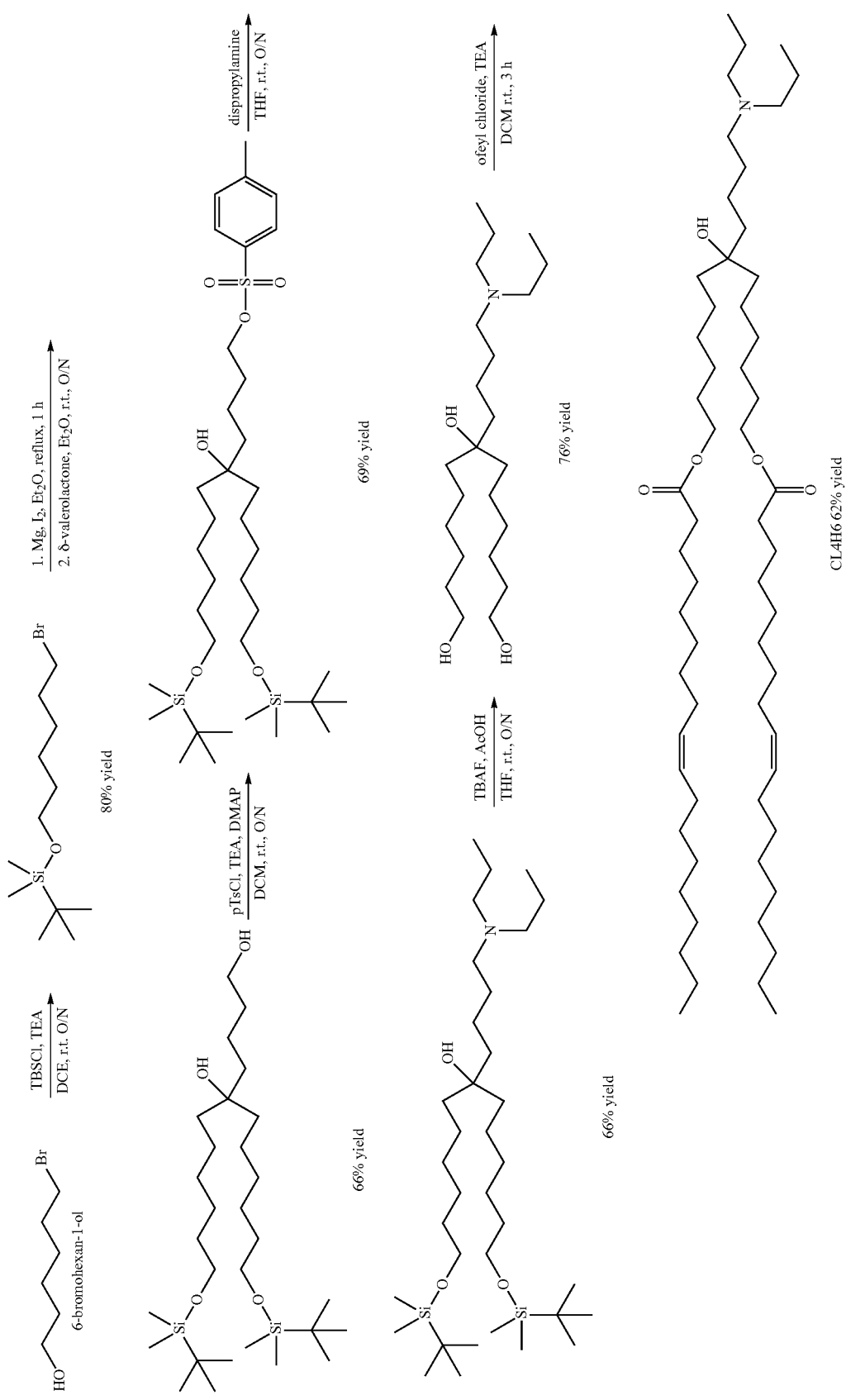

(1) ((6-Bromohexyl)oxy)(tert-butyl)dimethylsilane 20.0 g (110.5 mmol) of 6-bromohexan-1-ol was dissolved in 150 mL of 1,2-dichloroethane and cooled to 4° C. After adding 18.0 g (120 mmol) of tert-butyldimethylchlorosilane (TBSCl), 19.5 mL (140 mmol) of triethylamine (TEA) was added dropwise thereto, and stirred overnight at room temperature. The solvent was distilled off using a rotary evaporator, 300 mL of hexane was added and suspended, the insoluble matter was removed by Celite filtration, and thereby a crude product was obtained. The crude product was purified by subjecting it to silica gel chromatography {elution solvent; hexane:ethyl acetate (continuous gradient)}, and thereby 26.0 g (88.0 mmol) of ((6-bromohexyl)oxy)(tert-butyl)dimethylsilane was obtained as a colorless oil. The yield was 80%.

$^1$H NMR: 400 MHz δ=0.05 (s, 6H), 0.89 (s, 9H), 1.31-1.54 (m, 6H), 1.86 (m, 2H), 3.40 (t, 2H), 3.96 (t, 2H).

(2) 11-((Tert-butyldimethylsilyl)oxy)-5-(6-((tert-butyldimethylsilyl)oxy)hexyl)undecane-1,5-diol 1.2 g (4.06 mmol) of ((6-bromohexyl)oxy)(tert-butyl)dimethylsilane was dissolved in 4 mL of diethyl ether, 2.43 g (100 mmol) of shaved magnesium was added thereto, and then an iodine primary fragment was added. The mixture was allowed to stand at room temperature for 10 minutes, stirred while heating to 40° C. in an oil bath, and 24.8 g (83.94 mmol) of ((6-bromohexyl)oxy)(tert-butyl)dimethylsilane dissolved in 21 mL of diethyl ether was added dropwise. The mixture was reacted at 40° C. for 2 hours and then cooled to 4° C. Subsequently, 3.67 mL (39.6 mmol) of 6-valerolactone was added and allowed to react overnight at room temperature. Next, the resultant was cooled to 4° C., and 5% sulfuric acid was added dropwise to dissolve the residual magnesium. The mixture was diluted with diethyl ether, and the organic layer was separated and washed with water and saturated saline. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; hexane:ethyl acetate (continuous gradient)}, and thereby 14.0 g (26.3 mmol) of 11-((tert-butyldimethylsilyl)oxy)-5-(6-((tert-butyldimethylsilyl)oxy)hexyl)undecane-1,5-diol was obtained as a colorless oil. The yield based on 6-valerolactone was 66%.

$^1$H NMR; 400 MHz δ=0.05 (s, 12H), 0.89 (s, 18H), 1.25-1.56 (m, 26H), 3.59 (t, 4H), 3.65 (t, 2H).

(3) 11-((Tert-butyldimethylsilyl)oxy)-5-(6-((tert-butyldimethylsilyl)oxy)hexyl)-5-hydroxyundecyl 4-methylbenzenesulfonate 14.0 g (26.3 mmol) of 11-((tert-butyldimethylsilyl)oxy)-5-(6-((tert-butyldimethylsilyl)oxy)hexyl)undecane-1,5-diol was dissolved in 50 mL of dichloromethane, and 321 mg (2.63 mmol) of DMAP (N,N-dimethyl-4-aminopyridine) and 5.50 mL (39.5 mmol) of diisopropylethylamine (DIPEA) were added thereto and cooled to 4° C. Subsequently, 6.02 g (31.6 mmol) of p-toluenesulfonyl chloride (pTsCl) was gradually added, followed by reaction at room temperature overnight. The solvent was distilled off using a rotary evaporator, the residue was suspended in ethyl acetate, and separated and washed with water and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; hexane:ethyl acetate (continuous gradient)}, and thereby 12.4 g (28.0 mmol) of 11-((tert-butyldimethylsilyl)oxy)-5-(6-((tert-butyldimethylsilyl)oxy)hexyl)-5-hydroxyundecyl 4-methylbenzenesulfonate was obtained as a colorless oil. The yield was 69%.

(4) 11-(4-(Diisopropylamino)butyl)-2,2,3,3,19,19,20,20-octamethyl-4,18-dioxa-3,19-disilahenicosan-11-ol 30 mL of THF was added to 12.4 g (18.0 mmol) of 11-((tert-butyldimethylsilyl)oxy)-5-(6-((tert-butyldimethylsilyl)oxy)hexyl)-5-hydroxyundecyl 4-methylbenzenesulfonate, and cooled to 4° C. Subsequently, 7.38 mL (54.0 mmol) of dipropylamine was added, followed by reaction at room temperature for 11 days. The solvent was distilled off using a rotary evaporator, and then the residue was suspended in ethyl acetate, and separated and washed with a 0.5 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; dichloromethane:methanol (continuous gradient)}, and thereby 7.27 g (11.8 mmol) of 11-(4-(diisopropylamino)butyl)-2,2,3,3,19,19,20,20-octamethyl-4,18-dioxa-3,19-disilahenicosan-11-ol was obtained as a pale yellow oil. The yield was 66%.

$^1$H NMR: 400 MHz δ=0.05 (s, 12H), 0.89 (s, 18H), 1.24-1.64 (m, 30H), 2.30-2.43 (m, 6H), 3.58 (t, 4H).

(5) 7-(4-(Diisopropylamino)butyl)tridecane-1,7,13-triol

A THF solution of 2.23 mL (39 mmol) of an acetic acid and 26 mL of 1.0 M tetrabutylammonium fluoride was added to 7.27 g (11.8 mmol) of 11-(4-(diisopropylamino)butyl)-2,2,3,3,19,19,20,20-octamethyl-4,18-dioxa-3,19-disilahenicosan-11-ol, and the mixture was allowed to react overnight at room temperature. The solvent was distilled off using a rotary evaporator, and then purified by subjecting it to reverse-phase silica gel chromatography {elution solvent; water (0.1% trifluoroacetic acid):acetonitrile (0.1% trifluoroacetic acid) (continuous gradient)}, and thereby 3.43 g (8.85 mmol) of 7-(4-(diisopropylamino)butyl)tridecane-1,7,13-triol was obtained as a pale yellow oil. The yield was 75%.

(6) 7-(4-(Diisopropylamino)butyl)-7-hydroxytridecane-1,13-diyl dioleate (CL4H6)

388 mg (1.0 mmol) of 7-(4-(diisopropylamino)butyl)tridecane-1,7,13-triol was dissolved in 5 mL of dichloromethane, thereafter, 900 mg (3.0 mmol) of oleyl chloride was added thereto and then cooled to 4° C. 697 μL (5.0 mmol) of TEA was added dropwise and reacted at room temperature for 3 hours. After the solvent was distilled off using a rotary evaporator, the residue was suspended in ethyl acetate, and insoluble matter was removed by filtration. The filtrate was separated and washed with a 0.5 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; dichloromethane:methanol (continuous gradient)}, and thereby 570 mg (0.622 mmol) of 7-(4-(diisopropylamino)butyl)-7-hydroxytridecane-1,13-diyl dioleate (CL4H6) was obtained as a pale yellow oil. The yield was 62%.

$^1$H NMR; 400 MHz δ=0.88 (m, 12H), 1.18-1.71 (m, 74H), 2.01 (m, 8H), 2.24-2.30 (t, 4H), 2.32-2.42 (m, 6H), 4.04 (t, 4H), 5.32 (m, 4H).

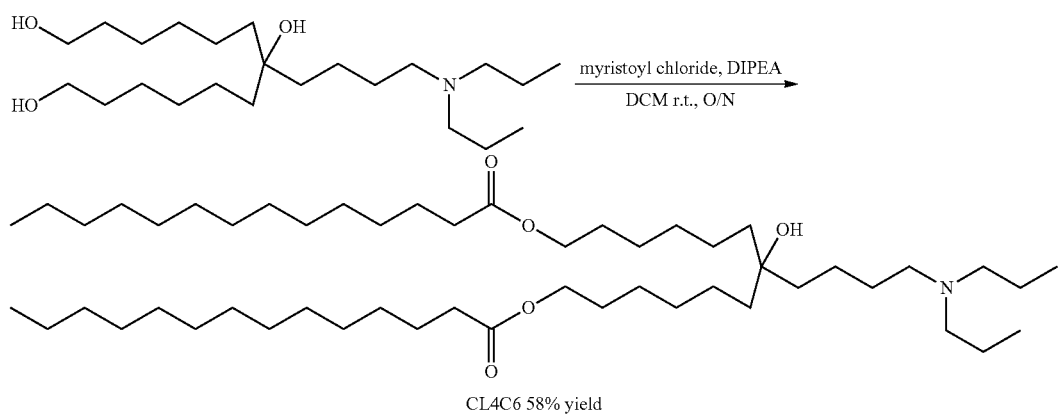

CL4C6 58% yield

(7) 7-(4-(Diisopropylamino)butyl)-7-hydroxytridecane-1,13-diyl ditetradecanoate (CL4C6)

77.5 mg (0.20 mmol) of 7-(4-(diisopropylamino)butyl) tridecane-1,7,13-triol was dissolved in 1 mL of dichloromethane, thereafter, 197 mg (0.80 mmol) of myristoyl chloride was added thereto and then cooled to 4° C. 205 µL (1.2 mmol) of DIPEA was added dropwise and allowed to react overnight at room temperature. After the solvent was distilled off using a rotary evaporator, the residue was suspended in ethyl acetate, and insoluble matter was removed by filtration. The filtrate was separated and washed with a 0.2 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; dichloromethane:methanol (continuous gradient)}, and thereby 93 mg (0.115 mmol) of 7-(4-(diisopropylamino)butyl)-7-hydroxytridecane-1,13-diyl ditetradecanoate (CL4C6) was obtained as a pale yellow oil. The yield was 58%.

$^1$H NMR; 400 MHz δ=0.88 (m, 12H), 1.18-1.68 (m, 74H), 2.27 (t, 4H), 2.42-2.53 (br, 6H), 4.04 (t, 4H).

(8) 7-(4-(Diisopropylamino)butyl)-7-hydroxytridecane-1,13-diyl dipalmitate (CL4D6)

77.5 mg (0.20 mmol) of 7-(4-(diisopropylamino)butyl) tridecane-1,7,13-triol was dissolved in 1 mL of dichloromethane, thereafter, 220 mg (0.80 mmol) of palmitoyl chloride was added thereto and then cooled to 4° C. 205 µL (1.2 mmol) of DIPEA was added dropwise and allowed to react overnight at room temperature. After the solvent was distilled off using a rotary evaporator, the residue was suspended in ethyl acetate, and insoluble matter was removed by filtration. The filtrate was separated and washed with a 0.2 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; dichloromethane:methanol (continuous gradient)}, and thereby 143 mg (0.164 mmol) of 7-(4-(diisopropylamino)butyl)-7-hydroxytridecane-1,13-diyl dipalmitate (CL4D6) was obtained as a pale yellow oil. The yield was 82%.

$^1$H NMR; 400 MHz δ=0.88 (m, 12H), 1.18-1.68 (m, 82H), 2.27 (t, 4H), 2.45-2.53 (br, 6H), 4.04 (t, 4H).

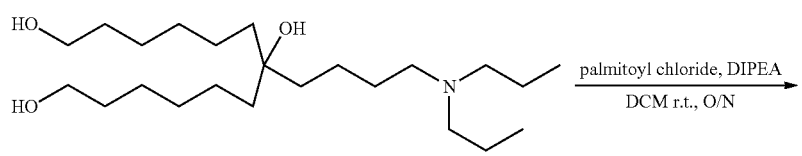

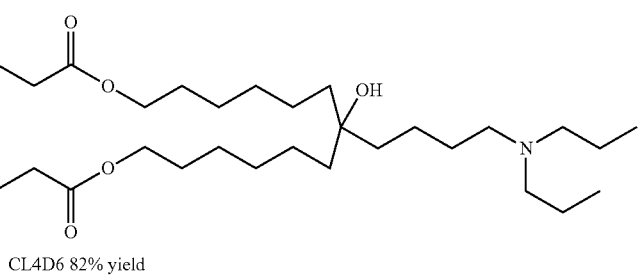

CL4D6 82% yield

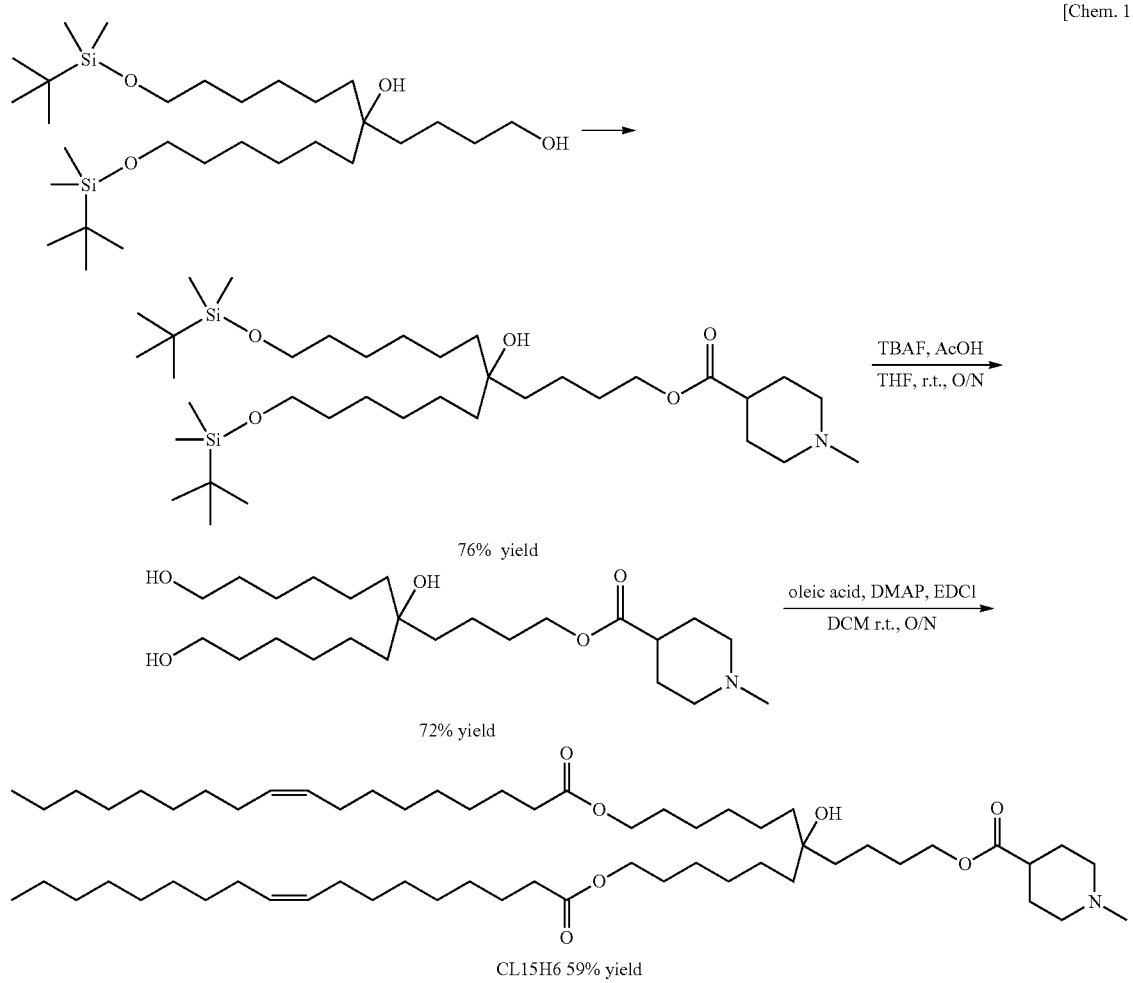

[Chem. 13]

CL15H6 59% yield (9) 11-((Tert-butyldimethylsilyl)oxy)-5-(6-((tert-butyldimethylsilyl)oxy)hexyl)-5-hydroxyundecyl 1-methylpiperidine-4-carbooxylate 5.33 g (10.0 mmol) of 11-((tert-butyldimethylsilyl)oxy)-5-(6-((tert-butyldimethylsilyl)oxy)hexyl)undecane-1,5-diol was dissolved in 50 mL of dichloromethane, and 122 mg (1.0 mmol) of DMAP and 2.16 g (12.0 mmol) of 1-methylpiperidine-4-carbooxyacid hydrochloride were added thereto. Subsequently, 2.49 g (13.0 mmol) of EDCI was gradually added, followed by reaction at room temperature overnight. After the solvent was distilled off using a rotary evaporator, the residue was suspended in ethyl acetate, and insoluble matter was removed by filtration. The filtrate was separated and washed with a 0.5 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; dichloromethane:methanol (continuous gradient)}, and thereby 5.01 g (7.61 mmol) of 11-((tert-butyldimethylsilyl)oxy)-5-(6-((tert-butyldimethylsilyl)oxy)hexyl)-5-hydroxyundecyl 1-methylpiperidine-4-carbooxylate was obtained as a colorless oil. The yield was 76%.

$^1$H NMR; 400 MHz δ=0.05 (s, 12H), 0.89 (s, 18H), 1.25-2.01 (m, 26H), 2.23 (br.s, 4H), 2.78 (m, 2H), 3.58 (t, 4H), 4.08 (t, 2H).

(10) 5,11-Dihydroxy 5-(6-hydroxyhexyl)undecyl 1-methylpiperidine-4-carbooxylate

A THF solution of 1.43 mL (25 mmol) of an acetic acid and 20 mL of 1.0 M tetrabutylammonium fluoride was added to 5.01 g (7.61 mmol) of 11-((tert-butyldimethylsilyl)oxy)-5-(6-((tert-butyldimethylsilyl)oxy)hexyl)-5-hydroxyundecyl 1-methylpiperidine-4-carbooxylate, and the mixture was allowed to react overnight at room temperature. The solvent was distilled off using a rotary evaporator, and then purified by subjecting it to reverse-phase silica gel chromatography {elution solvent; water (0.1% trifluoroacetic acid):acetonitrile (0.1% trifluoroacetic acid) (continuous gradient)}, and thereby 2.34 g (5.45 mmol) of 5,11-dihydroxy 5-(6-hydroxyhexyl)undecyl 1-methylpiperidine-4-carbooxylate was obtained as a pale yellow oil. The yield was 72%.

$^1$H NMR; 400 MHz δ=1.25-1.45 (m, 20H), 1.52 (m, 4H), 1.62 (m, 2H), 1.86 (m, 2H), 2.05 (m, 2H), 2.50-2.70 (m, 6H), 3.16 (m, 2H), 3.53 (t, 4H), 4.11 (t, 2H).

(11) 7-Hydroxy 7-(4-((1-methylpiperidine-4-carbonyl)oxy)butyl)tridecane-1,13-diyl dioleate (CL15H6)

430 mg (1.00 mmol) of 5,11-dihydroxy 5-(6-hydroxyhexyl)undecyl 1-methylpiperidine-4-carbooxylate was dissolved in 10 mL of dichloromethane. Subsequently, 706 mg (2.50 mmol) of an oleic acid, 24.4 mg (0.20 mmol) of DMAP, and 671 mg (3.5 mmol) of EDCI were added and reacted at room temperature for 2 hours. After the solvent was distilled off using a rotary evaporator, the residue was suspended in ethyl acetate, and insoluble matter was removed by filtration. The filtrate was separated and washed with a 0.5 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; dichloromethane:methanol (continuous gradient)}, and thereby 569 mg (0.594 mmol) of 7-hydroxy 7-(4-((1-methylpiperidine-4-carbonyl)oxy)butyl)tridecane-1,13-diyl dioleate (CL15H6) was obtained as a pale yellow oil. The yield was 59%.

$^1$H NMR; 400 MHz) data δ=0.88 (t, 6H), 1.20-2.05 (m, 78H), 2.28 (m, 8H), 2.82 (m, 2H), 4.07 (m, 6H), 5.33 (m, 4H).

[Chem. 14]

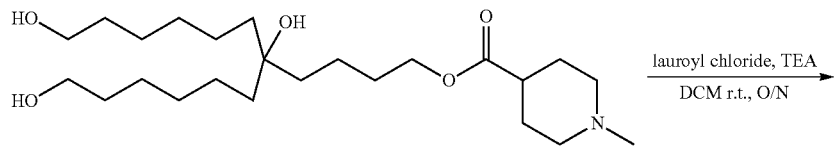

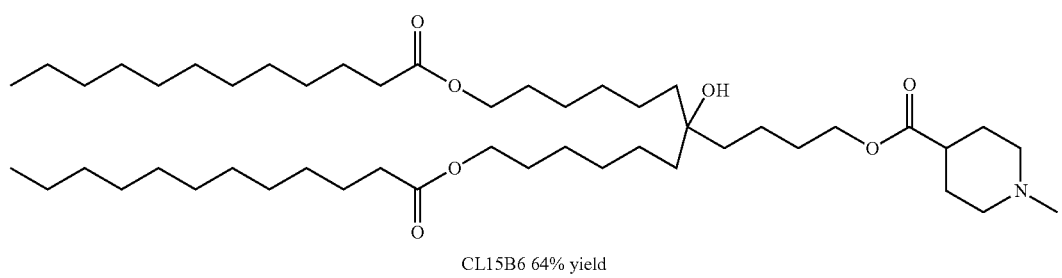

CL15B6 64% yield

(12) 7-Hydroxy 7-(4-((1-methylpiperidine-4-carbonyl)oxy)butyl)tridecane-1,13-diyl didodecanoate (CL15B6)

85.9 mg (0.20 mmol) of 5,11-dihydroxy 5-(6-hydroxyhexyl)undecyl 1-methylpiperidine-4-carbooxylate was dissolved in 1.5 mL of dichloromethane, and thereafter, 143 mg (0.60 mmol) of lauroyl chloride was added thereto and then cooled to 4° C. 139 μL (1.00 mmol) of TEA was added dropwise and reacted at room temperature overnight. After the solvent was distilled off using a rotary evaporator, the residue was suspended in ethyl acetate, and insoluble matter was removed by filtration. The filtrate was separated and washed with a 0.2 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; dichloromethane:methanol (continuous gradient)}, and thereby 101.2 mg (0.127 mmol) of 7-hydroxy 7-(4-((1-methylpiperidine-4-carbonyl)oxy)butyl)tridecane-1,13-diyl didodecanoate (CL15B6) was obtained as a pale yellow oil. The yield was 64%.

$^1$H NMR; 400 MHz δ=0.88 (t, 6H), 1.20-2.13 (m, 70H), 2.28 (m, 8H), 2.84 (m, 2H), 4.06 (m, 6H).

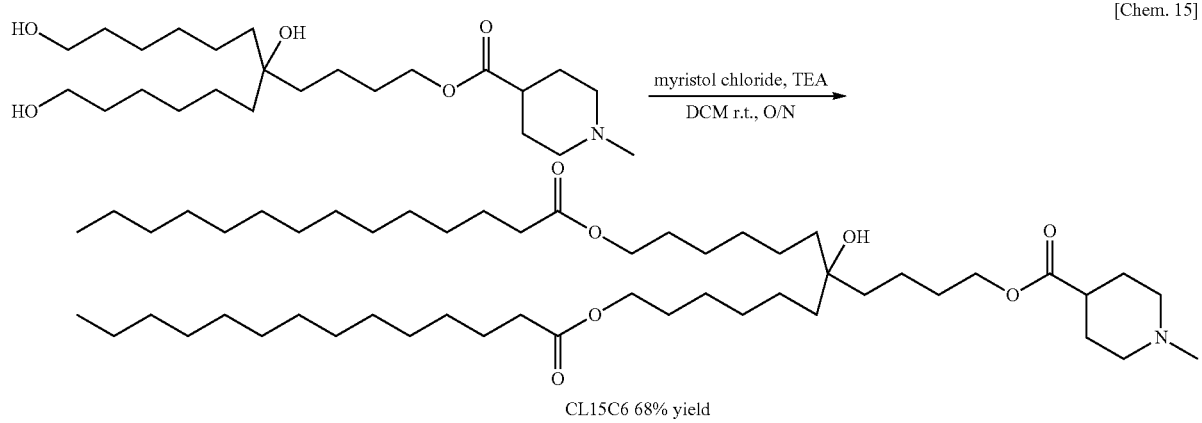

CL15C6 68% yield

(13) 7-Hydroxy 7-(4-((1-methylpiperidine-4-carbonyl)oxy)butyl)tridecane-1,13-diyl ditetradecanoate (CL15C6)

85.9 mg (0.20 mmol) of 5,11-dihydroxy 5-(6-hydroxyhexyl)undecyl 1-methylpiperidine-4-carbooxylate was dissolved in 1.5 mL of dichloromethane, and thereafter, 163 mg (0.60 mmol) of myristoyl chloride was added thereto and then cooled to 4° C. 139 µL (1.00 mmol) of TEA was added dropwise and reacted at room temperature overnight. After the solvent was distilled off using a rotary evaporator, the residue was suspended in ethyl acetate, and insoluble matter was removed by filtration. The filtrate was separated and washed with a 0.2 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; dichloromethane:methanol (continuous gradient)}, and thereby 116 mg (0.136 mmol) of 7-hydroxy 7-(4-((1-methylpiperidine-4-carbonyl)oxy)butyl)tridecane-1,13-diyl ditetradecanoate (CL15C6) was obtained as a pale yellow solid. The yield was 68%.

$^1$H NMR; 400 MHz δ=0.88 (t, 6H), 1.20-2.10 (m, 78H), 2.28 (m, 8H), 2.82 (m, 2H), 4.06 (m, 6H).

(14) 7-Hydroxy 7-(4-((1-methylpiperidine-4-carbonyl)oxy)butyl)tridecane-1,13-diyl dipalmitate (CL15D6)

85.9 mg (0.20 mmol) of 5,11-dihydroxy 5-(6-hydroxyhexyl)undecyl 1-methylpiperidine-4-carbooxylate was dissolved in 1.5 mL of dichloromethane, and thereafter, 181 mg (0.60 mmol) of palmitoyl chloride was added thereto and then cooled to 4° C. 139 µL (1.00 mmol) of TEA was added dropwise and reacted at room temperature overnight. After the solvent was distilled off using a rotary evaporator, the residue was suspended in ethyl acetate, and insoluble matter was removed by filtration. The filtrate was separated and washed with a 0.2 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; dichloromethane:methanol (continuous gradient)}, and thereby 114 mg (0.126 mmol) of 7-hydroxy 7-(4-((1-methylpiperidine-4-carbonyl)oxy)butyl)tridecane-1,13-diyl dipalmitate (CL15D6) was obtained as a pale yellow solid. The yield was 63%.

$^1$H NMR; 400 MHz δ=0.88 (t, 6H), 1.20-2.11 (m, 86H), 2.28 (m, 8H), 2.83 (m, 2H), 4.06 (m, 6H).

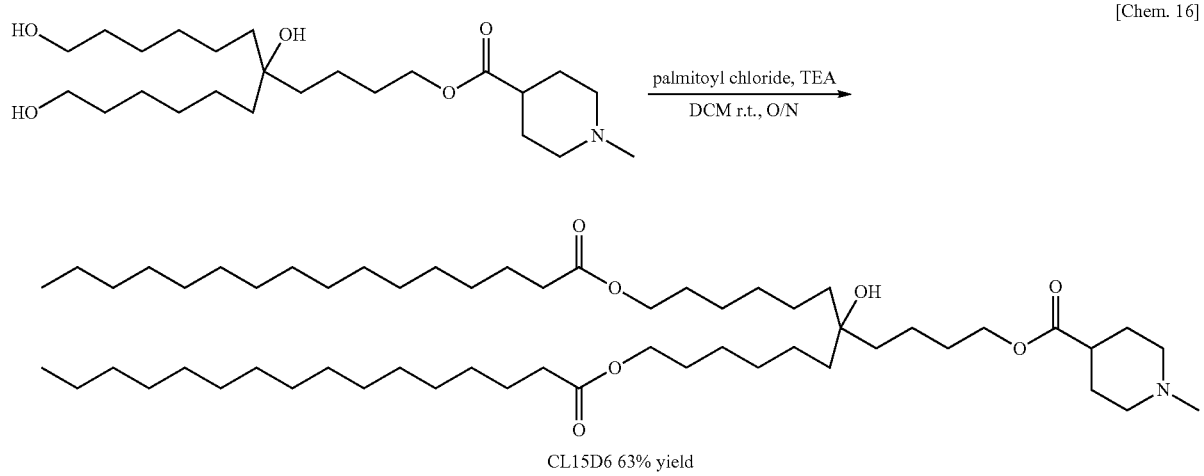

CL15D6 63% yield

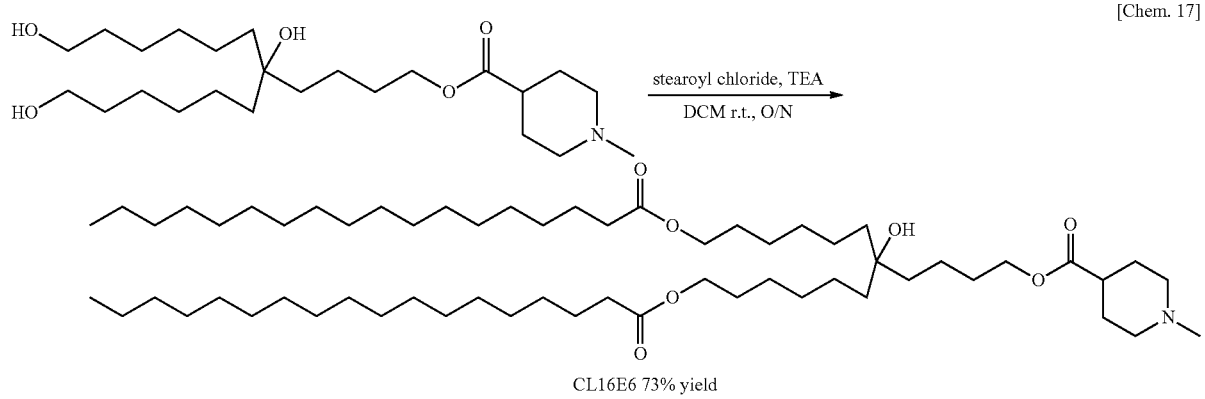

CL16E6 73% yield

(15) 7-Hydroxy 7-(4-((1-methylpiperidine-4-carbonyl)oxy)butyl)tridecane-1,13-diyl distearate (CL15E6)

85.9 mg (0.20 mmol) of 5,11-dihydroxy 5-(6-hydroxyhexyl)undecyl 1-methylpiperidine-4-carbooxylate was dissolved in 1.0 mL of dichloromethane, and thereafter, 181 mg (0.80 mmol) of stearoyl chloride was added thereto and then cooled to 4° C. 139 μL (1.00 mmol) of TEA was added dropwise and reacted at room temperature overnight. After the solvent was distilled off using a rotary evaporator, the residue was suspended in ethyl acetate, and insoluble matter was removed by filtration. The filtrate was separated and washed with a 0.2 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; dichloromethane:methanol (continuous gradient)}, and thereby 141 mg (0.146 mmol) of 7-hydroxy 7-(4-((1-methylpiperidine-4-carbonyl)oxy)butyl)tridecane-1,13-diyl distearate (CL15E6) was obtained as a pale yellow solid. The yield was 73%.

$^1$H NMR; 400 MHz δ=0.88 (t, 6H), 1.20-2.10 (m, 94H), 2.28 (m, 8H), 2.83 (m, 2H), 4.06 (m, 6H).

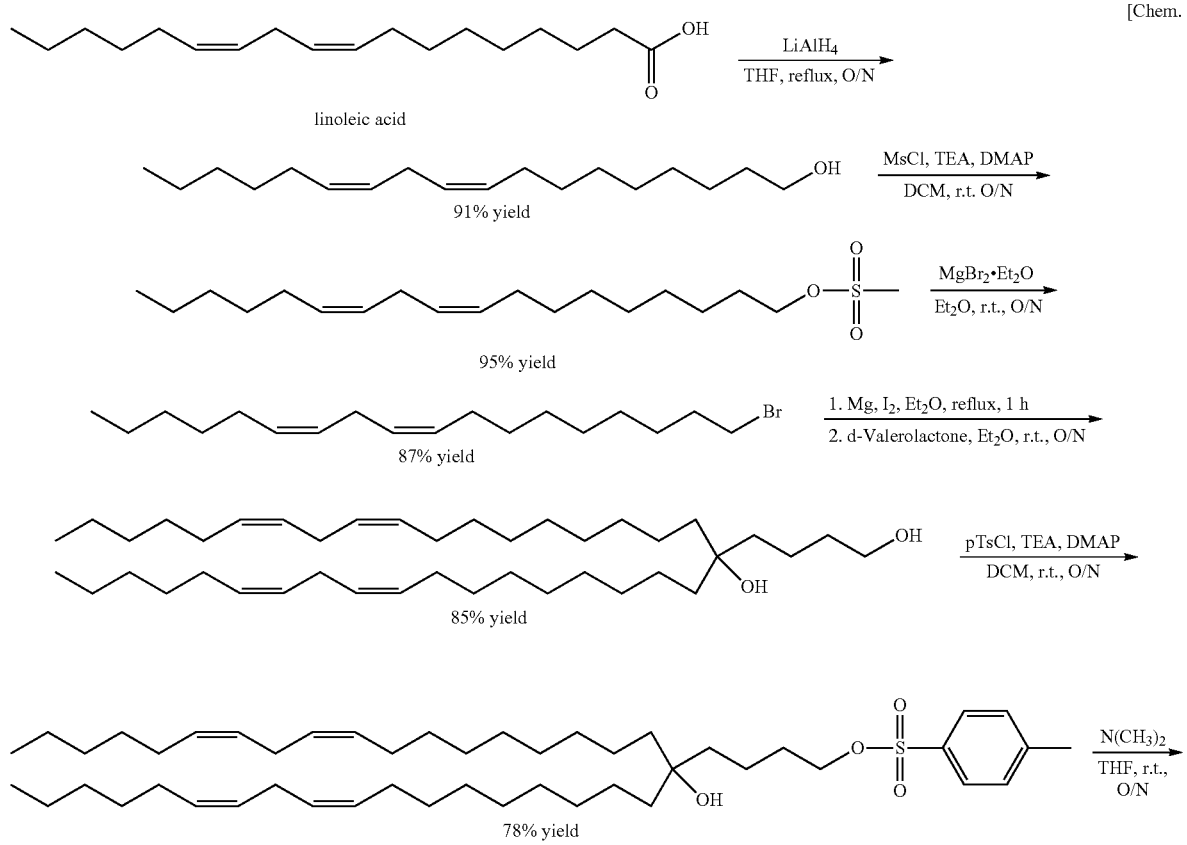

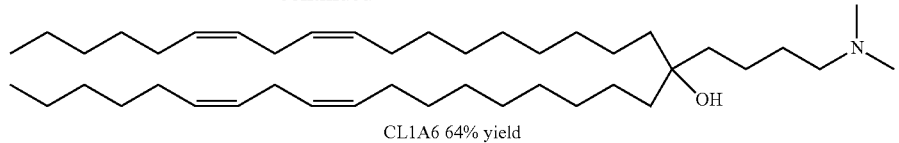

CL1A6 64% yield

(16) (9z,12z)-Octadien-1-ol 2.73 g (72 mmol) of lithium aluminum hydride was suspended in 190 mL of tetrahydrofuran (THF) cooled to 4° C. 10 g (36 mmol) of linoleic acid was added dropwise thereto and stirred for 10 minutes. Thereafter, reflux was performed overnight while performing heating with an oil bath. After cooling the resultant, 100 mL of a 1 mol/L aqueous sodium hydroxide solution was added, and reaction was stopped. Next, 100 mL of ethyl acetate was added for dilution, followed by filtration, and the filtrate was washed using a saturated aqueous sodium hydrogen carbonate solution. Subsequently, the organic layer was recovered and dehydrated by adding anhydrous sodium sulfate thereto. After filtering the resultant, the solvent was distilled off using a rotary evaporator to obtain a crude product. The crude product was purified by subjecting it to silica gel chromatography {elution solvent; hexane:ethyl acetate (continuous gradient)}, and thereby 8.68 g (32.6 mmol) of (9z,12z)-octadien-1-ol was obtained as a colorless oil. The yield was 91%.

$^1$H NMR; 500 MHz δ=0.88 (t, 3H), 1.25-1.36 (m, 16H), 1.53-1.58 (m, 2H), 2.02-2.06 (m, 4H), 2.76 (t, 2H), 3.62 (t, 2H), 5.29-5.40 (m, 4H).

(17) (9z, 12z)-Octadiene-1-methanesulfonate 8.68 g (32.6 mmol) of (9z, 12z)-octadien-1-ol was dissolved in 100 mL of dichloromethane, and then 366 mg (3.26 mmol) of N,N-dimethyl-4-aminopyridine (DMAP) and 6.8 mL (48.9 mmol) of triethylamine (TEA) were added thereto. Subsequently, using a dropping funnel, 3.03 mL (39.1 mmol) of methanesulfonyl chloride (MsCl) diluted with 50 mL of dichloromethane was added dropwise and stirred overnight at room temperature. The reaction solution was recovered and washed using a saturated aqueous sodium hydrogen carbonate solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; hexane:ethyl acetate (continuous gradient)}, and thereby 10.64 g (30.9 mmol) of (9z,12z)-octadiene-1-methanesulfonate was obtained as a colorless oil. The yield was 95%.

$^1$H NMR; 500 MHz δ=0.88 (t, 3H), 1.06-1.18 (m, 18H), 1.70-1.90 (m, 2H), 2.00-2.19 (m, 4H), 2.79 (t, 2H), 3.06 (s, 3H), 4.20 (t, 2H), 5.21-5.42 (m, 4H).

(18) 18-Bromo-octadeca-(6z,9z)-diene 10.64 g of (9z, 12z)-octadiene-1-methanesulfonate was dissolved in 140 mL of diethyl ether, and then 16.0 g (61.8 mmol) of magnesium bromide ethyl etherate was added thereto, and the mixture was stirred overnight at room temperature. The reaction solution was recovered and washed using 100 mL of a saturated aqueous sodium hydrogen carbonate solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; hexane:ethyl acetate (continuous gradient)}, and thereby 8.85 g (26.9 mmol) of 18-bromo-octadeca-(6z,9z)-diene was obtained as a colorless oil. The yield was 87%.

$^1$H NMR; 500 MHz δ=0.88 (t, 3H), 1.27-1.46 (m, 18H), 1.80-1.88 (m, 2H), 2.00-2.09 (m, 4H), 2.77 (t, 2H), 3.40 (t, 2H), 4.20 (d, 2H), 5.29-5.41 (m, 4H).

(19) 4-[(9z,12z)-Octadienyl]-(13z,16z)-tricosadiene-1,4-diol 50 g (1.52 mmol) of 18-bromo-octadeca-(6z,9z)-diene was dissolved in 1.5 mL of diethyl ether, 609 mg (25.1 mmol) of shaved magnesium was added thereto, and then an iodine primary fragment was added. The mixture was allowed to stand at room temperature for 10 minutes, stirred while heating to 45° C. in an oil bath, and 5.0 g (15.2 mmol) of 18-bromo-octadeca-(6z,9z)-diene dissolved in 6 mL of diethyl ether was added dropwise thereto. The mixture was reacted at 45° C. for 1 hour and then cooled to room temperature. Subsequently, 300 μL (3.23 mmol) of 6-valerolactone was added and allowed to react for 1 hour at room temperature. Next, the resultant was cooled to 4° C., followed by filtration, and then the filtrate was washed with a saturated aqueous sodium hydrogen carbonate solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; hexane: ethyl acetate (continuous gradient)}, and thereby 1.64 g (2.73 mmol) of 4-[(9z,12z)-octadienyl]-(13z,16z)-tricosadiene-1,4-diol was obtained as a colorless oil. The yield based on δ-valerolactone was 85%.

$^1$H NMR; 500 MHz δ=0.88 (t, 6H), 1.25-1.1.46 (m, 46H), 2.02-2.06 (m, 8H), 2.77 (t, 4H), 3.66 (t, 2H), 5.30-5.40 (m, 8H).

(20) 4-[(9z, 12z)-Octadienyl]-1-p-toluenesulfonyl-(13z, 16z)-tricosadien-4-ol 301 mg (0.50 mmol) of 4-[(9z,12z)-octadecadienyl]-(13z, 16z)-tricosadiene-1,4-diol was dissolved in 5.0 mL of dichloromethane, 6.11 mg (0.05 mmol) of DMAP and 83.6 μL (0.60 mmol) of TEA were added thereto, and thereafter, 95.3 mg (0.50 mmol) of p-toluenesulfonyl chloride (pTsCl) was added, and the mixture was stirred at room temperature overnight. Subsequently, silica gel was added to the reaction solution, and the solvent was distilled off using a rotary evaporator. Thereafter, the crude product was purified by subjecting it to silica gel chromatography {elution solvent; hexane:ethyl acetate (continuous gradient)}, and thereby 293 mg (0.39 mmol) was obtained as a colorless oil. The yield was 78%.

¹H NMR; 500 MHz δ=0.88 (t, 3H), 1.25-1.49 (m, 46H), 2.03-2.05 (m, 8H), 2.44 (s, 3H), 2.77 (t, 4H), 4.03 (t, 2H), 5.31-5.39 (m, 8H), 7.34 (d, 2H), 7.78 (d, 2H).

(21) 1-N,N-Dimethylamino-4-[(9z, 12z)-octadecadienyl]-(13z,16z)-tricosadien-4-ol 10 mL of a THF solution of 2.0 M dimethylamine was added to 293 mg (0.39 mmol) of 4-[(9z,12z)-octadienyl]-1-p-toluenesulfonyl-(13z,16z)-tricosadien-4-ol, and the reaction was allowed to proceed overnight at room temperature. After the solvent was distilled off using a rotary evaporator, 100 mL of dichloromethane was added, and the mixture was washed with 100 mL of a 0.1 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 155 mg (0.25 mmol) was obtained as a pale yellow oil. The yield was 64%.

¹H NMR; 500 MHz δ=0.87 (t, 6H), 1.23-1.40 (m, 46H), 2.02-2.07 (m, 8H), 2.26 (s, 6H), 2.33 (t, 2H), 2.77 (t, 4H), 5.31-5.39 (m, 8H).

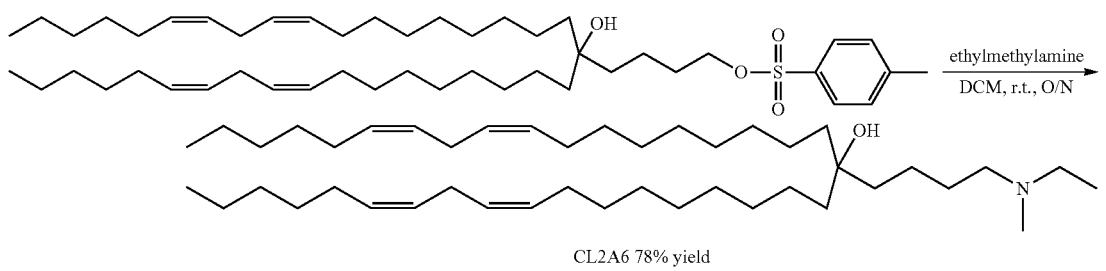

[Chem. 19]

CL2A6 78% yield

(22) (6Z,9Z,28Z,31Z)-19-(4-(Ethyl(methyl)amino)butyl)heptatriconta-6,9,28,31-tetraen-19-ol 650 mg (0.86 mmol) of 4-[(9z, 12z)-octadienyl]-1-p-toluenesulfonyl-(13z, 16z)-tricosadien-4-ol was dissolved in 4 mL of dichloromethane, 0.86 mL (10 mmol) of ethylmethylamine was added thereto, and the mixture was reacted at 40° C. for 3 days. After the solvent was distilled off using a rotary evaporator, 5 mL of ethyl acetate was added, and the mixture was washed with 5 mL of a 0.1 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 432 mg (0.673 mmol) was obtained as a pale yellow oil. The yield was 78%.

¹H NMR; 400 MHz δ=0.87 (t, 6H), 1.20-1.67 (m, 49H), 2.03 (m, 8H), 2.38-2.75 (m, 7H), 2.77 (t, 4H), 5.35 (m, 8H).

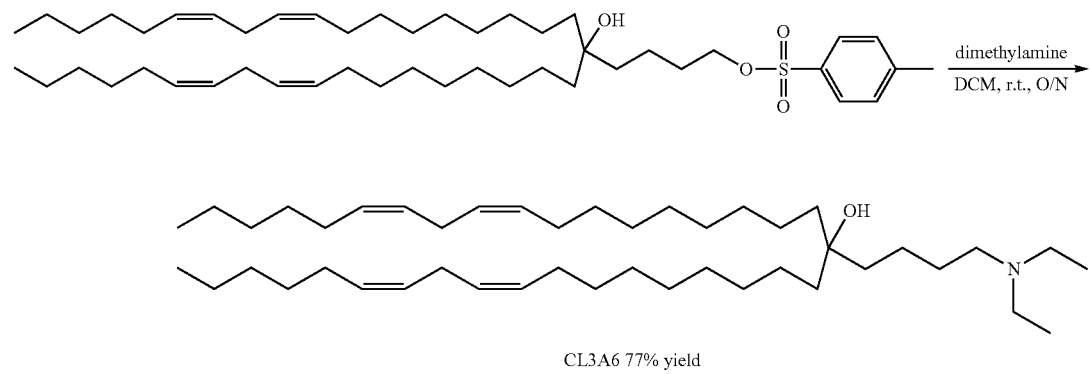

[Chem. 20]

CL3A6 77% yield

(23) (6Z,9Z,28Z,31Z)-19-(4-(Diethylamino)butyl) heptatriconta-6,9,28,31-tetraen-19-ol 603 mg (0.80 mmol) of 4-[(9z,12z)-octadienyl]-1-p-toluenesulfonyl-(13z,16z)-tricosadien-4-ol was dissolved in 4 mL of dichloromethane, 1.04 mL (10 mmol) of diethylamine was added thereto, and the mixture was reacted at 40° C. for 3 days. After the solvent was distilled off using a rotary evaporator, 5 mL of ethyl acetate was added, and the mixture was washed with 5 mL of a 0.1 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 401 mg (0.611 mmol) was obtained as a pale yellow oil. The yield was 77%.

$^1$H NMR; 400 MHz δ=0.87 (t, 6H), 1.20-1.67 (m, 52H), 2.03 (m, 8H), 2.38-2.75 (m, 6H), 2.77 (t, 4H), 5.35 (m, 8H).

[Chem. 21]

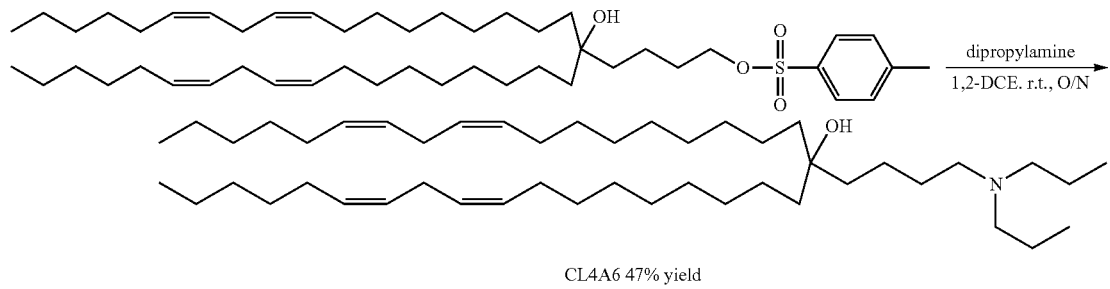

CL4A6 47% yield

(24) (6Z,9Z,28Z,31Z)-19-(4-(Dipropylamino)butyl) heptatriconta-6,9,28,31-tetraen-19-ol 189 mg (0.25 mmol) of 4-[(9z, 12z)-octadienyl]-1-p-toluenesulfonyl-(13z, 16z)-tricosadien-4-ol was dissolved in 1.5 mL of 1,2-dichloroethane, 41 µL (0.3 mmol) of dipropylamine was added thereto, and the mixture was reacted at room temperature for 8 days. After the solvent was distilled off using a rotary evaporator, 5 mL of ethyl acetate was added, and the mixture was washed with 5 mL of a 0.1 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 81 mg (0.118 mmol) was obtained as a pale yellow oil. The yield was 47%.

$^1$H NMR; 500 MHz δ=0.87 (t, 6H), 1.22-1.60 (m, 50H), 2.03 (m, 8H), 2.30-2.48 (m, 6H), 2.77 (t, 4H), 5.35 (m, 8H).

[Chem. 22]

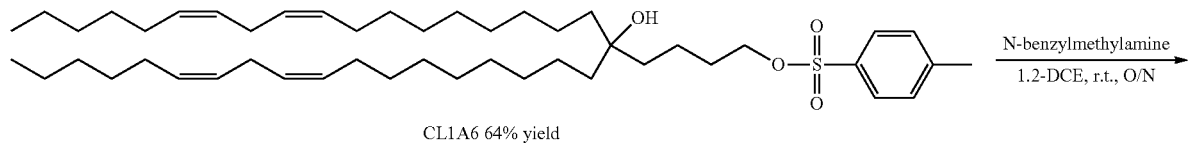

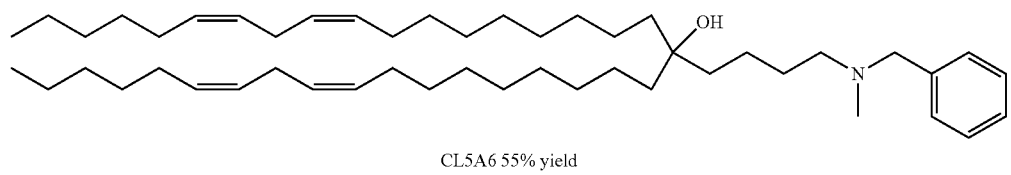

CL5A6 55% yield

(25) (6Z,9Z,28Z,31Z)-19-(4-(Benzyl(methyl)amino)butyl)heptatriconta-6,9,28,31-tetraen-19-ol 189 mg (0.25 mmol) of 4-[(9z, 12z)-octadienyl]-1-p-toluenesulfonyl-(13z,16z)-tricosadien-4-ol was dissolved in 1.5 mL of 1,2-dichloroethane, 39 µL (0.3 mmol) of N-benzylmethylamine was added thereto, and the mixture was reacted at room temperature for 8 days. After the solvent was distilled off using a rotary evaporator, 5 mL of ethyl acetate was added, and the mixture was washed with 5 mL of a 0.1 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 97.4 mg (0.138 mmol) was obtained as a pale yellow oil. The yield was 55%.

$^1$H NMR; 500 MHz δ=0.87 (t, 6H), 1.23-1.60 (m, 46H), 2.03 (m, 8H), 2.18 (s, 3H), 2.37 (t, 2H), 2.77 (t, 4H), 3.47 (s, 2H), 5.35 (m, 8H), 7.30 (m, 5H).

[Chem. 23]

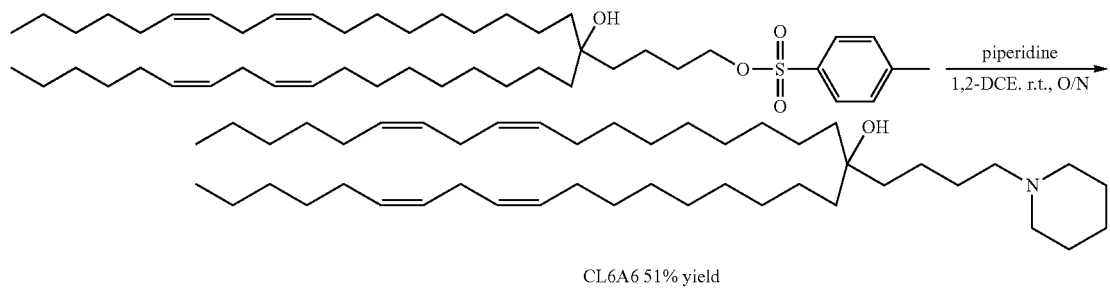

CL6A6 51% yield

(26) (6Z,9Z,28Z,31Z)-19-(4-(Piperidin-1-yl)butyl)heptatriconta-6,9,28,31-tetraen-19-ol 189 mg (0.25 mmol) of 4-[(9z, 12z)-octadienyl]-1-p-toluenesulfonyl-(13z,16z)-tricosadien-4-ol was dissolved in 1.5 mL of 1,2-dichloroethane, 30 µL (0.3 mmol) of piperidine was added thereto, and the mixture was reacted at room temperature for 8 days. After the solvent was distilled off using a rotary evaporator, 5 mL of ethyl acetate was added, and the mixture was washed with 5 mL of a 0.1 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 85.0 mg (0.127 mmol) was obtained as a pale yellow oil. The yield was 51%.

$^1$H NMR; 500 MHz δ=0.87 (t, 6H), 1.22-1.68 (m, 52H), 2.03 (m, 8H), 2.30-2.52 (m, 6H), 2.77 (t, 4H), 5.35 (m, 8H).

[Chem. 24]

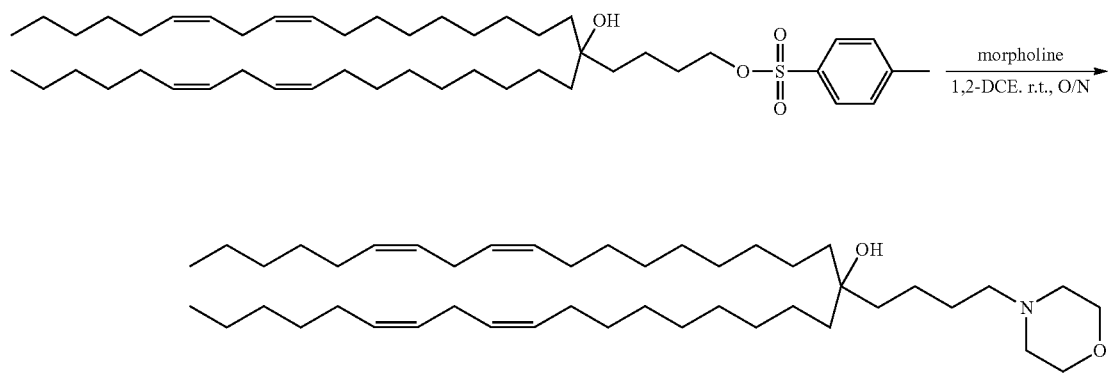

CL7A6 30% yield

(27) (6Z,9Z,28Z,31Z)-19-(4-Morpholinobutyl)heptatriconta-6,9,28,31-tetraen-19-ol 227 mg (0.30 mmol) of 4-[(9z, 12z)-octadienyl]-1-p-toluenesulfonyl-(13z,16z)-tricosadien-4-ol was dissolved in 2 mL of 1,2-dichloroethane, 87.1 mg (1.0 mmol) of morpholine was added thereto, and the mixture was reacted at room temperature for 7 days. After the solvent was distilled off using a rotary evaporator, 5 mL of dichloromethane was added, and the mixture was washed with 5 mL of a 0.1 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 60.0 mg (0.09 mmol) was obtained as a pale yellow oil. The yield was 30%.

$^1$H NMR; 500 MHz δ=0.87 (t, 6H), 1.22-1.65 (m, 46H), 2.03 (m, 8H), 2.34 (t, 2H), 2.42 (br, 4H), 2.77 (t, 4H), 3.71 (t, 4H), 5.35 (m, 8H).

[Chem. 25]

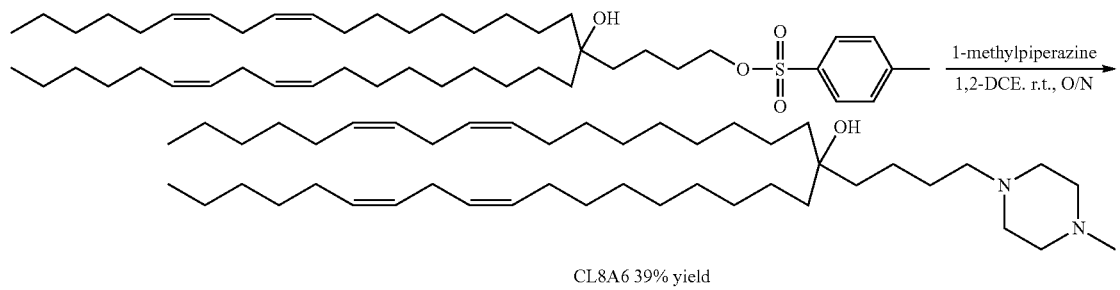

CL8A6 39% yield

(28) (6Z,9Z,28Z,31Z)-19-(4-(4-Methylpiperazin-1-yl)butyl)heptatriconta-6,9,28,31-tetraen-19-ol 227 mg (0.30 mmol) of 4-[(9z, 12z)-octadienyl]-1-p-toluenesulfonyl-(13z,16z)-tricosadien-4-ol was dissolved in 2 mL of 1,2-dichloroethane, 100.2 mg (1.0 mmol) of 1-methylpiperazine was added thereto, and the mixture was reacted at room temperature for 7 days. After the solvent was distilled off using a rotary evaporator, 5 mL of dichloromethane was added, and the mixture was washed with 5 mL of a 0.1 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 79.0 mg (0.116 mmol) was obtained as a pale yellow oil. The yield was 39%.

$^1$H NMR; 500 MHz δ=0.87 (t, 6H), 1.22-1.65 (m, 46H), 2.03 (m, 8H), 2.26-2.65 (m, 13H), 2.77 (t, 4H), 5.35 (m, 8H).

[Chem. 26]

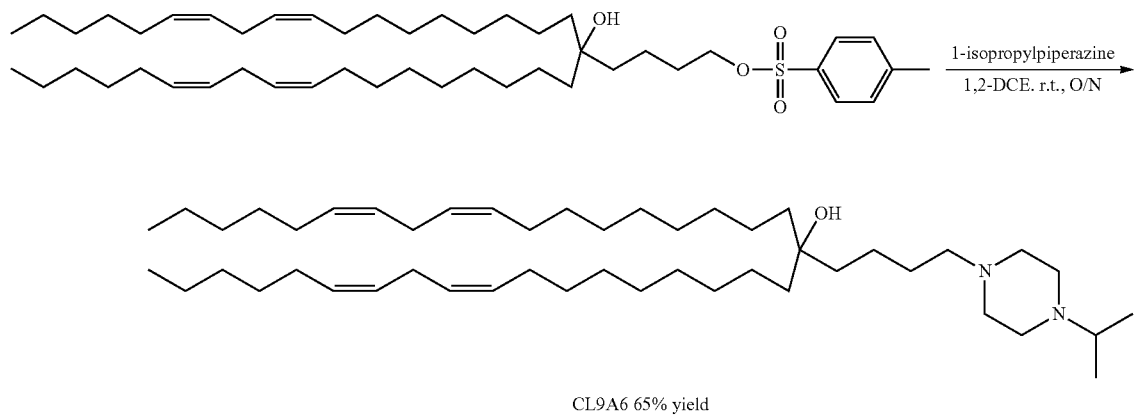

CL9A6 65% yield

(29) (6Z,9Z,28Z,31Z)-19-(4-(4-Isopropylpiperazin-1-yl)butyl)heptatriconta-6,9,28,31-tetraen-19-ol 189 mg (0.25 mmol) of 4-[(9z, 12z)-octadienyl]-1-p-toluenesulfonyl-(13z, 16z)-tricosadien-4-ol was dissolved in 2 mL of 1,2-dichloroethane, 42.7 µL (0.3 mmol) of 1-isopropylpiperazine was added thereto, and the mixture was reacted at room temperature for 8 days. After the solvent was distilled off using a rotary evaporator, 5 mL of ethyl acetate was added, and the mixture was washed with 5 mL of a 0.1 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 116 mg (0.163 mmol) was obtained as a pale yellow oil. The yield was 65%.

$^1$H NMR; 500 MHz δ=0.88 (t, 6H), 1.05 (d, 6H), 1.20-1.60 (m, 46H), 2.03 (m, 8H), 2.31-2.68 (m, 11H), 2.76 (t, 4H), 5.35 (m, 8H).

[Chem. 27]

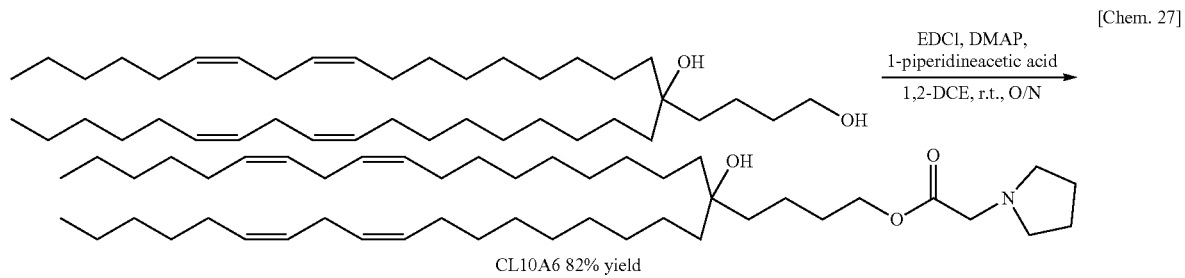

(30) (14Z,17Z)-5-Hydroxy-5-((9Z,12Z)-octadeca-9,12-dien-1-yl)tricosa-14,17-dien-1-yl 2-(pyrrolidine-1-yl)acetate 120.2 mg (0.20 mmol) of 4-[(9z, 12z)-octadecadienyl]-(13z, 16z)-tricosadiene-1,4-diol was dissolved in 1.0 mL of 1,2-dichloroethane, 38.7 mg (0.30 mmol) of 1-pyrrolidineacetic acid was added, thereafter, 6.1 mg (0.05 mmol) of DMAP and 57.5 mg (0.30 mmol) of 1-(3-dimethylaminopropyl)-3-ethylcarbodiimide hydrochloride (EDCI) were added thereto, and then the mixture was stirred overnight at room temperature. After the solvent was distilled off using a rotary evaporator, 5 mL of ethyl acetate was added, and the mixture was washed with 5 mL of a 0.1 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 117 mg (0.164 mmol) was obtained as a pale yellow oil. The yield was 82%.

$^1$H NMR; 500 MHz δ=0.88 (t, 6H), 1.22-1.69 (m, 46H), 1.82 (br, 4H), 2.03 (m, 8H), 2.65 (br, 4H), 2.77 (t, 4H), 3.33 (s, 2H), 4.13 (t, 2H), 5.35 (m, 8H).

[Chem. 28]

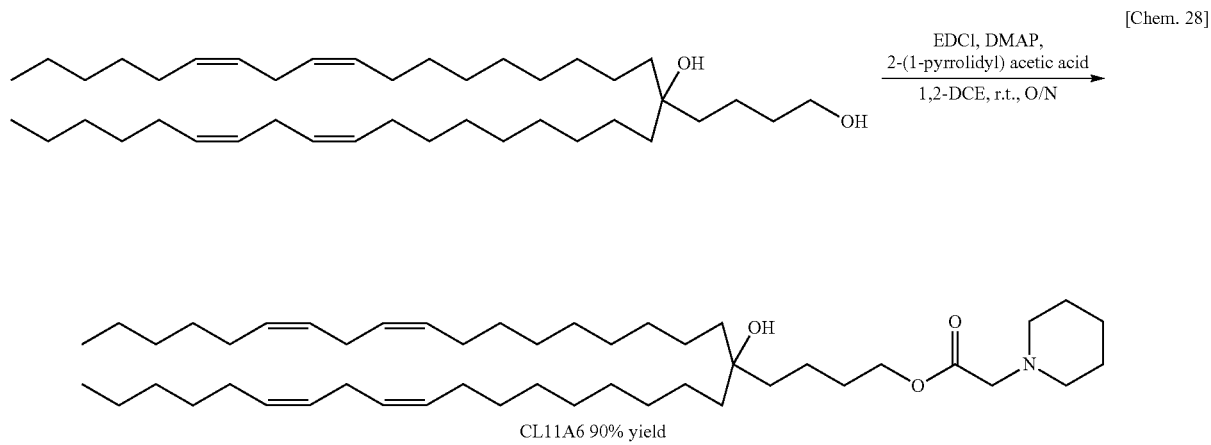

(31) (14Z,17Z)-5-Hydroxy-5-((9Z,12Z)-octadeca-9, 12-dien-1-yl)tricosa-14,17-dien-1-yl 2-(piperidine-1-yl)acetate 120.2 mg (0.20 mmol) of 4-[(9z, 12z)-octadecadienyl]-(13z, 16z)-tricosadiene-1,4-diol was dissolved in 1.0 mL of 1,2-dichloroethane, 43.0 mg (0.30 mmol) of 1-piperidineacetic acid was added, thereafter, 6.1 mg (0.05 mmol) of DMAP and 57.5 mg (0.30 mmol) of EDCI were added thereto, and then the mixture was stirred overnight at room temperature. After the solvent was distilled off using a rotary evaporator, 5 mL of ethyl acetate was added, and the mixture was washed with 5 mL of a 0.1 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 130 mg (0.179 mmol) was obtained as a pale yellow oil. The yield was 90%.

$^1$H NMR; 500 MHz δ=0.88 (t, 6H), 1.22-1.67 (m, 52H), 2.03 (m, 8H), 2.50 (br, 4H), 2.77 (t, 4H), 3.18 (s, 2H), 4.12 (t, 2H), 5.35 (m, 8H).

[Chem. 29]

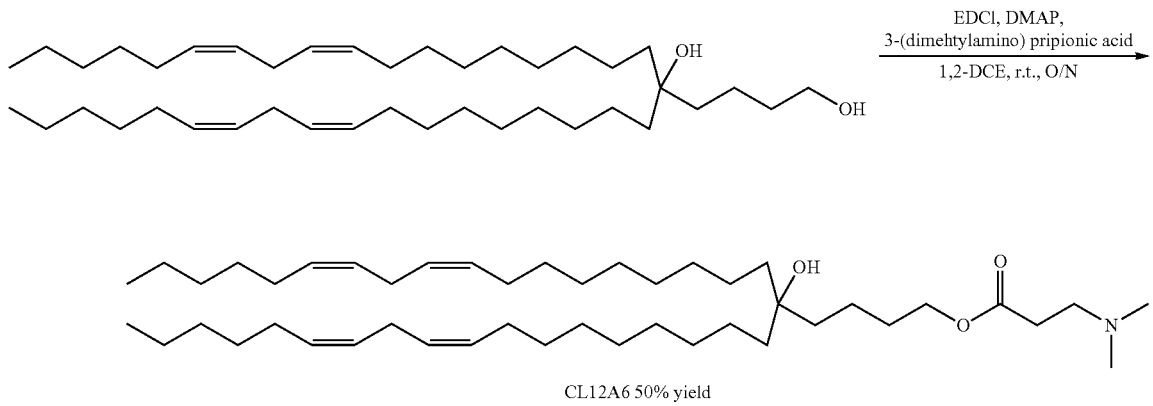

(32) (14Z,17Z)-5-Hydroxy-5-((9Z,12Z)-octadeca-9, 12-dien-1-yl)tricosa-14,17-dien-1-yl 3-(dimethylamino)propanoate 601 mg (1.0 mmol) of 4-[(9z, 12z)-octadecadienyl]-(13z, 16z)-tricosadiene-1,4-diol was dissolved in 5.0 mL of dichloromethane, 153.6 mg (1.0 mmol) of 3-(dimethylamino) propionate hydrochloride was added, thereafter, 12.2 mg (0.1 mmol) of DMAP and 230 mg (1.2 mmol) of EDCI were added thereto, and then the mixture was stirred overnight at room temperature. 50 mL of dichloromethane was added, and the mixture was washed with 50 mL of a 1 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 351 mg (0.501 mmol) was obtained as a pale yellow oil. The yield was 50%.

$^1$H NMR; 400 MHz δ=0.88 (t, 6H), 1.22-1.72 (m, 46H), 2.03 (m, 8H), 2.24 (s, 3H), 2.50 (t, 2H), 2.62 (t, 2H), 2.78 (t, 4H), 4.09 (t, 2H), 5.35 (m, 8H).

[Chem. 30]

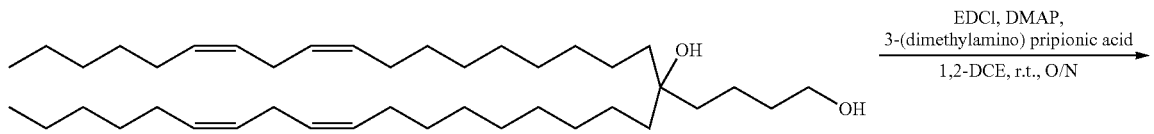

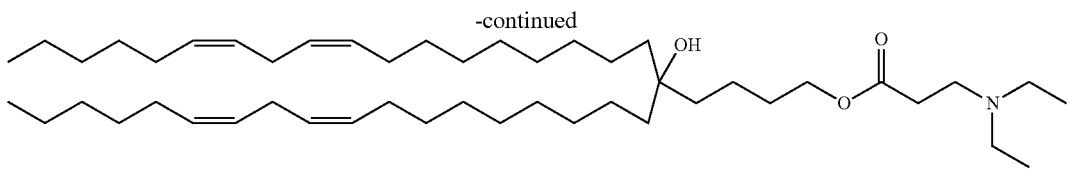

CLA13A6 59% yield

(33) (14Z,17Z)-5-Hydroxy-5-((9Z,12Z)-octadeca-9,12-dien-1-yl)tricosa-14,17-dien-1-yl 3-(diethylamino)propanoate 180 mg (0.30 mmol) of 4-[(9z, 12z)-octadecadienyl]-(13z, 16z)-tricosadiene-1,4-diol was dissolved in 2.0 mL of 1,2-dichloroethane, 72.7 mg (0.40 mmol) of 3-(diethylamino) propionate hydrochloride was added, thereafter, 6.0 mg (0.05 mmol) of DMAP and 96 mg (0.50 mmol) of EDCI were added thereto, and then the mixture was stirred overnight at room temperature. After the solvent was distilled off using a rotary evaporator, 5 mL of dichloromethane was added, and the mixture was washed with 5 mL of a 1 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 151 mg (0.207 mmol) was obtained as a pale yellow oil. The yield was 69%.

$^1$H NMR; 400 MHz δ=0.88 (t, 6H), 1.03 (t, 6H), 1.22-1.44 (m, 46H), 1.62 (m, 2H), 2.03 (m, 8H), 2.41-2.56 (m, 6H), 2.78 (m, 6H), 4.07 (t, 2H), 5.35 (m, 8H).

[Chem. 31]

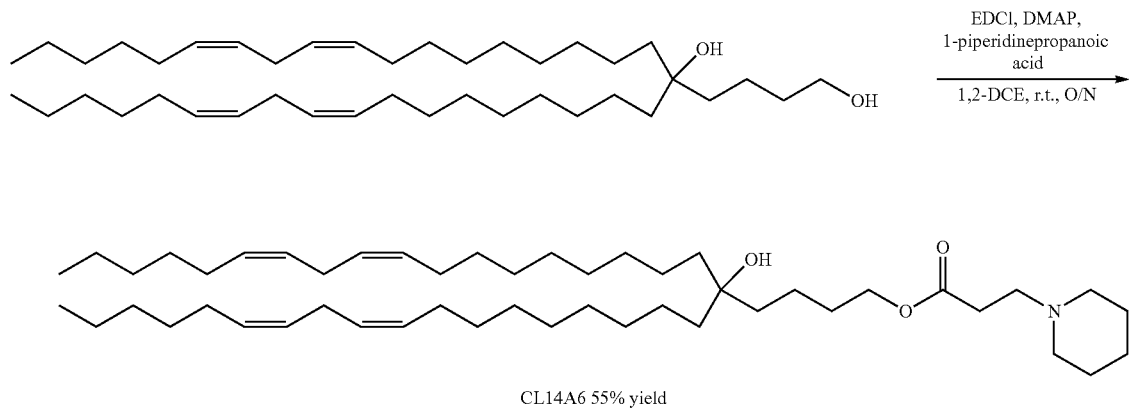

CL14A6 55% yield

(34) (14Z,17Z)-5-Hydroxy-5-((9Z,12Z)-octadeca-9,12-dien-1-yl)tricosa-14,17-dien-1-yl 3-(piperidine-1-yl)propanoate 120.2 mg (0.20 mmol) of 4-[(9z,12z)-octadecadienyl]-(13z,16z)-tricosadiene-1,4-diol was dissolved in 1.0 mL of 1,2-dichloroethane, 47.2 mg (0.30 mmol) of 1-piperidinepropionic acid was added, thereafter, 6.1 mg (0.05 mmol) of DMAP and 57.5 mg (0.30 mmol) of EDCI were added thereto, and then the mixture was stirred overnight at room temperature. After the solvent was distilled off using a rotary evaporator, 5 mL of ethyl acetate was added, and the mixture was washed with 5 mL of a 0.5 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 80.4 mg (0.109 mmol) was obtained as a pale yellow oil. The yield was 55%.

$^1$H NMR; 500 MHz δ=0.88 (t, 6H), 1.22-1.66 (m, 52H), 2.04 (m, 8H), 2.40 (br, 4H), 2.51 (br, 2H), 2.66 (br, 2H), 2.78 (t, 4H), 4.09 (t, 2H), 5.35 (m, 8H).

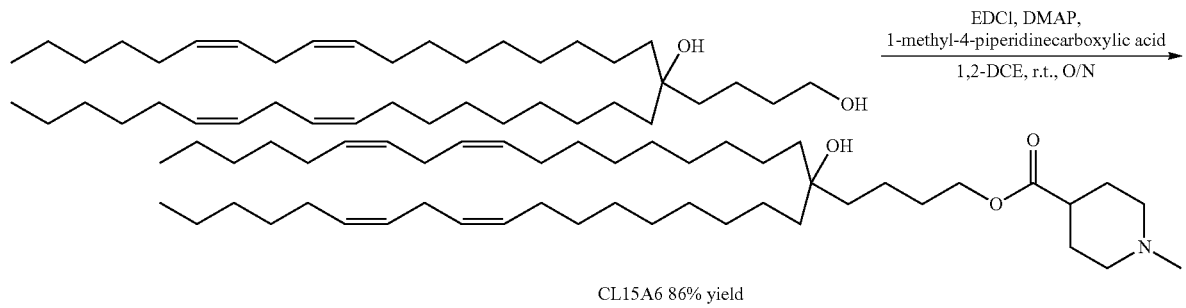

CL15A6 86% yield

(35) (14Z,17Z)-5-Hydroxy-5-((9Z,12Z)-octadeca-9,12-dien-1-yl)tricosa-14,17-dien-1-yl 1-methylpiperidine-4-carboxylate 842 mg (1.40 mmol) of 4-[(9z, 12z)-octadecadienyl]-(13z, 16z)-tricosadiene-1,4-diol was dissolved in 10 mL of 1,2-dichloroethane, 200 mg (1.40 mmol) of 1-methyl-4-piperidinecarboxylic acid was added, thereafter, 17.1 mg (0.14 mmol) of DMAP and 383 mg (2.0 mmol) of EDCI were added thereto, and then the mixture was stirred overnight at room temperature. After the solvent was distilled off using a rotary evaporator, 50 mL of ethyl acetate was added, and the mixture was washed with 50 mL of a 1 M aqueous sodium hydroxide solution. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 877 mg (1.21 mmol) was obtained as a colorless oil. The yield was 86%.

$^1$H NMR; 500 MHz δ=0.88 (t, 6H), 1.23-1.45 (m, 46H), 1.55-2.08 (m, 17H), 2.25 (s, 3H), 2.79 (t, 4H), 4.08 (t, 2H), 5.30-5.40 (m, 8H).

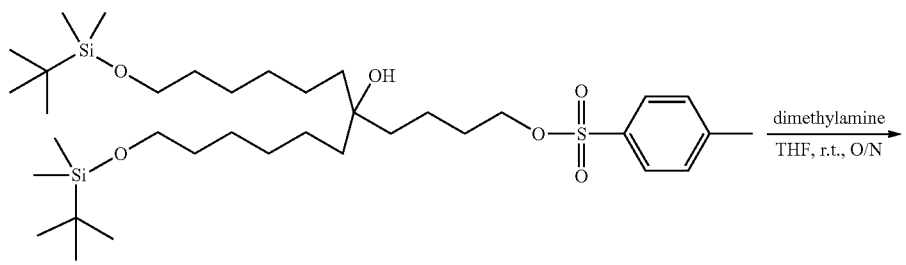

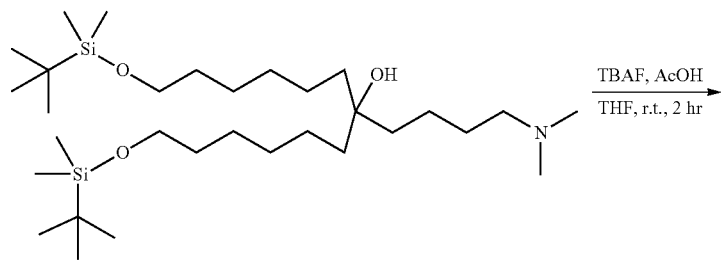

87% yield

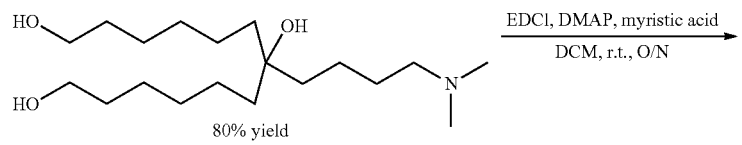

80% yield

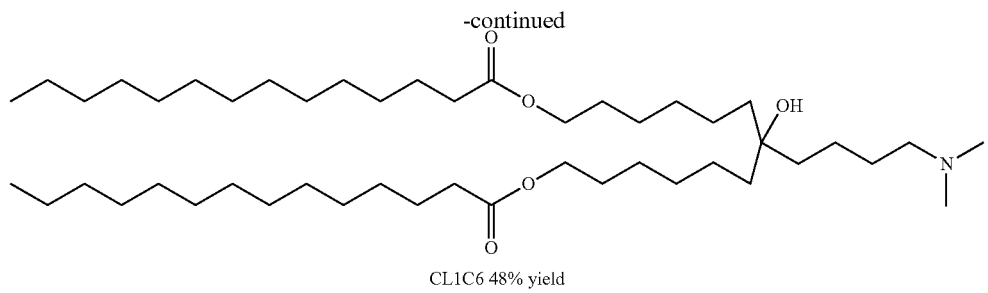

CL1C6 48% yield

(36) 11-(4-(Dimethylamino)butyl)-2,2,3,3,19,19,20,20-octamethyl-4,18-dioxa-3,19-disilahenicosan-11-ol 50 mL of a THF solution of 2.0 M dimethylamine was added to 8.78 g (12.78 mmol) of 11-((tert-butyldimethylsilyl)oxy)-5-(6-((tert-butyldimethylsilyl)oxy)hexyl)-5-hydroxyundecyl 4-methylbenzenesulfonate, and the mixture was allowed to react at room temperature for 6 days. The solvent was distilled off using a rotary evaporator, and then the residue was suspended in ethyl acetate, and separated and washed with a saturated aqueous sodium hydrogen carbonate solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 6.20 g (11.07 mmol) was obtained as a colorless oil. The yield was 87%.

(37) 7-(4-(Dimethylamino)butyl)tridecane-1,7,13-triol

A THF solution of 1.90 mL (33.21 mmol) of an acetic acid and 24.4 mL of 1.0 M tetrabutylammonium fluoride was added to 6.20 g (11.07 mmol) of 11-(4-(dimethylamino)butyl)-2,2,3,3,19,19,20,20-octamethyl-4,18-dioxa-3,19-disilahenicosan-11-ol, and the mixture was allowed to react at room temperature for 2 hours. The solvent was distilled off using a rotary evaporator, and then purified by subjecting it to reverse-phase silica gel chromatography {elution solvent; water (0.1% trifluoroacetic acid):acetonitrile (0.1% trifluoroacetic acid) (continuous gradient)}, and thereby 2.86 g (8.63 mmol) was obtained as a pale yellow oil. The yield was 80%.

$^1$H NMR; 400 MHz δ=1.20-1.60 (m, 26H), 2.80 (s, 6H), 3.02 (t, 2H), 3.62 (t, 4H).

(38) 7-(4-(Dimethylamino)butyl)-7-hydroxytridecane-1,13-diyl ditetradecanoate (CL1C6)

431 mg (1.30 mmol) of 7-(4-(dimethylamino)butyl)tridecane-1,7,13-triol was dissolved in 5 mL of dichloromethane, 713 mg (3.12 mmol) of myristic acid and 31.8 mg (0.26 mmol) of DMAP were added thereto, thereafter, 748 mg (3.90 mmol) of EDCI was added thereto, and the mixture was allowed to react overnight at room temperature. After the solvent was distilled off using a rotary evaporator, the residue was suspended in ethyl acetate, and insoluble matter was removed by filtration. The filtrate was separated and washed with a 0.5 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; dichloromethane:methanol (continuous gradient)}, and thereby 472 mg (0.627 mmol) of 7-(4-(dimethylamino)butyl)-7-hydroxytridecane-1,13-diyl ditetradecanoate (CL1C6) was obtained as a pale yellow oil. The yield was 48%.

$^1$H NMR; 400 MHz δ=0.88 (m, 6H), 1.16-1.70 (m, 70H), 2.22 (s, 6H), 2.28 (m, 6H), 4.04 (t, 4H).

[Chem. 34]

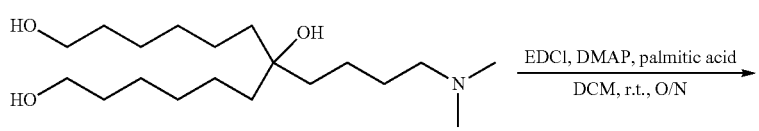

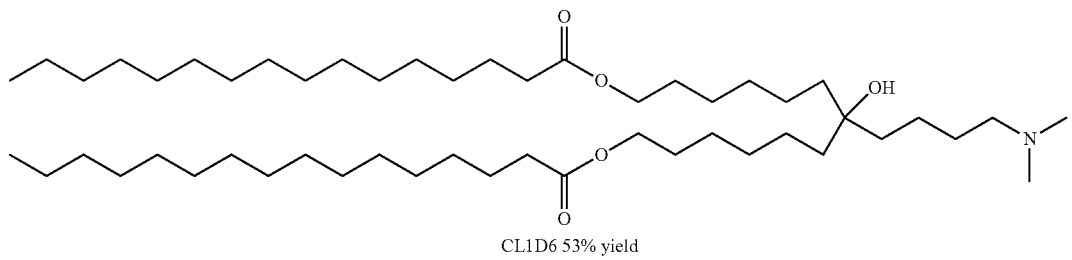

CL1D6 53% yield

(39) 7-(4-(Dimethylamino)butyl)-7-hydroxytridecane-1,13-diyl dipalmitate (CL1D6)

431 mg (1.30 mmol) of 7-(4-(dimethylamino)butyl)tridecane-1,7,13-triol was dissolved in 5 mL of dichloromethane, 800 mg (3.12 mmol) of palmitic acid and 31.8 mg (0.26 mmol) of DMAP were added thereto, thereafter, 748 mg (3.90 mmol) of EDCI was added thereto, and the mixture was allowed to react overnight at room temperature. After the solvent was distilled off using a rotary evaporator, the residue was suspended in ethyl acetate, and insoluble matter was removed by filtration. The filtrate was separated and washed with a 0.5 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; dichloromethane:methanol (continuous gradient)}, and thereby 557 mg (0.689 mmol) of 7-(4-(dimethylamino)butyl)-7-hydroxytridecane-1,13-diyl dipalmitate (CL1D6) was obtained as a pale yellow oil. The yield was 53%.

$^1$H NMR; 400 MHz δ=0.88 (m, 6H), 1.16-1.70 (m, 78H), 2.22 (s, 6H), 2.28 (m, 6H), 4.04 (t, 4H).

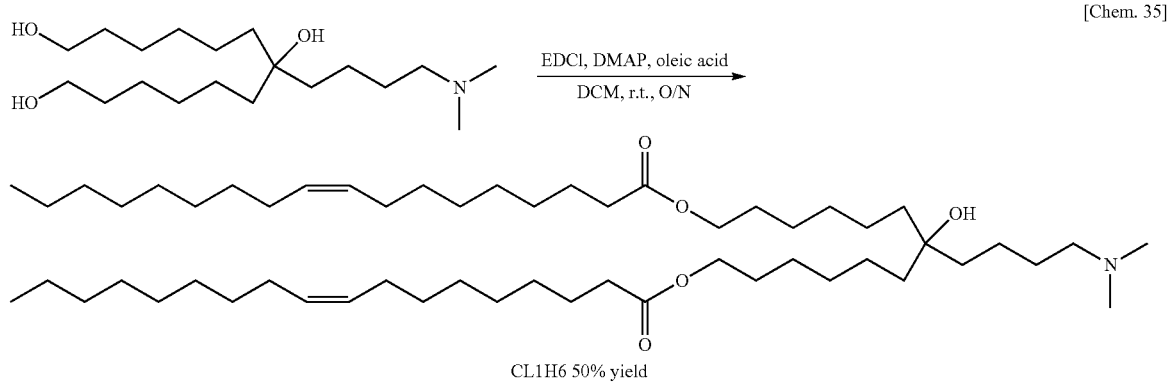

[Chem. 35]

(40) 7-(4-(Dimethylamino)butyl)-7-hydroxytridecane-1,13-diyl ditetradecanoate (CL1C6)

1.99 g (6.0 mmol) of 7-(4-(dimethylamino)butyl)tridecane-1,7,13-triol was dissolved in 20 mL of dichloromethane, 4.07 g (14.4 mmol) of oleic acid and 147 mg (1.20 mmol) of DMAP were added thereto, thereafter, 3.45 g (18.0 mmol) of EDCI was added thereto, and the mixture was allowed to react overnight at room temperature. After the solvent was distilled off using a rotary evaporator, the residue was suspended in ethyl acetate, and insoluble matter was removed by filtration. The filtrate was separated and washed with a 0.5 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; dichloromethane:methanol (continuous gradient)}, and thereby 2.56 g (2.98 mmol) of 7-(4-(dimethylamino)butyl)-7-hydroxytridecane-1,13-diyl dioleate (CL1H6) was obtained as a pale yellow oil. The yield was 50%.

$^1$H NMR; 400 MHz δ=0.88 (m, 6H), 1.16-1.75 (m, 66H), 2.01 (m, 8H), 2.21-2.35 (m, 12H), 4.04 (t, 4H), 5.32 (m, 4H).

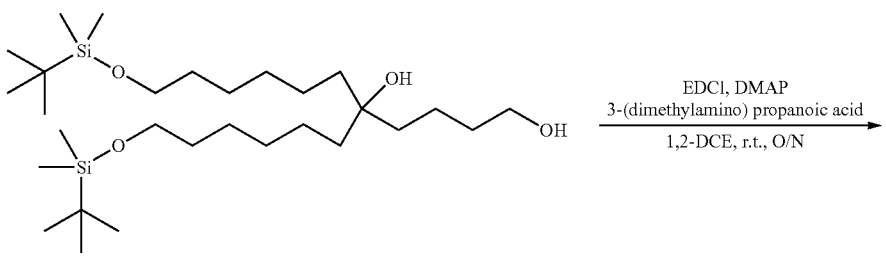

[Chem. 36]

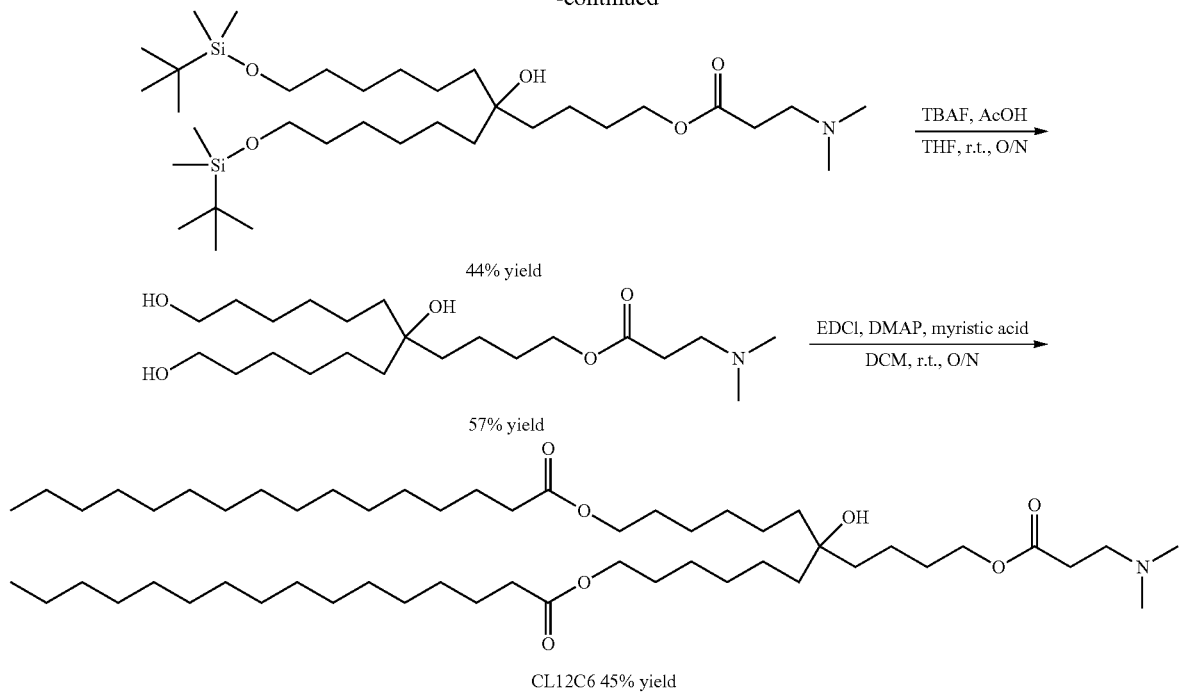

CL12C6 45% yield

(41) 11-((Tert-butyldimethylsilyl)oxy)-5-(6-((tert-butyldimethylsilyl)oxy)hexyl)-5-hydroxyundecyl 3-(dimethylamino)propanoate 12.73 g (23.9 mmol) of 11-((tert-butyldimethlsilyl)oxy)-5-(6-((tert-butyldimethylsilyl)oxy)hexyl)undecane-1,5-diol was dissolved in 50 mL of dichloromethane, 4.04 g (26.3 mmol) of 3-(dimethylamino)propanoic acid hydrochloride and 293 mg (2.4 mmol) of DMAP were added thereto, thereafter, 5.50 g (28.7 mmol) of EDCI was added thereto, and the mixture was allowed to react overnight at room temperature. The solvent was distilled off using a rotary evaporator, and then the residue was suspended in ethyl acetate, and separated and washed with a 0.5 M aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 6.66 g (10.54 mmol) was obtained as a pale yellow oil. The yield was 44%.

$^1$H NMR; 400 MHz δ=0.05 (s, 12H), 0.89 (s, 18H), 1.23-1.66 (m, 26H), 2.22 (s, 6H), 2.47 (t, 2H), 2.62 (t, 2H), 3.60 (t, 4H), 4.08 (t, 2H).

(42) 5,11-Dihydroxy-5-(6-hydroxyhexyl)undecyl 3-(dimethylamino)propanoate

A THF solution of 1.82 mL (31.6 mmol) of an acetic acid and 21.1 mL of 1.0 M tetrabutylammonium fluoride was added to 6.66 g (10.54 mmol) of 11-((tert-butyldimethylsilyl)oxy)-5-(6-((tert-butyldimethylsilyl)oxy)hexyl)-5-hydroxyundecyl 3-(dimethylamino)propanoate, and the mixture was allowed to react overnight at room temperature. The solvent was distilled off using a rotary evaporator, and then purified by subjecting it to reverse-phase silica gel chromatography {elution solvent; water (0.1% trifluoroacetic acid):acetonitrile (0.1% trifluoroacetic acid) (continuous gradient)}, and thereby 2.40 g (5.95 mmol) was obtained as a pale yellow oil. The yield was 57%.

$^1$H NMR; 400 MHz δ=1.22-1.50 (m, 20H), 1.52-1.70 (m, 6H), 2.81 (s, 6H), 2.87 (t, 2H), 3.33 (t, 2H), 3.63 (t, 4H), 4.12 (t, 2H).

(43) 7-(4-((3-(Dimethylamino)propanoyl)oxy)butyl)-7-hydroxytridecane-1,13-diyl ditetradecanoate (CL12C6)

800 mg (2.0 mmol) of 5,11-dihydroxy-5-(6-hydroxyhexyl)undecyl 3-(dimethylamino)propanoate was dissolved in 5 mL of dichloromethane, 1.005 g (4.4 mmol) of myristic acid and 48.9 mg (0.40 mmol) of DMAP were added thereto, thereafter, 959 mg (5.0 mmol) of EDCI was added thereto, and the mixture was allowed to react overnight at room temperature. After the solvent was distilled off using a rotary evaporator, the residue was suspended in ethyl acetate, and insoluble matter was removed by filtration. The filtrate was separated and washed with a 0.5 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 737 mg (0.894 mmol) was obtained as a white solid. The yield was 45%.

$^1$H NMR; 400 MHz δ=0.88 (t, 6H), 1.18-1.70 (m, 70H), 2.22-2.31 (m, 10H), 2.48 (t, 2H), 2.61 (t, 2H), 4.05 (m, 6H).

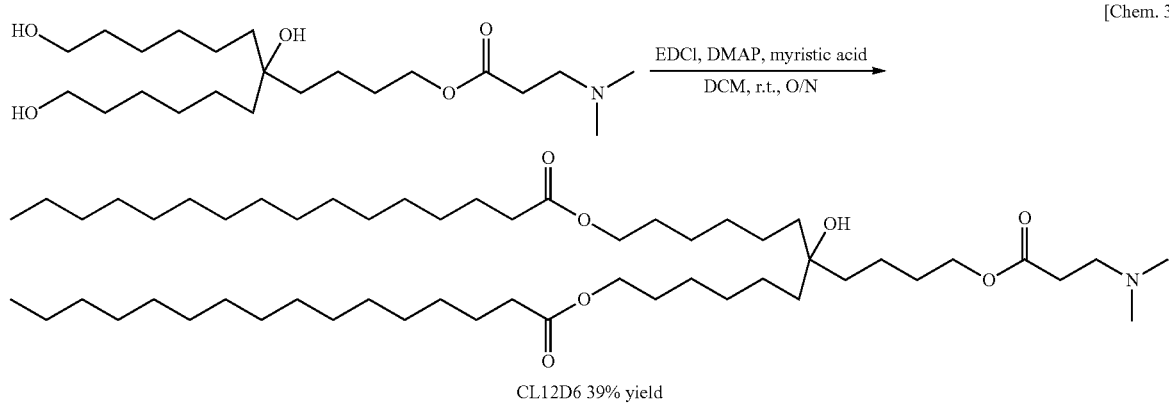

(44) 7-(4-((3-(Dimethylamino)propanoyl)oxy) butyl)-7-hydroxytridecane-1,13-diyl dipalmitate (CL12D6)

800 mg (2.0 mmol) of 5,11-dihydroxy-5-(6-hydroxyhexyl)undecyl 3-(dimethylamino)propanoate was dissolved in 5 mL of dichloromethane, 1.128 g (4.4 mmol) of palmitic acid and 48.9 mg (0.40 mmol) of DMAP were added thereto, thereafter, 959 mg (5.0 mmol) of EDCI was added thereto, and the mixture was allowed to react overnight at room temperature. After the solvent was distilled off using a rotary evaporator, the residue was suspended in ethyl acetate, and insoluble matter was removed by filtration. The filtrate was separated and washed with a 0.5 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 690 mg (0.784 mmol) was obtained as a white solid. The yield was 39%.

$^1$H NMR; 400 MHz δ=0.88 (t, 6H), 1.18-1.70 (m, 78H), 2.22-2.31 (m, 10H), 2.48 (t, 2H), 2.61 (t, 2H), 4.05 (m, 6H).

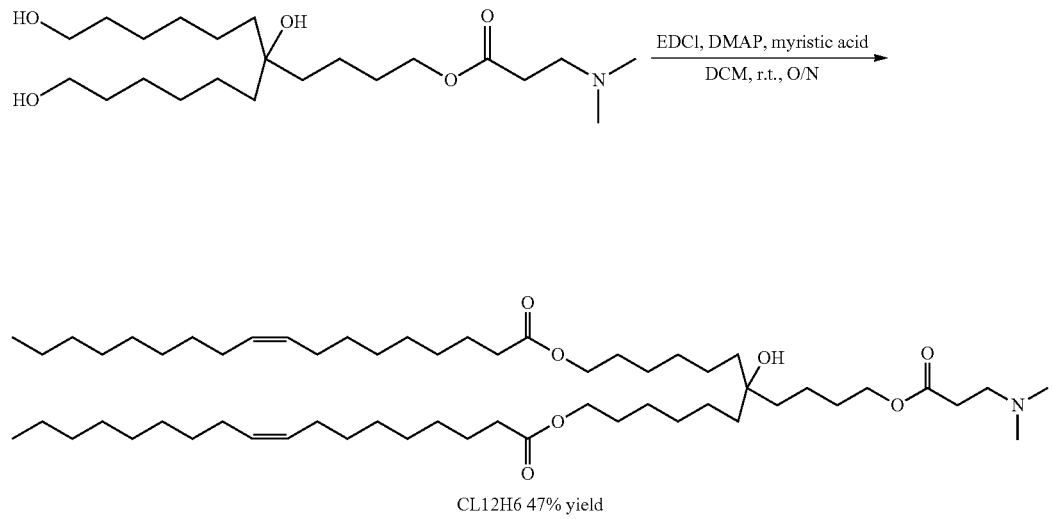

(45) 7-(4-((3-(Dimethylamino)propanoyl)oxy)butyl)-7-hydroxytridecane-1,13-diyl dioleate (CL12H6)

800 mg (2.0 mmol) of 5,11-dihydroxy-5-(6-hydroxyhexyl)undecyl 3-(dimethylamino)propanoate was dissolved in 5 mL of dichloromethane, 1.243 g (4.4 mmol) of oleic acid and 48.9 mg (0.40 mmol) of DMAP were added thereto, thereafter, 959 mg (5.0 mmol) of EDCI was added thereto, and the mixture was allowed to react overnight at room temperature. After the solvent was distilled off using a rotary evaporator, the residue was suspended in ethyl acetate, and insoluble matter was removed by filtration. The filtrate was separated and washed with a 0.5 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 874 mg (0.937 mmol) was obtained as a colorless oil. The yield was 47%.

$^1$H NMR; 400 MHz δ=0.88 (t, 6H), 1.11-1.68 (m, 66H), 2.01 (m, 8H), 2.22-2.31 (m, 10H), 2.48 (t, 2H), 2.62 (t, 2H), 4.04 (m, 6H), 5.32 (m, 4H).

[Chem. 39]

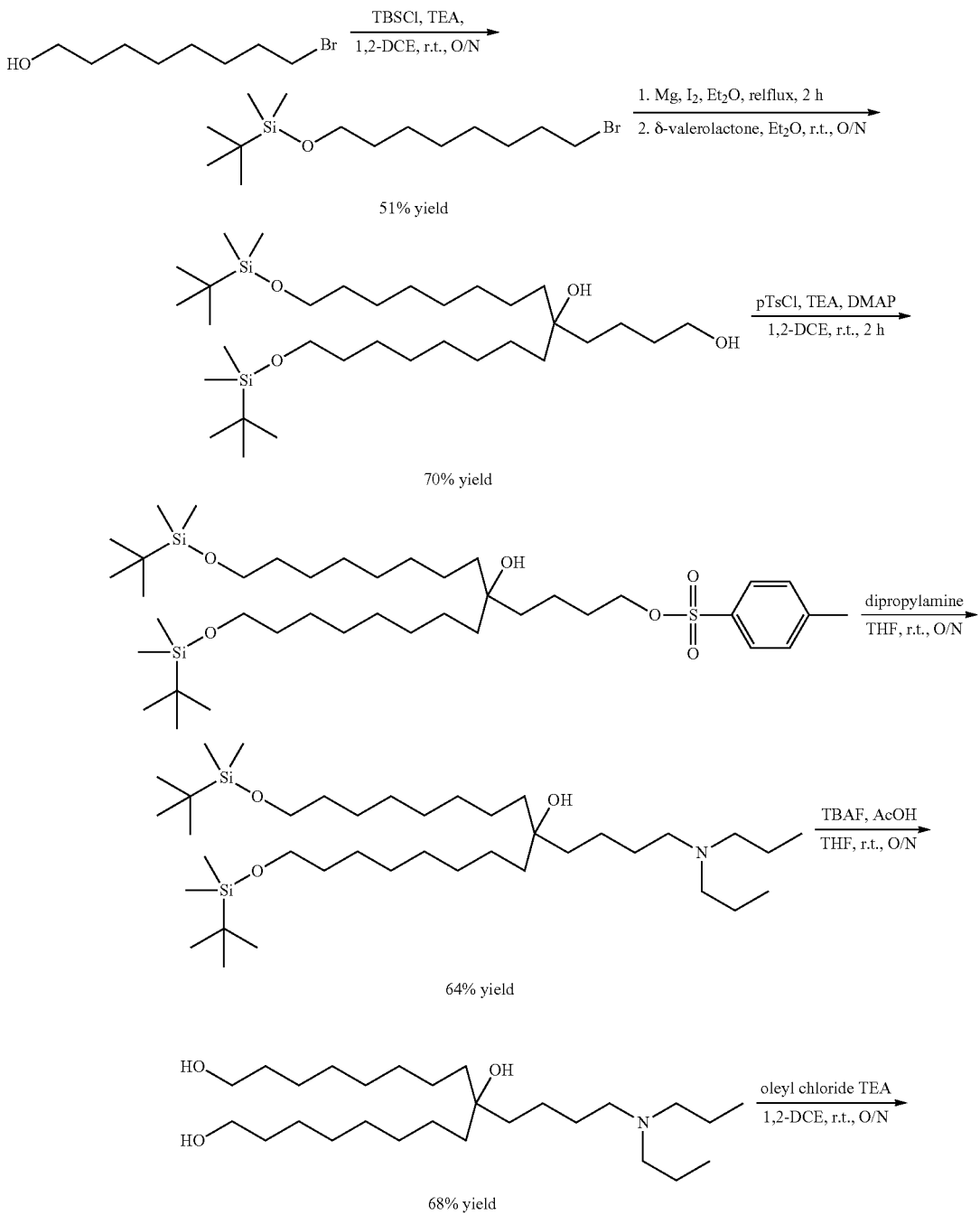

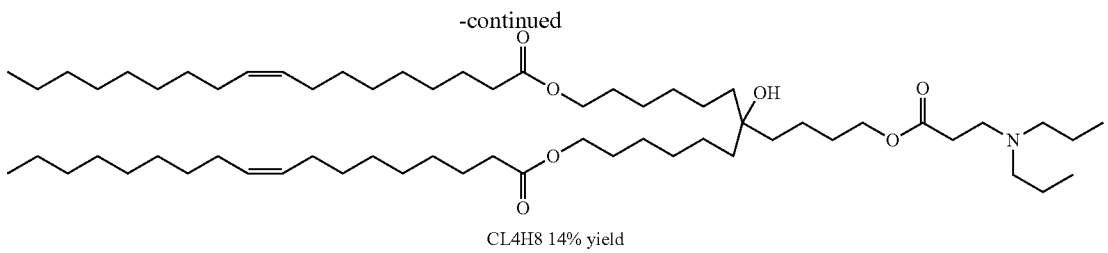

CL4H8 14% yield

(46) ((8-Bromooctyl)oxy)(tert-butyl)dimethylsilane 17.78 g (85.0 mmol) of 8-bromooctan-1-ol was dissolved in 100 mL of 1,2-dichloroethane and cooled to 4° C. After adding 13.86 g (92.0 mmol) of TBSCl, 15.33 mL (110 mmol) of TEA was added dropwise, and the mixture was stirred overnight at room temperature. The solvent was distilled off using a rotary evaporator, 300 mL of hexane was added and suspended, the insoluble matter was removed by Celite filtration, and thereby a crude product was obtained. The crude product was purified by subjecting it to silica gel chromatography {elution solvent; hexane:ethyl acetate (continuous gradient)}, and thereby 14.0 g (44.3 mmol) was obtained as a colorless oil. The yield was 51%.

$^1$H NMR; 400 MHz δ=0.04 (s, 6H), 0.89 (s, 9H), 1.31 (m, 6H), 1.42 (m, 2H), 1.50 (m, 2H), 1.85 (tt, 2H), 3.40 (t, 2H) 3.59 (t, 2H).

(47) 13-((Tert-butyldimethylsilyl)oxy)-5-(8-((tert-butyldimethylsilyl)oxy)octyl) tridecane-1,5-diol 0.70 g (2.17 mmol) of ((8-bromooctyl)oxy)(tert-butyl)dimethylsilane was dissolved in 4 mL of diethyl ether, 1.26 g (52 mmol) of shaved magnesium was added thereto, and then an iodine primary fragment was added. The mixture was allowed to stand at room temperature for 10 minutes, stirred while heating to 40° C. in an oil bath, and 13.3 g (41.13 mmol) of ((8-bromooctyl)oxy)(tert-butyl)dimethylsilane dissolved in 11 mL of diethyl ether was added dropwise. The mixture was reacted at 40° C. for 2 hours and then cooled to 4° C. Subsequently, 1.81 mL (19.5 mmol) of δ-valerolactone was added and allowed to react overnight at room temperature. Next, the resultant was cooled to 4° C., and 5% sulfuric acid was added dropwise to dissolve the residual magnesium. The mixture was diluted with diethyl ether, and the organic layer was separated and washed with water and saturated saline. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; hexane:ethyl acetate (continuous gradient)}, and thereby 8.00 g (13.58 mmol) was obtained as a colorless oil. The yield based on δ-valerolactone was 70%.

$^1$H NMR; 400 MHz δ=0.05 (s, 12H), 0.89 (s, 18H), 1.25-1.60 (m, 34H), 3.59 (t, 4H), 3.65 (t, 2H).

(48) 13-((Tert-butyldimethylsilyl)oxy)-5-(8-((tert-butyldimethylsilyl)oxy)octyl)-5-hydroxytridecyl 4-methylbenzenesulfonate 8.00 g (13.58 mmol) of 13-((tert-butyldimethylsilyl)oxy)-5-(8-((tert-butyldimethylsilyl)oxy)octyl)tridecane-1,5-diol was dissolved in 30 mL of 1,2-dichloroethane, and 183 mg (1.50 mmol) of DMAP and 2.79 mL (20.0 mmol) of TEA were added thereto and cooled to 4° C. Subsequently, 2.86 g (15.0 mmol) of pTsCl was gradually added, followed by reaction at room temperature for 2 hours. The solvent was distilled off using a rotary evaporator, the residue was suspended in ethyl acetate, and separated and washed with water and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; hexane:ethyl acetate (continuous gradient)}, and thereby a colorless oil was obtained.

(49) 13-(4-(Diisopropylamino)butyl)-2,2,3,3,23,23,24,24-octamethyl-4,22-dioxa-3,23-disilapentacosan-13-ol 10.09 g (13.58 mmol) of 13-((tert-butyldimethylsilyl)oxy)-5-(8-((tert-butyldimethylsilyl)oxy)octyl)-5-hydroxytridecyl 4-methylbenzenesulfonate was added to 30 mL of 1,2-dichloroethane and cooled to 4° C. Subsequently, 3.71 mL (27.2 mmol) of dipropylamine was added, followed by reaction at room temperature for 10 days. The solvent was distilled off using a rotary evaporator, and then the residue was suspended in ethyl acetate, and separated and washed with a 0.2 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 5.86 g (8.72 mmol) was obtained as a pale yellow oil. The yield was 64%.

$^1$H NMR; 400 MHz δ=0.05 (s, 12H), 0.89 (s, 18H), 0.98 (t, 6H), 1.22-1.80 (m, 38H), 2.98 (m, 6H), 3.58 (t, 4H).

(50) 9-(4-(Diisopropylamino)butyl)heptadecane-1,9,17-triol

A THF solution of 1.72 mL (30 mmol) of an acetic acid and 20 mL of a 1.0 M tetrabutylammonium fluoride was added to 4.50 g (6.70 mmol) of 13-(4-(diisopropylamino)butyl)-2,2,3,3,23,23,24,24-octamethyl-4,22-dioxa-3,23-disilapentacosan-13-ol, and the mixture was allowed to react overnight at room temperature. The solvent was distilled off using a rotary evaporator, and then purified by subjecting it to reverse-phase silica gel chromatography {elution solvent; water (0.1% trifluoroacetic acid):acetonitrile (0.1% trifluoroacetic acid) (continuous gradient)}, and thereby 2.03 g (4.57 mmol) was obtained as a pale yellow oil. The yield was 68%.

(51) 9-(4-(Diisopropylamino)butyl)-7-hydroxyheptadecane-1,17-diyl dioleate (CL4H8)

222 mg (0.50 mmol) of 9-(4-(diisopropylamino)butyl)heptadecane-1,9,17-triol was dissolved in 2.5 mL of 1,2- dichloroethane and cooled to 4° C. Subsequently, after adding 451 mg (1.50 mmol) of oleyl chloride, 836 μL (6.0 mmol) of TEA was added dropwise, and the mixture was allowed to react at room temperature for 3 hours. After the solvent was distilled off using a rotary evaporator, the residue was suspended in ethyl acetate, and insoluble matter was removed by filtration. The filtrate was separated and washed with a 0.2 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 68.4 mg (0.070 mmol) was obtained as a pale yellow oil. The yield was 14%.

$^1$H NMR; 400 MHz δ=0.88 (m, 12H), 1.20-1.68 (m, 82H), 2.01 (m, 8H), 2.27 (t, 4H), 2.32-2.45 (m, 6H), 4.04 (t, 4H), 5.32 (m, 4H).

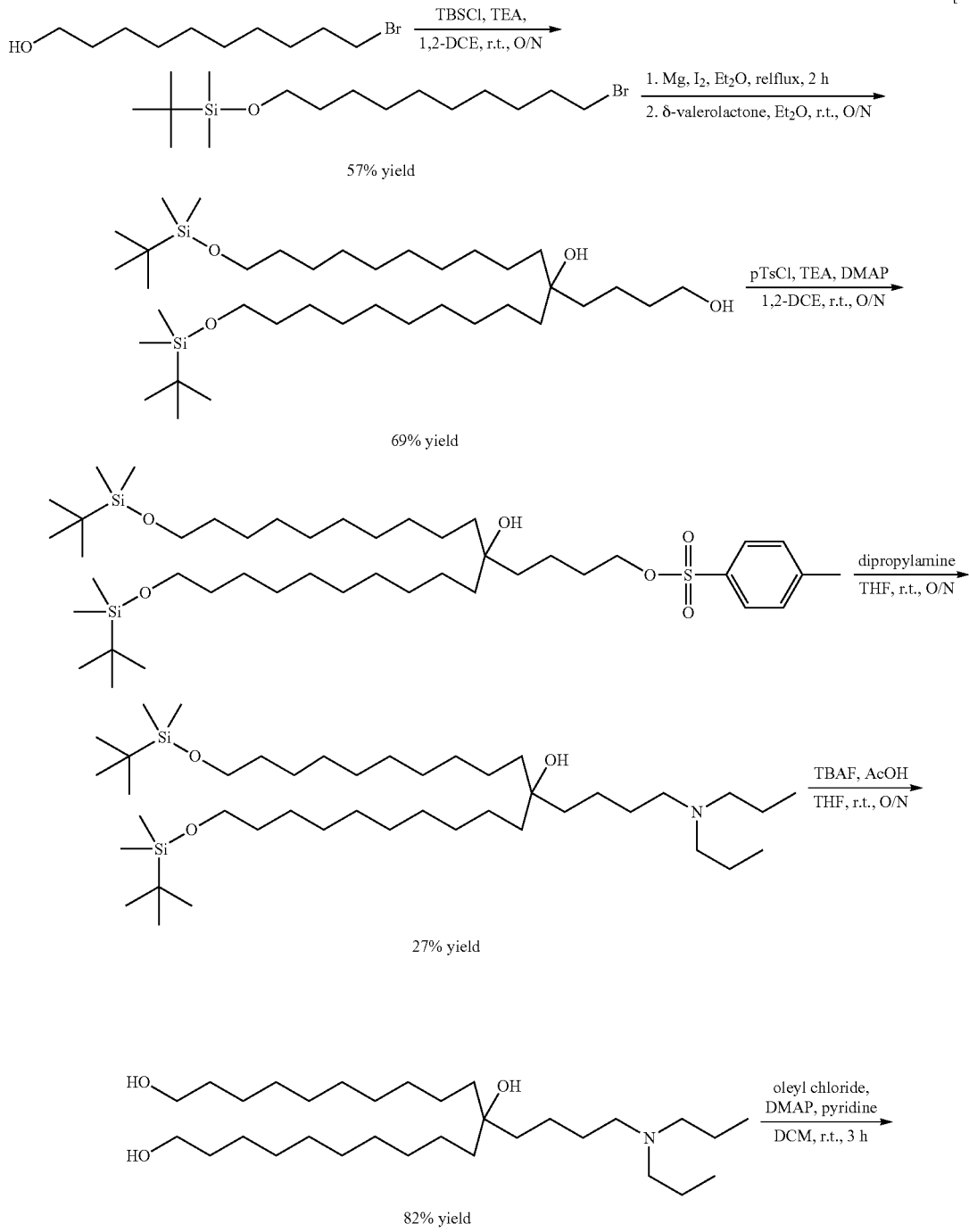

[Chem. 40]

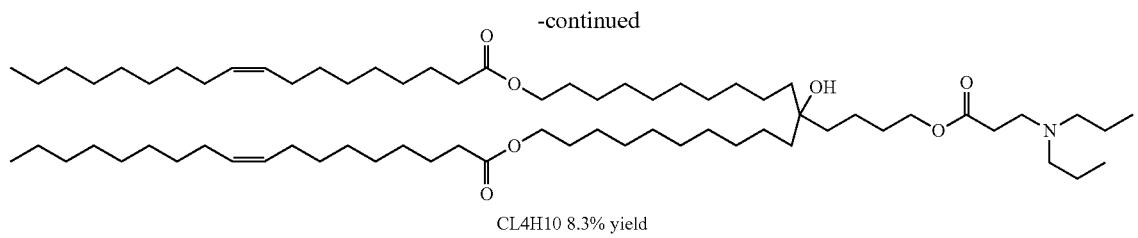

CL4H10 8.3% yield

(52) ((10-Bromodecyl)oxy)(tert-butyl)dimethylsilane 25.0 g (105.4 mmol) of 10-bromodecan-1-ol was dissolved in 100 mL of 1,2-dichloroethane and cooled to 4° C. After adding 17.3 g (115 mmol) of TBSCl, 19.5 mL (140 mmol) of TEA was added dropwise, and the mixture was stirred overnight at room temperature. The solvent was distilled off using a rotary evaporator, 300 mL of hexane was added and suspended, the insoluble insoluble matter was removed by Celite filtration, and thereby a crude product was obtained. The crude product was purified by subjecting it to silica gel chromatography {elution solvent; hexane:ethyl acetate (continuous gradient)}, and thereby 21.0 g (59.8 mmol) was obtained as a colorless oil. The yield was 57%.

$^1$H NMR; 400 MHz δ=0.05 (s, 6H), 0.89 (s, 9H), 1.24-1.34 (m, 10H), 1.42 (tt, 2H), 1.51 (tt, 2H), 1.72-1.88 (m, 2H), 3.40 (t, 2H), 3.59 (t, 2H).

(53) 15-((Tert-butyldimethylsilyl)oxy)-5-(10-((tert-butyldimethylsilyl)oxy)decyl)pentadecane-1,5-diol 1.05 g (2.99 mmol) of ((10-bromodecyl)oxy)(tert-butyl) dimethylsilane was dissolved in 4 mL of diethyl ether, 1.75 g (72.0 mmol) of shaved magnesium was added thereto, and then an iodine primary fragment was added. The mixture was allowed to stand at room temperature for 10 minutes, stirred while heating to 40° C. in an oil bath, and 19.95 g (56.81 mmol) of ((10-bromodecyl)oxy)(tert-butyl)dimethylsilane dissolved in 11 mL of diethyl ether was added dropwise. The mixture was reacted at 40° C. for 2 hours and then cooled to 4° C. Subsequently, 3.67 mL (39.6 mmol) of δ-valerolactone was added and allowed to react overnight at room temperature. Next, the resultant was cooled to 4° C., and 5% sulfuric acid was added dropwise to dissolve the residual magnesium. The mixture was diluted with diethyl ether, and the organic layer was separated and washed with water and saturated saline. Subsequently, the organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; hexane:ethyl acetate (continuous gradient)}, and thereby 11.95 g (18.52 mmol) was obtained as a colorless oil. The yield based on δ-valerolactone was 69%.

$^1$H NMR; 400 MHz δ=0.05 (s, 12H), 0.89 (s, 18H), 1.22-1.60 (m, 42H), 3.59 (t, 4H), 3.66 (t, 2H).

(54) 15-((Tert-butyldimethylsilyl)oxy)-5-(10-((tert-butyldimethylsilyl)oxy)decyl)-5-hydroxypentadecyl 4-methylbenzenesulfonate 6.00 g (9.30 mmol) of 15-((tert-butyldimethylsilyl)oxy)-5-(10-((tert-butyldimethylsilyl)oxy)decyl)pentadecane-1,5-diol was dissolved in 30 mL of 1,2-dichloroethane, and 114 mg (0.93 mmol) of DMAP and 3.24 mL (23.25 mmol) of TEA were added thereto and cooled to 4° C. Subsequently, 2.13 g (11.16 mmol) of pTsCl was gradually added, followed by reaction at room temperature overnight. The solvent was distilled off using a rotary evaporator, the residue was suspended in ethyl acetate, and separated and washed with water and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {elution solvent; hexane:ethyl acetate (continuous gradient)}, and thereby a colorless oil was obtained.

(55) 15-(4-(Diisopropylamino)butyl)-2,2,3,3,27,27,28,28-octamethyl-4,26-dioxa-3,27-disilanonacosan-15-ol 5 mL of THF was added to 1.66 g (2.08 mmol) of 15-((tert-butyldimethylsilyl)oxy)-5-(10-((tert-butyldimethylsilyl)oxy)decyl)-5-hydroxypentadecyl 4-methylbenzenesulfonate and cooled to 4° C. Subsequently, 569 μL (4.16 mmol) of dipropylamine was added, followed by reaction at room temperature for 21 days. The solvent was distilled off using a rotary evaporator, and then the residue was suspended in ethyl acetate, and separated and washed with a 1 M aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 1.80 g (2.47 mmol) was obtained as a pale yellow oil. The yield was 27%.

$^1$H NMR; 400 MHz δ=0.05 (s, 12H), 0.89 (m, 24H), 1.23-1.62 (m, 46H), 2.30-2.44 (m, 6H), 3.58 (t, 4H).

(56) 11-(4-(Diisopropylamino)butyl)henicosan-1,11,21-triol

A THF solution of 515 μL (9.0 mmol) of an acetic acid and 6 mL of 1.0 M tetrabutylammonium fluoride was added to 1.80 g (2.47 mmol) of 15-(4-(diisopropylamino)butyl)-2,2,3,3,27,27,28,28-octamethyl-4,26-dioxa-3,27-disilanonacosan-15-ol, and the mixture was allowed to react overnight at room temperature. The solvent was distilled off using a rotary evaporator, and then purified by subjecting it to reverse-phase silica gel chromatography {elution solvent; water (0.1% trifluoroacetic acid):acetonitrile (0.1% trifluoroacetic acid) (continuous gradient)}, and thereby 1.01 g (2.02 mmol) was obtained as a pale yellow oil. The yield was 82%.

$^1$H NMR; 400 MHz δ=0.99 (t, 6H), 1.20-1.79 (m, 46H), 3.00 (m, 6H), 3.63 (t, 4H).

(57) 11-(4-(Diisopropylamino)butyl)-11-hydroxy-henicosane-1,21-diyl dioleate (CL4H10)

250 mg (0.50 mmol) of 11-(4-(diisopropylamino)butyl) henicosane-1,11,21-triol was dissolved in 4 mL of dichloromethane and cooled to 4° C. Subsequently, 602 mg (2.0 mmol) of oleyl chloride was added, and then 12.2 mg (0.10 mmol) of DMAP and 322 μL (4.0 mmol) of pyridine were added dropwise, and the mixture was allowed to react at room temperature for 3 hours. After the solvent was distilled off using a rotary evaporator, the residue was suspended in ethyl acetate, and insoluble matter was removed by filtration. The filtrate was separated and washed with a 0.5 N aqueous sodium hydroxide solution and saturated saline. The organic layer was dehydrated by adding anhydrous sodium sulfate. After filtering the resultant, the solvent was distilled off using a rotary evaporator to obtain a crude product. The crude product was purified by subjecting it to silica gel chromatography {eluent; dichloromethane:methanol (continuous gradient)}, and thereby 42.5 mg (0.041 mmol) was obtained as a pale yellow oil. The yield was 8.3%.

$^1$H NMR; 400 MHz δ=0.88 (m, 12H), 1.17-1.65 (m, 90H), 2.01 (m, 8H), 2.28 (t, 4H), 2.30-2.45 (m, 6H), 4.05 (t, 4H), 5.32 (m, 4H).

Example 2

A pH-sensitive cationic lipid which has various hydrophilic sites and in which a hydrophobic scaffold was derived from a linoleic acid was evaluated. In accordance with the method of the examples (Example 2) of Patent Literature 6, LNPs were prepared by mixing respective pH-sensitive cationic lipid, cholesterol, and methoxy polyethyleneglycol 2000 dimirystoylglycerol (PEG-DMG 2000) at a molar ratio of 50:50:0.75 to 1.5 by an alcohol dilution method (FIG. 1). An average particle diameter calculated by a phase light scattering method was 80 to 120 nm, and an siRNA loading rate was 90% or more.

Figure 2:
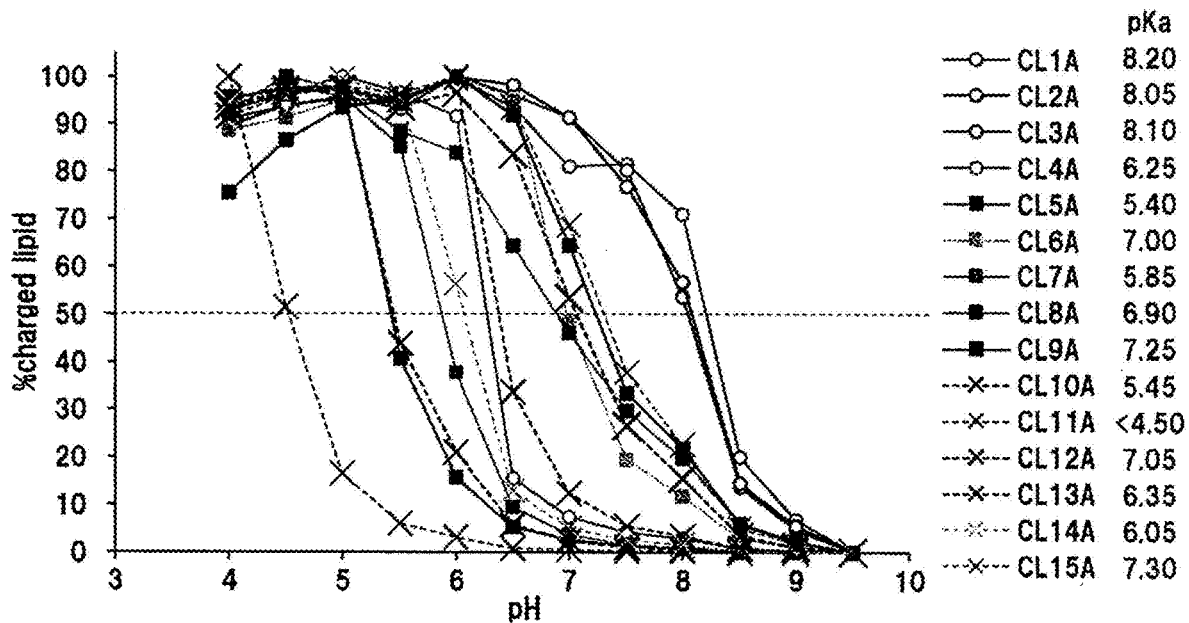
FIG. 2 is a graph showing pKa's of respective LNPs containing lipid compounds each having different chemical structures at hydrophilic sites in Example 2.

A pKa of each LNP was obtained using p-Toluenesulfonic acid (TNS). TNS's (final concentration: 0.75 μM) and LNPs (final concentration: 30 μM) were mixed in a buffer solution adjusted to each pH, and a fluorescence intensity was measured with a microplate reader. The highest value and the lowest value were respectively calculated as 100% and 0% charge, and a pH showing 50% of a charge rate was calculated as a pKa. As a result, various pKa's were shown in a wide range from 4.5 or less to 8.2 depending on chemical structures around a tertiary amino group (FIG. 2).

Figure 3A:
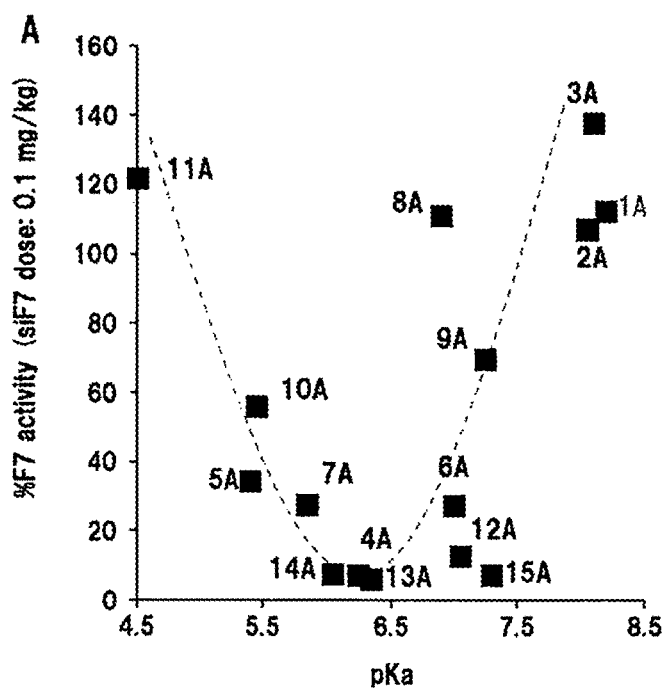
FIG. 3A is a graph showing in vivo F7 knockdown activity of respective LNPs containing lipid compounds each having different chemical structures at hydrophilic sites in Example 2.

Hemolysis activity, in vitro knockdown activity, and in vivo F7 knockdown activity, which are indicators of endosome escape activity, were measured. Regarding the hemolysis activity, mouse erythrocytes and LNPs were mixed in a buffer solution adjusted to pH 6.5, the mixture was incubated at 37° C. for 30 minutes and then centrifuged, and an absorbance of the supernatant at 545 nm was measured. Hemolysis efficiency of each sample was calculated by respectively using a sample to which LNPs were not added and a sample to which Triton X-100 having a final concentration of 0.5% was added, as a negative control and a positive control. Regarding the in vitro knockdown activity, LNPs loaded with siRNA against luciferase were added to HeLa cells stably expressing dual-luciferase (HeLa-dluc) at various concentrations, and knockdown efficiency was calculated 24 hours after the addition by dual-luciferase assay. An expression level of a target luciferase against the added concentration was plotted, and an siRNA concentration that inhibited 50% thereof was calculated as $IC_{50}$. Regarding the in vivo F7 knockdown activity, 0.1 mg siRNA/kg of LNPs loaded with siRNA against F7 were intravenously administered to an ICR mouse (4 weeks old, female), and F7 enzyme activity in plasma was measured 24 hours after the administration. Each activity against pKa was plotted (FIG. 3).

Figure 3B:
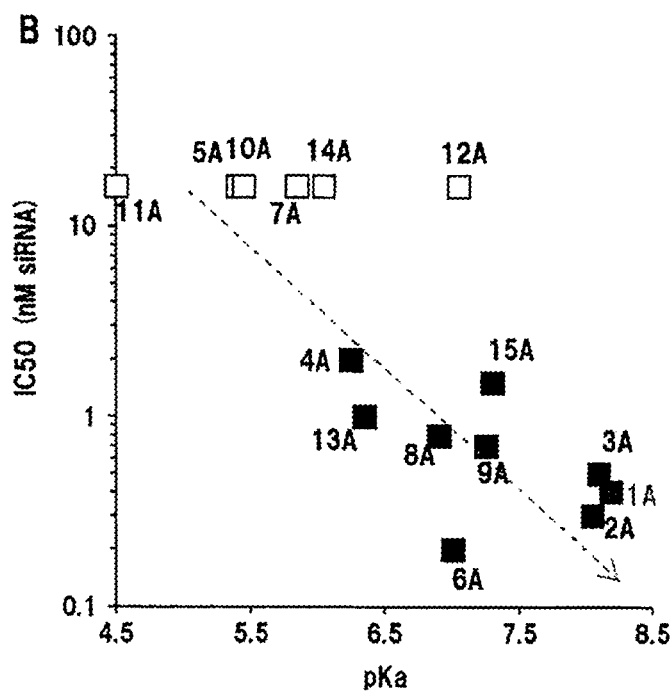
FIG. 3B is a graph showing in vitro knockdown activity of respective LNPs containing lipid compounds each having different chemical structures at hydrophilic sites in Example 2.
Figure 3C:
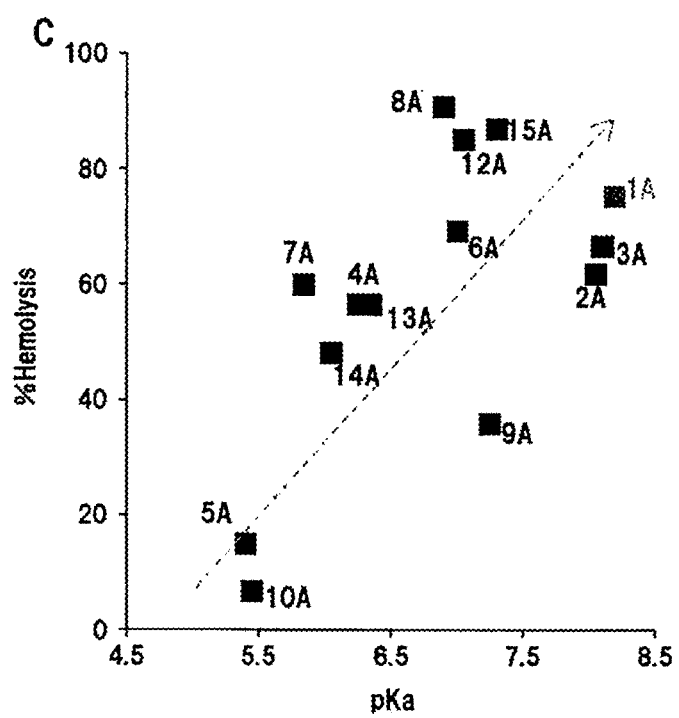
FIG. 3C is a graph showing hemolysis activity of respective LNPs containing lipid compounds each having different chemical structures at hydrophilic sites in Example 2.

The in vivo F7 knockdown activity showed bell-type pKa dependence with maximum activity of about pKa 6.4 (FIG. 3A), which was the same result as previously reported results (Non-Patent Literature 10 and Non-Patent Literature 13). Several derivatives showing better knockdown activity than that of CL1A6 (YSK12), which is a benchmark, were found. A result in which the in vitro knockdown activity increased according to an increase of pKa was obtained (FIG. 3B). The hemolysis activity was also improved according to an increase of pKa (FIG. 3C). Based on the fact that both activities showed approximately predicted pKa dependence, it was found that change in chemical structure around the tertiary amino group greatly affected a pKa of pH-sensitive cationic lipids, whereas the influence of the change in chemical structure around the tertiary amino group on other properties was relatively small. In other words, it was suggested that it is possible to adjust only a pKa to a target value by changing a chemical structure around the tertiary amino group.

Example 3

Figure 4A:
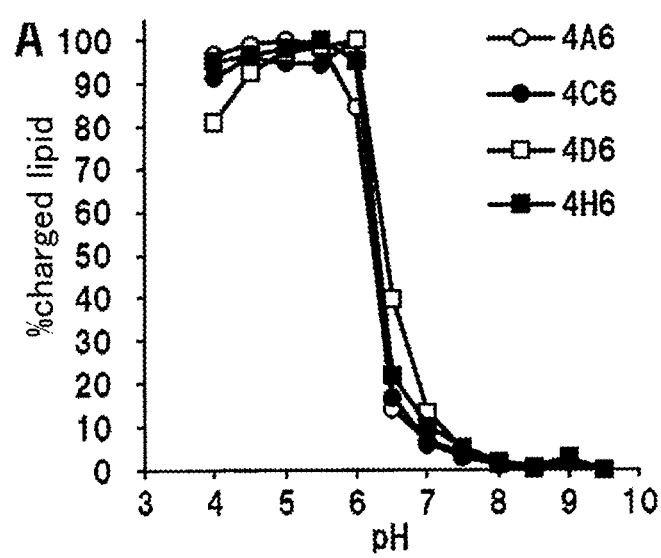
FIG. 4A is a graph showing pKa's of LNPs containing lipid compounds (CL4 series) each having different hydrophobic scaffold structures in Example 3.
Figure 4B:
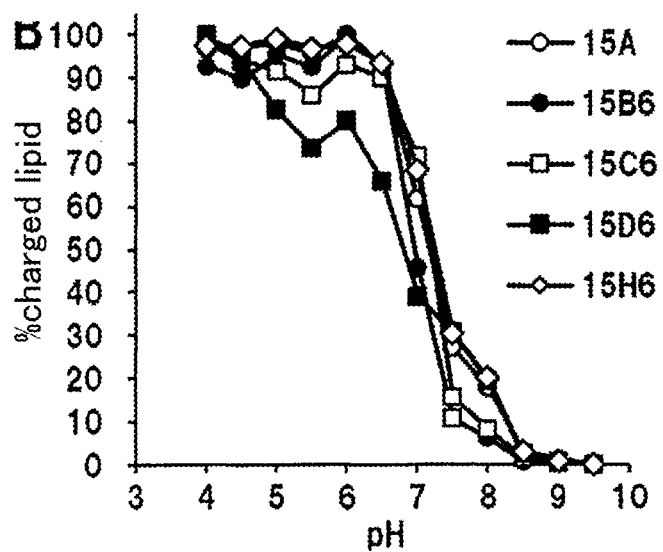
FIG. 4B is a graph showing pKa's of LNPs containing lipid compounds (CL15 series) each having different hydrophobic scaffold structures in Example 3.
Figure 5:
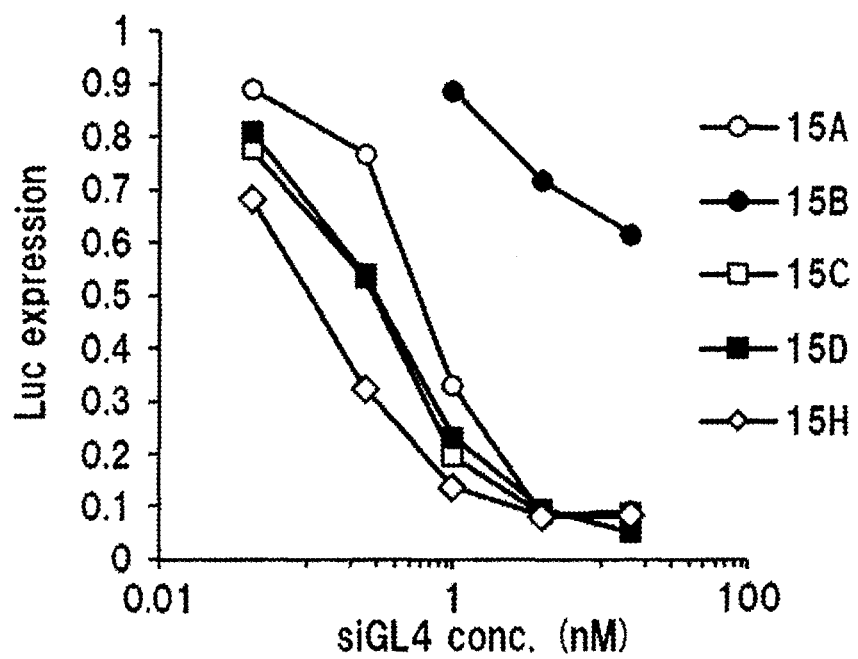
FIG. 5 is a graph showing in vitro knockdown activity of CL15-LNPs each having different hydrophobic scaffold structures in Example 3.
Figure 6A:
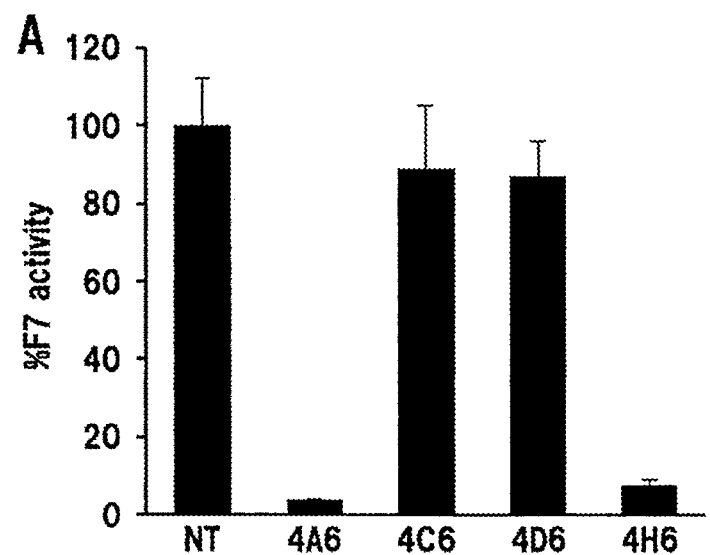
FIG. 6A is a graph showing in vivo F7 knockdown activity of LNPs containing lipid compounds (CL4 series) each having different hydrophobic scaffold structures in Example 3.
Figure 6B:
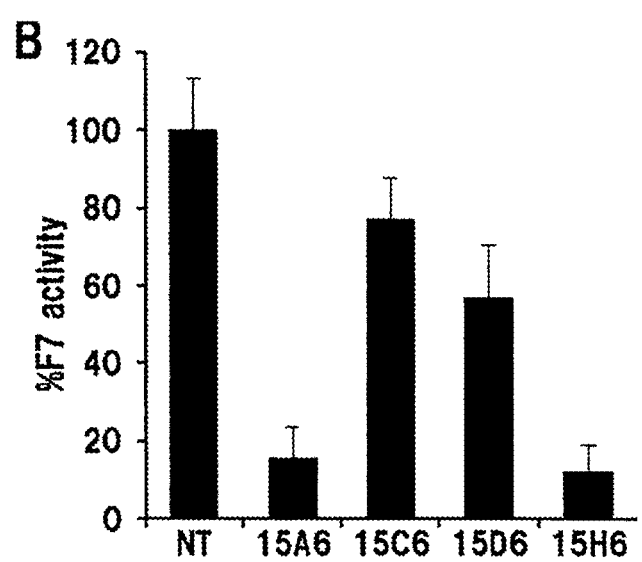
FIG. 6B is a graph showing in vivo F7 knockdown activity of LNPs containing lipid compounds (CL15 series) each having different hydrophobic scaffold structures in Example 3.

An influence of changing a chemical structure of a hydrophobic scaffold was evaluated in the same manner as in Example 2 by fixing a hydrophilic site to two kinds of compounds, which are CL4 and CL15. When a pKa was measured using TNS, it was 6.25 to 6.40 for CL4 and was 6.80 to 7.25 for CL15, which shows that they were not affected by change in hydrophobic scaffold structure (FIGS. 4A and 4B). Regarding the in vitro knockdown activity, other derivatives except CL15B had superior activity than that of CL15A having a hydrophobic scaffold of the related art (FIG. 5). In particular, CL15H, which has an oleic acid as a hydrophobic scaffold, showed about three times higher activity than that of CL15A. Regarding the in vivo F7 knockdown activity, the activity of the hydrophobic scaffolds C and D was low for both CL4 and CL15, whereas a hydrophobic scaffold H showed the same or higher activity than that of the hydrophobic scaffold A (FIGS. 6A and 6B).

Figure 7A:
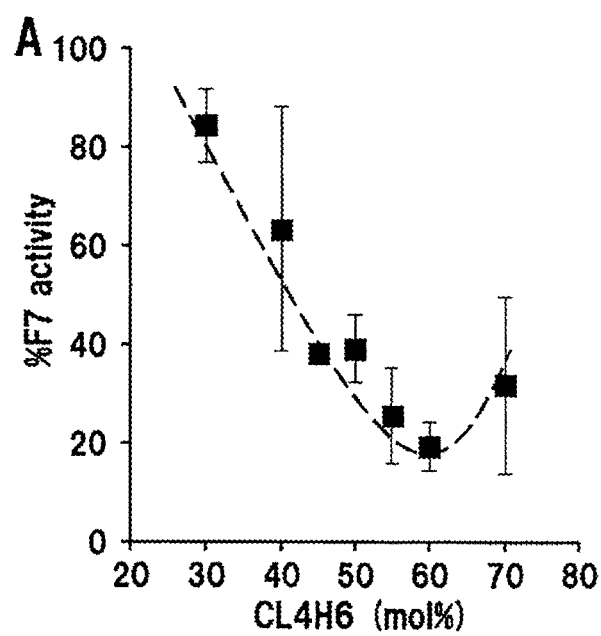
FIG. 7A is a graph showing results of optimization of a lipid composition of a pharmaceutical formulation using in vivo F7 knockdown activity of CL4H6-LNP as an index in Example 3.
Figure 7B:
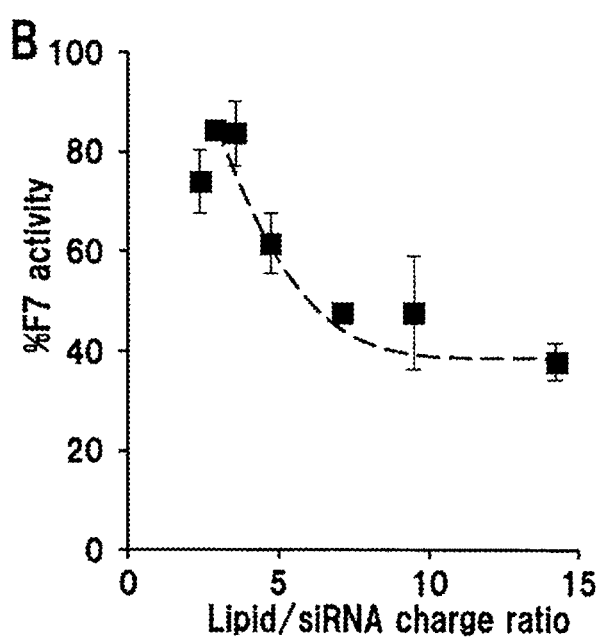
FIG. 7B is a graph showing results of optimization of a Lipid/siRNA charge ratio of a pharmaceutical formulation using in vivo F7 knockdown activity of CL4H6-LNP as an index in Example 3.
Figure 8:
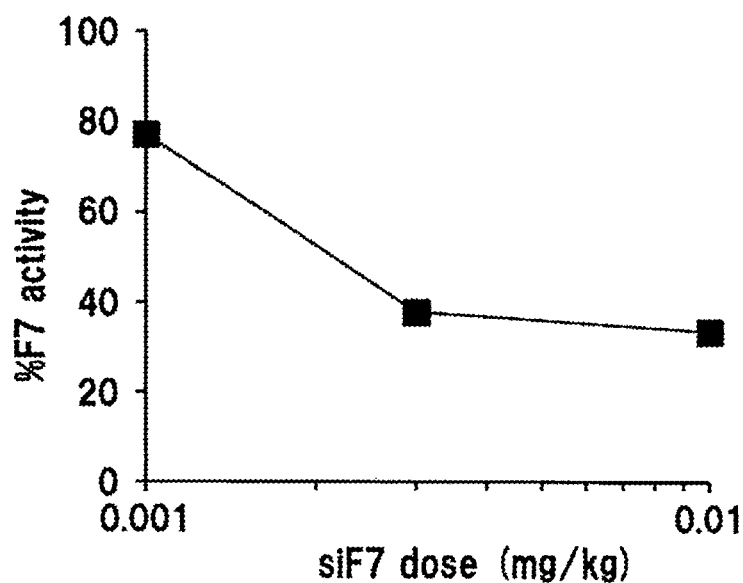
FIG. 8 is a graph showing dose dependency of in vivo F7 knockdown efficiency of CL4H6-LNP having an optimal composition in Example 3.

Regarding CL4H which showed particularly high F7 knockdown activity, pharmaceutical formulation was optimized from the viewpoint of knockdown activity while focusing on a lipid composition and a lipid/siRNA charge ratio. LNPs were prepared by changing a molar ratio of CL4H:cholesterol from 30:70 to 70:30. As a result of the experiment, the maximum activity was shown at a CH4H:cholesterol ratio of 60:40 (FIG. 7A). LNPs were prepared by changing a Lipid/siRNA charge ratio within a range of 2.375 to 14.25. As a result of the experiment, the knockdown activity increased as the charge ratio increased, and it reached a plateau at a charge ratio of about 7 (FIG. 7B). Based on this result, a charge ratio of 14.25 was determined as the optimum charge ratio. CL4H-LNPs were prepared with the optimized formulation from the above examination, and dose dependency of F7 knockdown was examined. As a result, $ED_{50}$ showed 0.002 mg siRNA/kg (FIG. 8).

Example 4

Figure 9A:
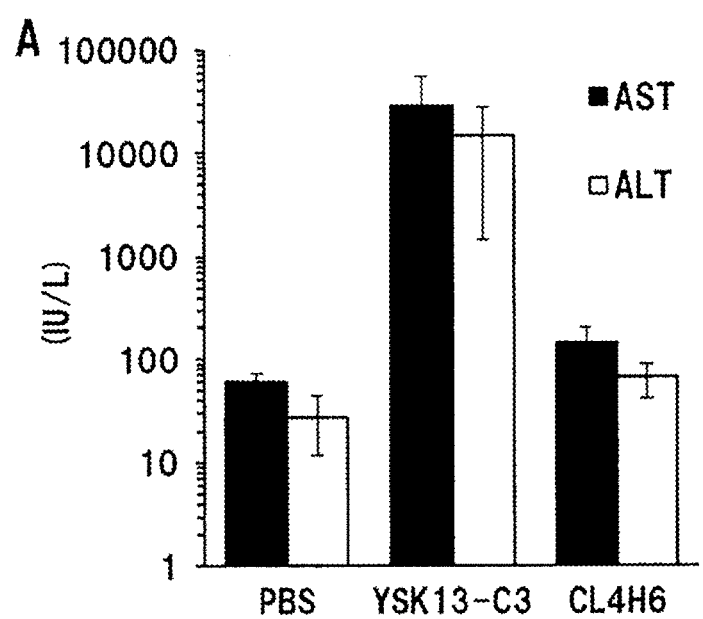
FIG. 9A is a graph showing results of evaluating safety of CL4H6-LNP in Example 4, and showing plasma ALT/AST values 24 hours after administration.
Figure 9B:
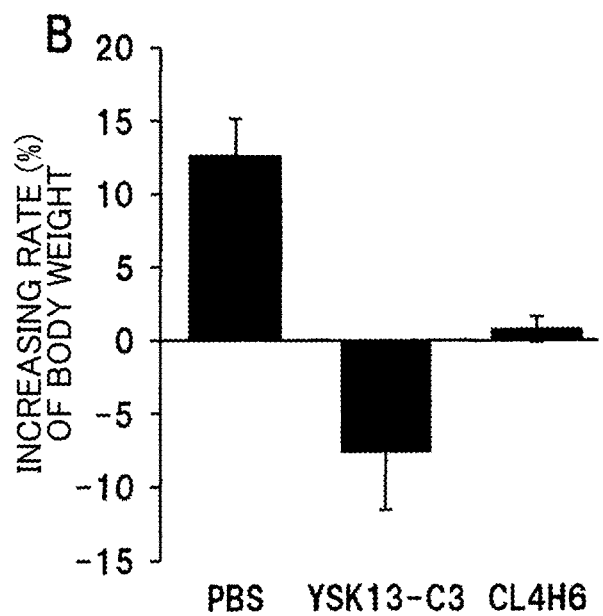
FIG. 9B is a graph showing results of evaluating safety of CL4H6-LNP in Example 4, and showing change in mouse body weight from immediately before administration to 24 hours after administration.

The safety of CL4H-LNP in vivo was examined. 7 mg siRNA/kg was intravenously administered to an ICR mouse (4 weeks old, female), and 24 hours after the administration, an alanine transaminase (ALT) value and an aspartate transaminase (AST) value in plasma, and body weight change before and after the administration were measured. As a comparative target, a pH-sensitive cationic lipid YSK13-C3 previously developed by the developer was used, and as a lipid composition, a composition of pH-sensitive lipid:cholesterol:PEG-DMG 2000=70:30:3 (molar ratio) which was optimized for YSK13-C3-LNP was used. YSK13-C3-LNP showed a strong hepatotoxicity of more than 10,000 for both ALT and AST, whereas CL4H-LNP remained to a slight hepatotoxicity level, which is the same level as that of the PBS administration group (FIG. 9A). Regarding change in body weight, the YSK13-C3-LNP administration group showed a decrease in body weight, whereas the CL4H-LNP changed to an increase in body weight (FIG. 9B). Based on the above results, it was shown that CL4H is a lipid compound having excellent safety.

Figure 10:
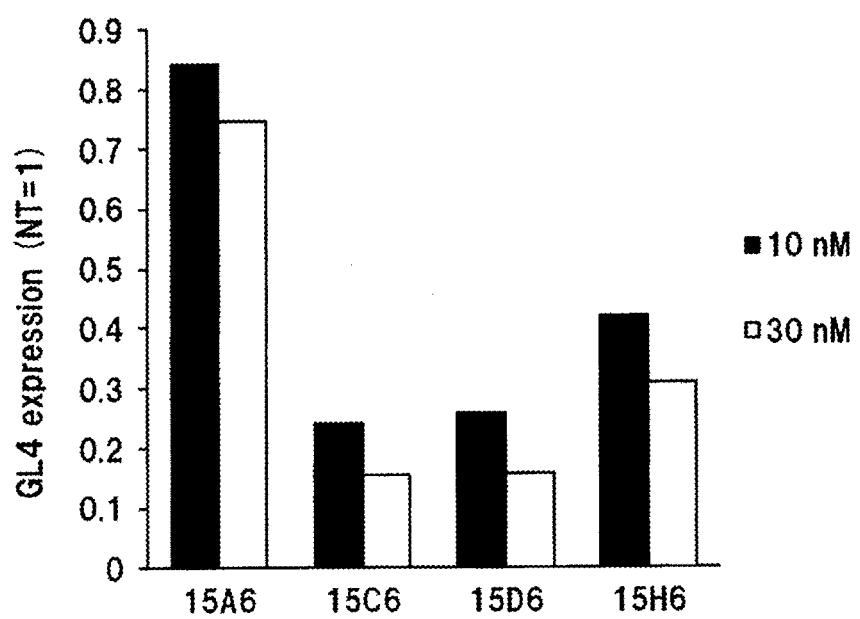
FIG. 10 is a graph showing in vitro knockdown activity of CL15-LNP of which an average particle diameter was controlled such that it was about 35 nm in Example 4.

The influence of hydrophobic scaffolds on siRNA introduction activity of small LNPs with an average particle diameter of about 35 nm was examined. A lipid composition was pH-sensitive cationic lipid:cholesterol:PEG-DMG 2000=70:30:3 (molar ratio), and LNPs loaded with siRNA against luciferase were manufactured using a microchannel with a built-in micromixer. As a result of measuring luciferase knockdown activity in HeLa-dluc cells, under conditions where CL15A having a linoleic-acid-derived hydrophobic scaffold of the related art showed knockdown efficiency of 30% or less with 30 nM siRNA, CL15C, CL15D, and CL15H all showed high knockdown efficiency of 50% or more with 10 nM siRNA (FIG. 10). This result shows that a pH-sensitive cationic lipid compound having a long hydrophobic scaffold enables overcoming of a decrease in siRNA introduction efficiency associated with the miniaturization of LNPs.

Example 5

Figure 11:
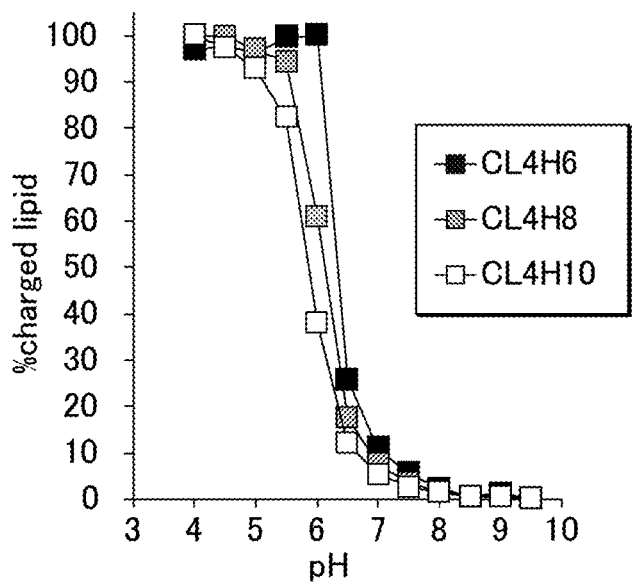
FIG. 11 is a graph showing pKa's of LNPs containing lipid compounds (CL4H series) each having different hydrophobic scaffold structures in Example 5.
Figure 12:
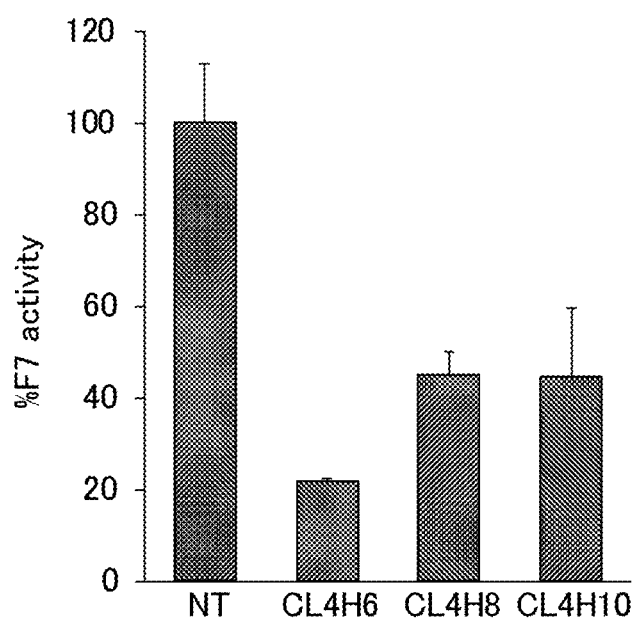
FIG. 12 is a graph showing in vivo F7 knockdown activity of LNPs containing lipid compounds (CL4H series) each having different hydrophobic scaffold structures in Example 5.

Using the three lipid compounds (CL4H6, CL4H8, and CL4H10) in which a hydrophilic site was fixed on CL4, an influence of changing a chemical structure of the above-described hydrophobic scaffold 1 was evaluated in the same manner as in Example 2. When a pKa was measured using TNS, it was 6.35 for CL4H6, was 6.10 for CL4H8, and was 5.85 for CL4H10, and a pKa decreased as a carbon chain length of the hydrophobic scaffold 1 increased (FIG. 11). Regarding the in vivo F7 knockdown activity, LNPs loaded with siRNA against F7 were intravenously administered to an ICR mouse, and F7 enzyme activity in plasma was measured 24 hours after the administration. As a result, all of the three types of derivatives had the activity. Among them, CL4H6 showed the best activity (FIG. 12).

Example 6

Figure 13A:
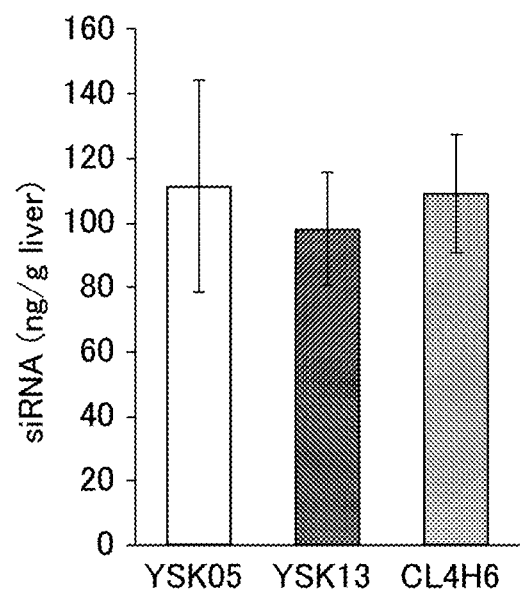
FIG. 13A is a graph showing measurement results of an amount of siRNA (ng/g liver) 30 minutes after administration in the liver of mice to which CL4H6-LNP, YSK05-LNP, and YSK13-C3-LNP which were loaded with siRNA against F7 were administered in Example 6.
Figure 13B:
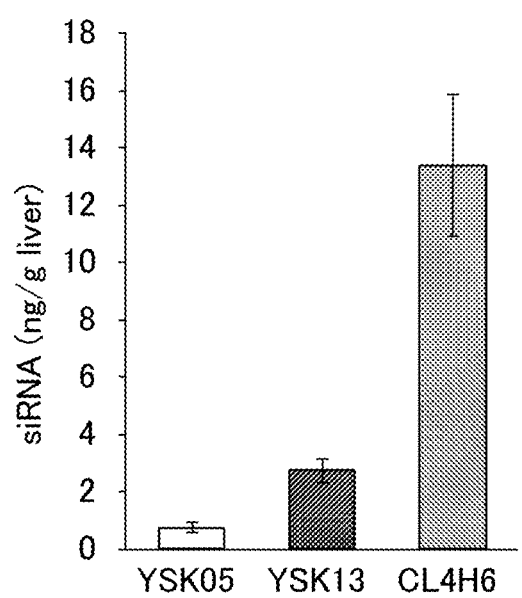
FIG. 13B is a graph showing measurement results of an amount of siRNA (ng/g liver) 24 hours after administration in the liver of mice to which CL4H6-LNP, YSK05-LNP, and YSK13-C3-LNP which were loaded with siRNA against F7 were administered in Example 6.
Figure 13C:
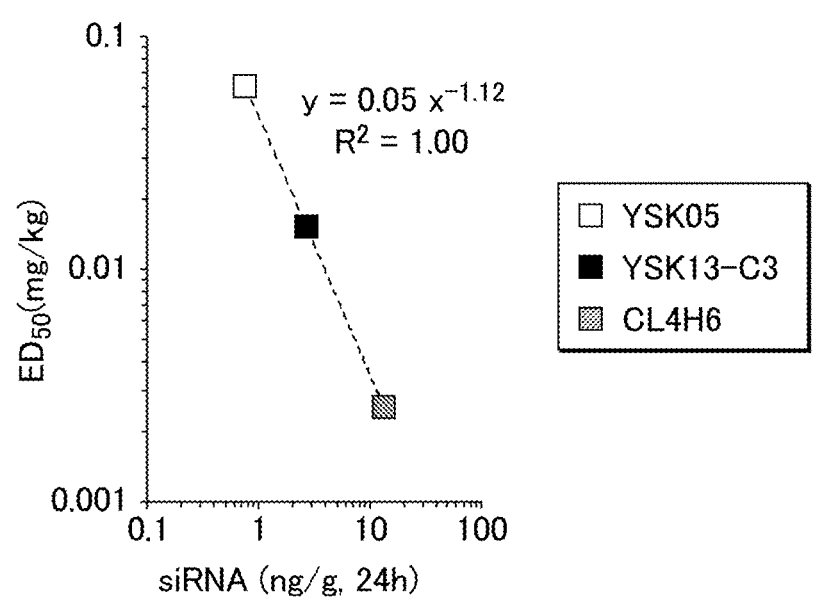
FIG. 13C is a graph plotting a relationship between $ED_{50}$ in F7 knockdown, and an amount of siRNA (ng/g liver, 24 h) in the liver 24 hours after administration to mice to which CL4H6-LNP, YSK05-LNP, and YSK13-C3-LNP which are loaded with siRNA against F7 were administered in Example 6.

The in vivo F7 knockdown activity was measured for CL4H6, and lipid compounds YSK05 and YSK13-C3 disclosed in Non-Patent Literature 11 and the like, and a relationship with a residual amount of siRNA 24 hours after the administration was examined. Regarding the in vivo F7 knockdown activity, LNPs loaded with siRNA against F7 were prepared using each lipid compound in the same manner as in Example 2, 0.01 mg siRNA/kg of each LNP was intravenously administered to ICR mice (4 weeks old, female), the liver was recovered from each mouse 30 minutes and 24 hours after the administration, and siRNA in the liver was quantitatively determined by qRT-PCR. An amount of siRNA in the liver 30 minutes after the administration was about the same as that of LNPs obtained by using any lipid compound, and therefore it was confirmed that an amount transferred to the liver was almost the same (FIG. 13A). On the other hand, a large difference was observed in a residual amount of siRNA in the liver 24 hours after the administration (FIG. 13B). A residual amount of siRNA in the liver to which CL4H6-LNP was administered was 17.3 times that in the liver to which YSK05-LNP was administered, and 4.8 times that in the liver to which YSK13-C3-LNP was administered. In addition, $ED_{50}$ in F7 knockdown of each mouse to which each LNP was administered was obtained, and this value and a residual amount of siRNA in the liver 24 hours after the administration were in inverse proportion (FIG. 13C). These results suggested that CL4H6-LNP efficiently escaped the endosome and delivered siRNA to the cytoplasm.

Figure 14:
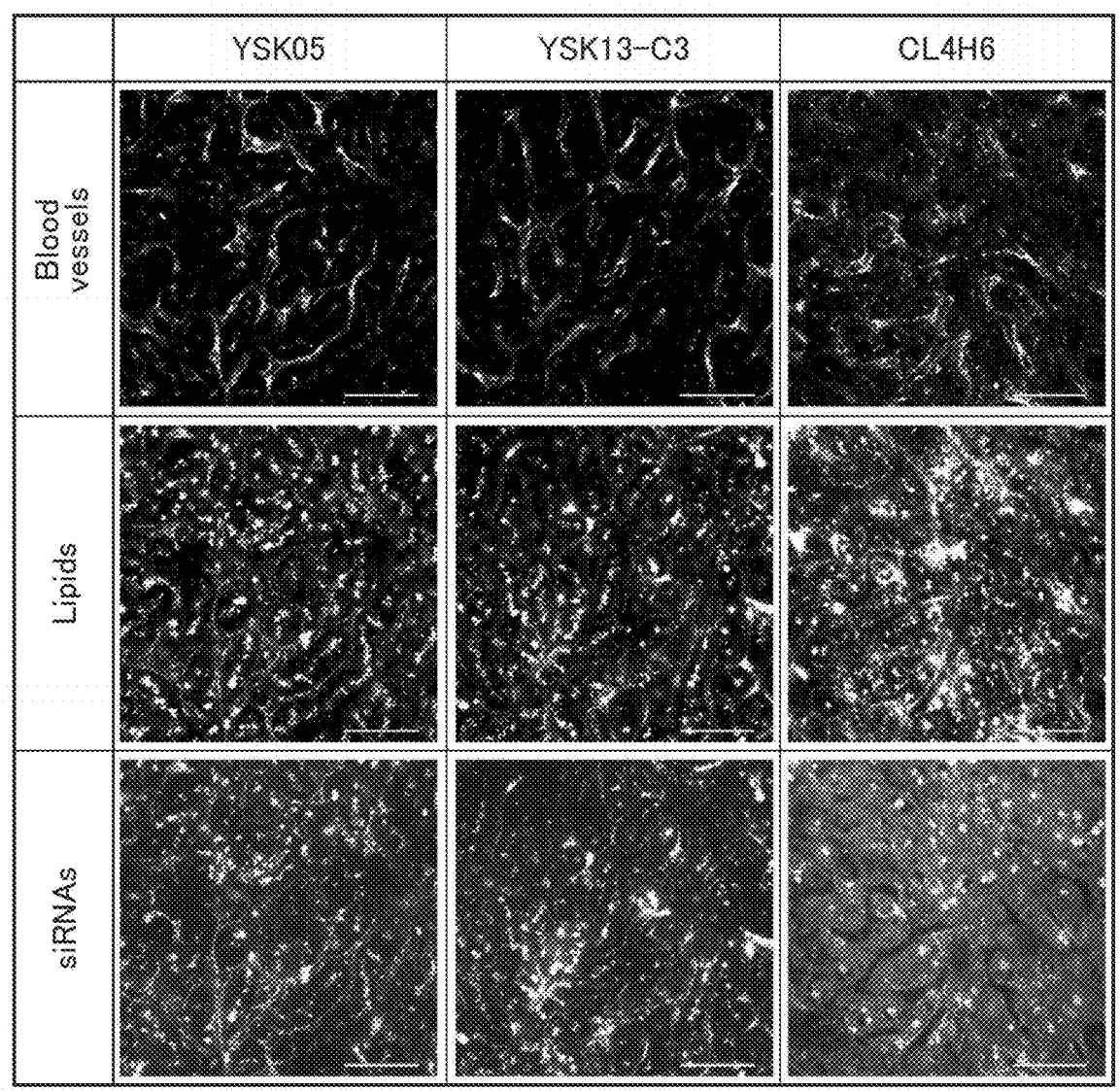
FIG. 14 shows fluorescent staining images of blood vessels (FITC), lipids (DiI), and siRNAs (Cy5) of the liver 1 hour after administration to mice to which CL4H6-LNP, YSK05-LNP, and YSK13-C3-LNP which are loaded with siRNA against F7 were administered in Example 6.

In addition, 1 mg siRNA/kg of each LNP was intravenously administered to ICR mice (4 weeks old, female), the liver of the mice 1 hour after the administration was excised, and the nucleus (Hoechst33342), blood vessels (FITC), lipids (DiI), and siRNA (Cy5) were each fluorescently stained and observed with a confocal laser microscope (CLSM). As a result, an amount of siRNA fluorescence in the cytoplasm of liver parenchymal cells was highest in the mouse to which CL4H6-LNP was administered, and it was observed that CL4H6-LNP efficiently delivered siRNA to the cytoplasm (FIG. 14).

Figure 15A:
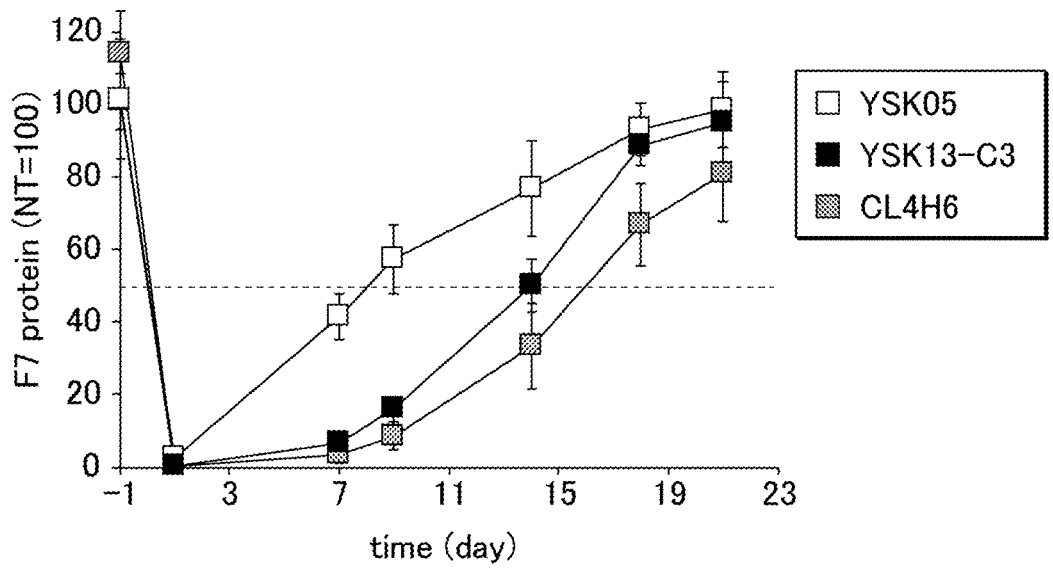
FIG. 15A is a graph showing change over time in relative amount of F7 protein in plasma (with an amount of F7 protein in plasma of non-LNP-administered mice (NT) on each recovery day being defined as 100) of mice to which CL4H6-LNP, YSK05-LNP, and YSK13-C3-LNP which are loaded with siRNA against F7 were administered in Example 6.
Figure 15B:
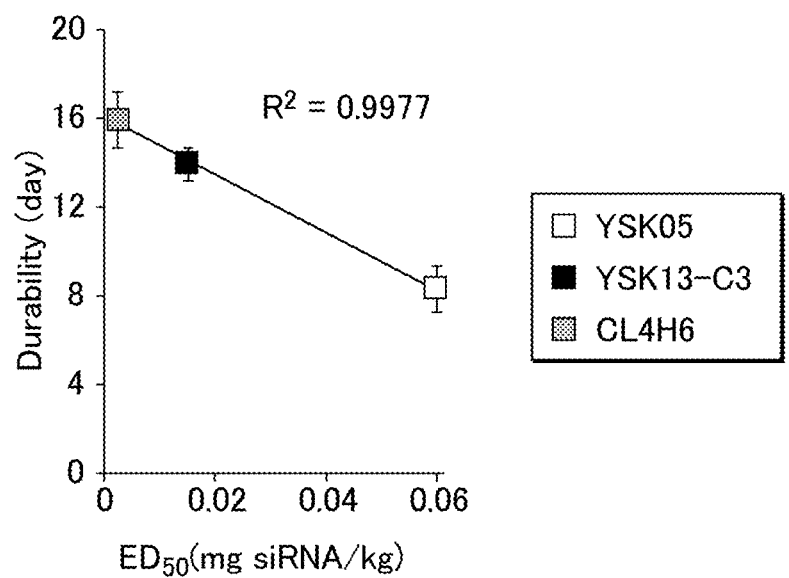
FIG. 15B is a graph plotting a relationship between $ED_{50}$ in F7 knockdown, and an elapsed time (Durability) (day) after LNP administration until a relative amount of F7 protein in plasma of mice to which CL4H6-LNP, YSK05-LNP, and YSK13-C3-LNP which are loaded with siRNA against F7 were administered became 50 in Example 6.

0.3 mg siRNA/kg of each LNP was intravenously administered to ICR mice (4 weeks old, female), and an amount of F7 protein in plasma was quantitatively determined over time. FIG. 15A shows change over time in relative amount of F7 protein in plasma (with an amount of F7 protein in plasma of non-LNP-administered mice (NT) on each recovery day being defined as 100). Mice to which CL4H6-LNP was administered were able to suppress a relative amount of F7 protein in plasma low for the longest period. In addition, when $ED_{50}$ in F7 knockdown of mice to which each LNP was administered was obtained, this value, and an elapsed time (Durability) (day) after LNP administration until a relative amount of F7 protein in plasma became 50 were in a negative correlation (FIG. 15B). That is, CL4H6-LNP maintained gene knockdown activity over a longer period than YSK05-LNP and YSK13-C3-LNP at the same siRNA dose.

An F7 protein in plasma was quantitatively determined by a color reaction using Biophen FVII assay kit (manufactured by Hypen BioMed). In this color reaction, an FVII protein was first complexed with a tissue factor (TF) in the kit. The obtained FVII-TF complex activated a factor X (FX) in the kit (FXa), and with this enzyme activity, a chromogenic substrate was produced. An amount of chromogenic substrate produced was quantitatively determined by measuring an absorbance at 405 nm.

Figure 16A:
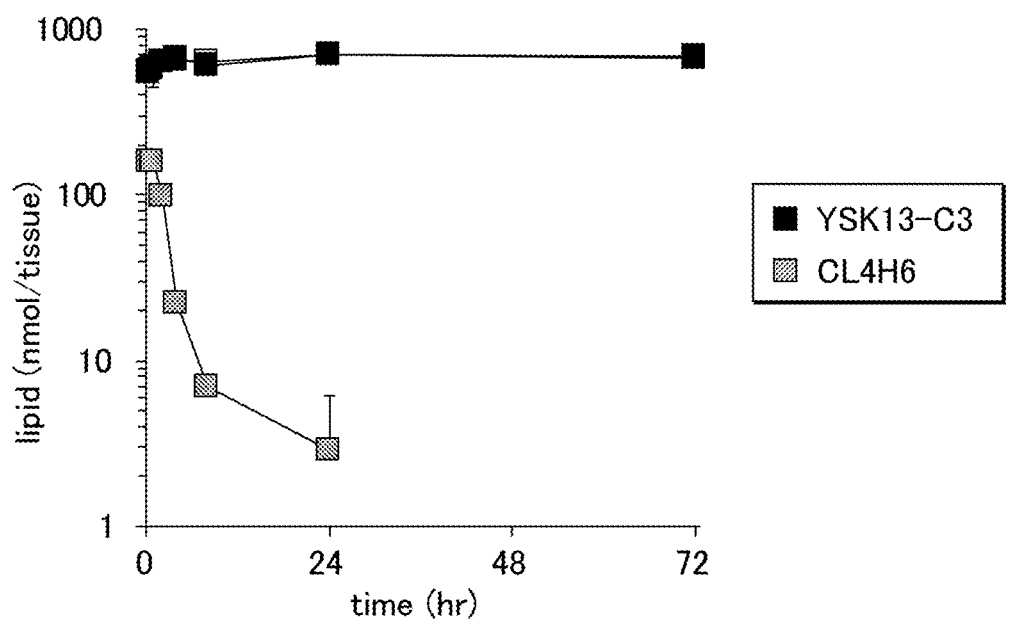
FIG. 16A is a graph showing change over time in content of respective cationic lipids in the liver of mice to which CL4H6-LNP, YSK05-LNP, and YSK13-C3-LNP which are loaded with siRNA against F7 were administered in Example 6.
Figure 16B:
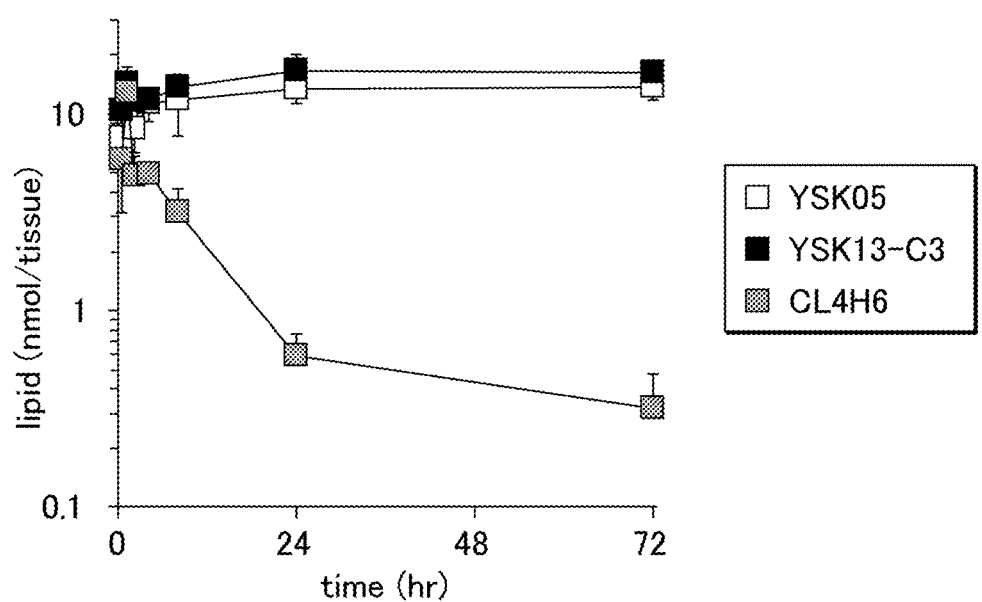
FIG. 16B is a graph showing change over time in content of respective cationic lipids in the spleen of mice to which CL4H6-LNP, YSK05-LNP, and YSK13-C3-LNP which are loaded with siRNA against F7 were administered in Example 6.

1 mg siRNA/kg of Each LNP was intravenously administered to ICR mice (4 weeks old, female), the liver and spleen were recovered over time, and each cationic lipid was quantitatively determined by LC/MS. As a result, it was confirmed that YSK05 and YSK13-C3 in the liver and spleen were almost constant until 72 hours after the administration, whereas a tissue content of CL4H6 decreased over time in both the liver and spleen (FIGS. 16A and 16B). Based on these results, it was perceived that CL4H6 has a high level of biodegradability, and thus contributes to high safety.

Example 7

By further modifying CL4H6-LNP with methoxy polyethyleneglycol 2000 distearoylglycerol (PEG-DSG 2000), a residual time in blood was prolonged, and the knockdown activity in cancer cells was further evaluated.

Figure 17:
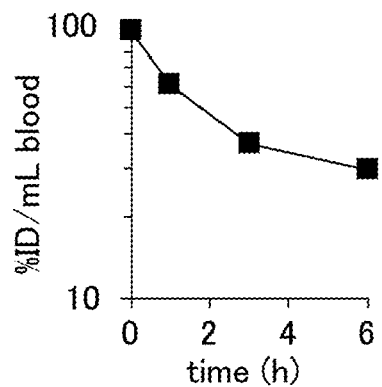
FIG. 17 is a graph showing change over time in relative amount of PEG-DSG-modified CL4H6-LNP in blood (with an amount of PEG-DSG-modified CL4H6-LNP (ID) administered to mice being defined as 100%) of mice to which PEG-DSG-modified CL4H6-LNPs were administered in Example 7.

Specifically, first, LNPs loaded with siRNA against PLK1 were prepared using CL4H6-LNP in the same manner as in Example 2. The obtained CL4H6-LNP was dispersed with PEG-DSG 2000 in a 10% EtOH aqueous solution at pH 6.0 and incubated at 60° C. for 30 minutes, and thereby CL4H6-LNP was further modified with PEG-DMG 2000. 0.5 mg siRNA/kg of this PEG-DSG-modified CL4H6-LNP was intravenously administered to ICR mice (4 weeks old, female), and an amount of PEG-DSG-modified CL4H6-LNP in blood was quantitatively determined over time. FIG. 17 shows change over time in relative amount of PEG-DSG-modified CL4H6-LNP in blood (with an amount of PEG-DSG-modified CL4H6-LNP (ID) administered to mice being defined as 100%).

Figure 18A:
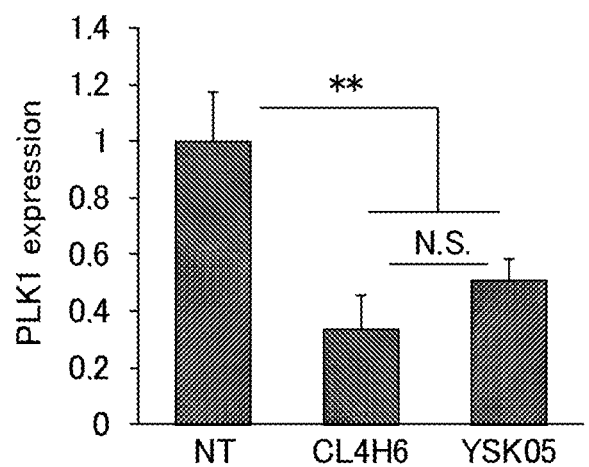
FIG. 18A is a graph showing measurement results of a relative PLK1 expression level (with a PLK1 expression level in the cancer tissue of non-siRNA-administered mice into which OSRC2 cells were subcutaneously transplanted (NT) being defined as 1) in the cancer tissue 24 hours after administration to mice into which OSRC2 cells were subcutaneously transplanted and to which PEG-DSG modified CL4H6-LNP and PEG-DSG modified YSK05-LNP which are loaded with siRNA against PLK1 were administered in Example 7.

PEG-DSG-modified YSK05-LNP was prepared in the same manner as the PEG-DSG-modified CL4H6-LNP. Next, 2 mg siRNA/kg of each LNP was intravenously administered to mice into which OSRC2 cells (derived from a human renal cell carcinoma) were subcutaneously transplanted, and an expression level of PLK1 gene in the cancer tissue 24 hours after the administration was measured by a qRT-PCR method. As a result, a relative PLK1 expression level (with a PLK1 expression level in the cancer tissue of non-LNP-administered control mice (NT) being defined as 1) was significantly lower in both mice to which PEG-DSG-modified CL4H6-LNP was administered and mice to which PEG-DSG-modified YSK05-LNP was administered. In particular, PEG-DSG-modified CL4H6-LNP had a lower relative PLK1 expression level in blood than that of PEG-DSG-modified YSK05-LNP, and showed excellent knockdown activity (FIG. 18A).

Figure 18B:
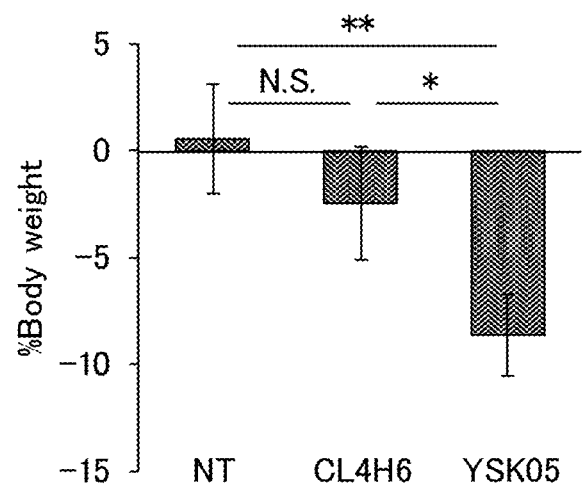
FIG. 18B is a graph showing measurement results of a rate of change (%) in body weight from before administration to 24 hours after administration to mice into which OSRC2 cells were subcutaneously transplanted and to which PEG-DSG modified CL4H6-LNP and PEG-DSG modified YSK05-LNP which are loaded with siRNA against PLK1 were administered in Example 7.

In addition, body weights of the mice into which OSRC2 cells were subcutaneously transplanted were measured 24 hours after the administration of each LNP, and a rate of change (%) in body weight before the administration was examined (FIG. 18B). In the mice to which PEG-DSG-modified YSK05-LNP was administered, a slight decrease in body weight was observed after the administration, whereas in the mice to which PEG-DSG-modified CL4H6-LNP was administered, there was almost no change in body weight as compared to the mice to which PEG-DSG-modified YSK05-LNP was administered. Based on these results, it was suggested that PEG-DSG-modified YSK05-LNP is highly safe and can be used in various applications.

Example 8

LNPs containing CL4H6 loaded with siRNA against CD45 were introduced into bone-marrow-derived macrophages, and knockdown activity of CD45 gene was measured.

First, CL4H6-LNPs loaded with siRNA against CD45 at various concentrations were prepared in the same manner as in Example 2 except that a lipid composition in which cationic lipid (CL4H6), cholesterol, and PEG-DMG 2000 are at a molar ratio of 60:40:2 was used, and siRNA against CD45 was used.

Figure 19:
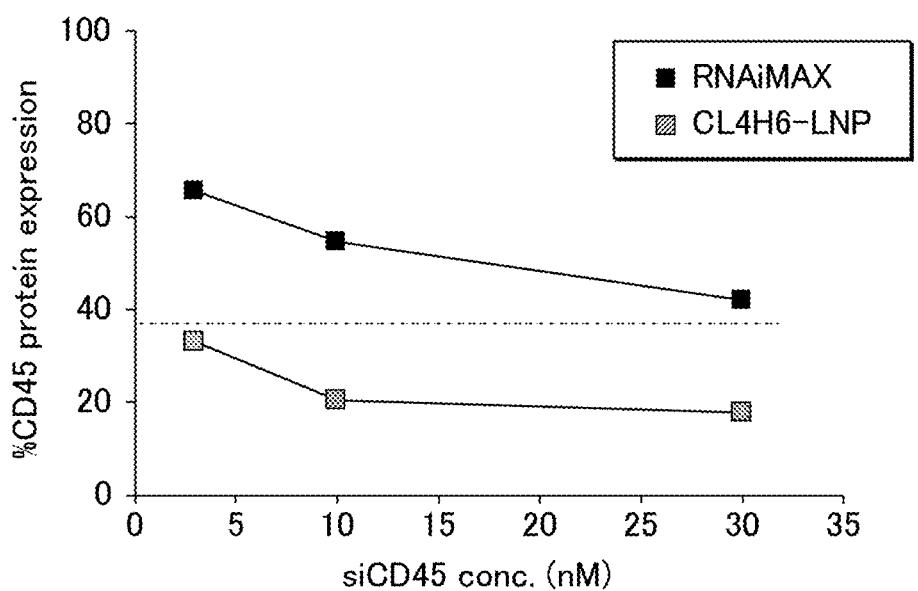
FIG. 19 is a graph showing measurement results of a relative CD45 expression level of respective macrophages 24 hours after culture (with a CD45 expression level of a tumor-associated macrophage (NT) to which siRNA was not administered being defined as 100%) which are results obtained by transfecting siRNA against CD45 into macrophages induced from ICR mouse bone marrow cells, and culturing them in Example 8.

The CL4H6-LNPs loaded with an siRNA against CD45 were added to a culture medium of macrophages derived from bone marrow cells of ICR mice, and cultured for 24 hours. As a comparative target, siRNA against CD45 was transfected into the macrophages using a Lipofectamine reagent (manufactured by Thermo Fisher Scientific), and culture was performed for 24 hours. An expression level of CD45 gene 24 hours after the culture of each macrophage was measured by a qRT-PCR method. FIG. 19 shows results of a relative CD45 expression level (%) of respective macrophages (with a CD45 expression level in a macrophage (NT) to which siRNA against CD45 was not administered being defined as 100%). Macrophages to which siRNA against CD45 loaded on CL4H6-LNP was transfected induced gene knockdown at a 10-fold higher efficiency than macrophages to which siRNA against CD45 was transfected using a Lipofectamine reagent.

Example 9

LNPs loaded with siRNA against CD45 were administered to mice into which OSRC2 cells were subcutaneously transplanted, and the knockdown activity of CD45 gene was measured.

First, LNPs loaded with siRNA against CD45 were prepared in the same manner as in Example 2 except that a lipid composition in which cationic lipid (CL4H6 or YSK05), cholesterol, and PEG-DSG 2000 are at a molar ratio of 70:30:2 was used, and siRNA against CD45 was used.

Figure 20:
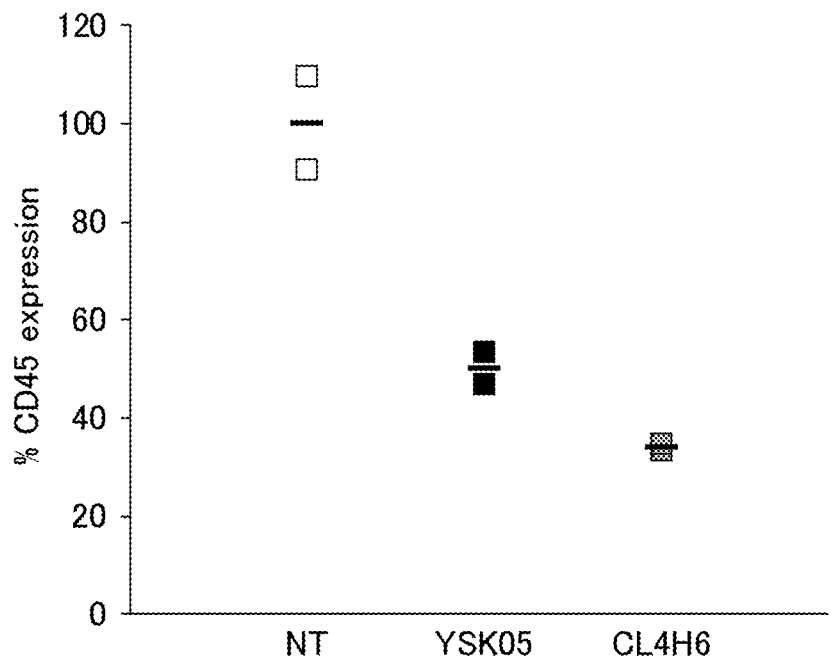
FIG. 20 is a graph showing measurement results of a relative CD45 expression level (%) of a tumor-associated macrophage (with a CD45 expression level of a tumor-associated macrophage (NT) to which siRNA against CD45 was not administered being defined as 100%) 24 hours after administration of CL4H6-LNP or YSK05-LNP which are loaded with siRNA against CD45 to mice to which OSRC2 cells were subcutaneously transplanted in Example 9.

2 mg siRNA/kg/dose of each LNP was intravenously administered to mice into which OSRC2 cells were subcutaneously transplanted for 2 consecutive days. An expression level of CD45 gene in tumor-associated macrophages 48 hours after the final administration was measured by flow cytometry. FIG. 20 shows results of a relative CD45 expression level (%) of respective tumor-associated macrophages (with a CD45 expression level in a tumor-associated macrophage (NT) to which siRNA was not administered being defined as 100%). A relative expression level of CD45 in tumor-associated macrophages was lower in the mice to which siRNA against CD45 loaded on CL4H6-LNP was administered than in the mice to which siRNA against CD45 loaded on YSK05-LNP was administered. That is, CL4H6 induced excellent gene knockdown in tumor-associated macrophages.

Example 10

LNPs containing CL4H6 were repeatedly administered to mice to evaluate safety. As siRNA loaded on LNPs, siRNA having no pharmacological activity with respect to mice was used.

First, LNPs (CL4H6-LNP) loaded with siRNA against human PLK1 were prepared in the same manner as in Example 2 using CL4H6 as a pH-sensitive cationic lipid. 0.3 mg siRNA/kg or 1 mg siRNA/kg of the obtained CL4H6-LNPs was repeatedly administered intravenously to ICR mice (4 weeks old, female) every 3 or 4 days. Specifically, CL4H6-LNPs were intravenously administered to the mice on an administration start date (day 0) and on days 4, 7, 11, 14, 18, 21, and 23 from the administration start date. 0.3 mg siRNA/kg is a dose 120 times an $ED_{50}$ (0.0025 mg siRNA/kg) of CL4H6-LNP loaded with siRNA against F7 (refer to Example 6), and 1 mg siRNA/kg is a dose 400 times the $ED_{50}$.

Figure 21:
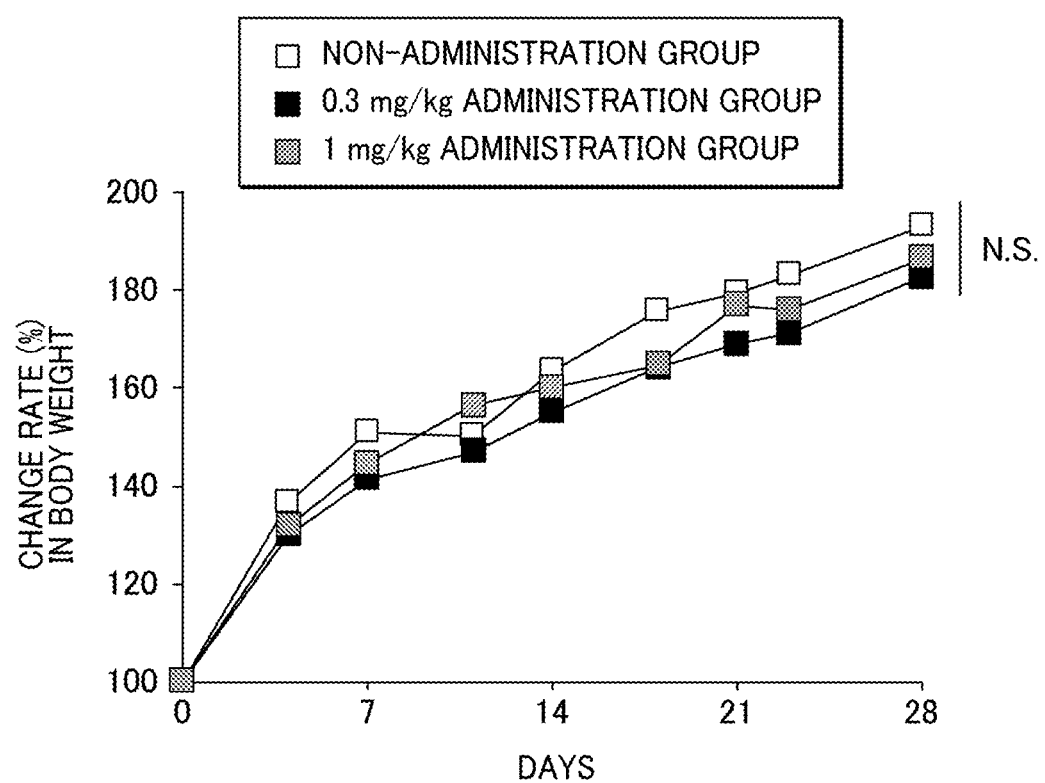
FIG. 21 is a graph showing a rate of change (%) in body weight over time (with a body weight on day 0 from start of administration being defined as 100%) of mice to which 0.3 mg siRNA/kg or 1 mg siRNA/kg of CL4H6-LNP was repeatedly administered intravenously on days 0, 4, 7, 11, 14, 18, 21, and 23 from start of administration in Example 10.

On days 0, 4, 7, 11, 14, 18, 21, 23, and 28 from the start of administration, the weight of each mouse was measured and compared with the non-administration group. FIG. 21 shows a rate of change (%) in body weight over time (with a body weight on day 0 from start of administration being defined as 100%) of the 0.3 mg siRNA/kg administration group (n=3), the 1 mg siRNA/kg administration group (n=3), and the non-administration group (n=3). Changes in body weight in the 0.3 mg siRNA/kg administration group and the 1 mg siRNA/kg administration group were almost the same as those in the non-administration group, and no systemic toxicity was recognized after repeated administration of CL4H6-LNP.

On day 28 from the start of repeated administration of CL4H6-LNP, the serum of each mouse of the 0.3 mg siRNA/kg administration group, the 1 mg siRNA/kg administration group, and the non-administration group was collected to measure hematological parameters, specifically, total protein (TP: g/dL), albumin (ALB: g/dL), urea nitrogen (BUN: mg/dL), creatinine (CRE: mg/dL), sodium (Na: mEq/L), potassium (K: mEq/L), chloride (Cl: mEq/L), calcium (Ca: mg/dL), inorganic phosphorus (IP: mg/dL), aspartate aminotransferase (AST: IU/L), alanine aminotransferase (ALT: IU/L), lactate dehydrogenase (LDH: IU/L), amylase (AMY: IU/L), g-glutamyltransferase (γ-GT: IU/L), total cholesterol (T-CHO: mg/dL), neutral fat (TG: mg/dL), high density lipoprotein-cholesterol (HDL-C: mg/dL), total bilirubin (T-BIL: mg/dL), and glucose (GLU: mg/dL). Each measurement was performed by a general method.

TABLE 1

| Measurement item | Non-administration group | 0.3 mg/kg administration group | 1 mg/kg administration group |
|---|---|---|---|
| TP (g/dl) | 5.2 ± 0.1 | 5.3 ± 0.2 | 5.1 ± 0.1 |
| ALB (g/dl) | 3.4 ± 0.1 | 3.4 ± 0.1 | 3.3 ± 0.1 |
| BUN (mg/dl) | 27.8 ± 5.4 | 30.0 ± 1.2 | 24.7 ± 2.4 |
| CRE (mg/dL) | 0.12 ± 0.03 | 0.15 ± 0.02 | 0.10 ± 0.03 |
| Na (mEq/L) | 151 ± 1 | 152 ± 1 | 152 ± 3 |
| K (mEq/L) | 5.5 ± 0.8 | 5.4 ± 0.7 | 4.5 ± 0.1 |
| Cl (mEq/L) | 111 ± 1 | 111 ± 1 | 113 ± 3 |
| Ca (mg/dl) | 9.8 ± 0.5 | 10.4 ± 0.4 | 9.4 ± 0. |

TABLE 1-continued

| Measurement item | Non-administration group | 0.3 mg/kg administration group | 1 mg/kg administration group |
|---|---|---|---|
| IP (mg/dl) | 7.9 ± 1.1 | 8.1 ± 1.3 | 7.0 ± 1.1 |
| AST (IU/L) | 80 ± 28 | 73 ± 35 | 75 ± 15 |

TABLE 2

| Measurement item | Non-administration group | 0.3 mg/kg administration group | 1 mg/kg administration group |
|---|---|---|---|
| ALT (IU/L) | 34 ± 6 | 34 ± 14 | 27 ± 1 |
| LDH (IU/L) | 195 ± 59 | 250 ± 103 | 301 ± 20 |
| AMY (IU/L) | 2850 ± 473 | 3518 ± 454 | 3294 ± 1034 |
| γ-GT (IU/L) | <3 | <3 | <3 |
| T-CHO (mg/dl) | 100 ± 7 | 80 ± 13 | 103 ± 18 |
| TG (mg/dl) | 194 ± 54 | 219 ± 27 | 224 ± 45 |
| HDL-C (mg/dl) | 60 ± 3 | 49 ± 8 | 60 ± 7 |
| T-BIL (mg/dl) | 0.06 ± 0.02 | 0.09 ± 0.02 | 0.12 ± 0.06 |
| GLU (mg/dl) | 185 ± 21 | 199 ± 5 | 184 ± 14 |

The measurement results are shown in Tables 1 and 2. In any item, there was no significant change in the 0.3 mg siRNA/kg administration group and the 1 mg siRNA/kg administration group, as compared to the non-administration group.

On day 28 from the start of repeated administration of CL4H6-LNP, the liver and spleen were recovered after collecting serum from each group of mice, and histopathological examination (a HE staining method) was performed.

TABLE 3

| | Group | | | | | | | | |
|---|---|---|---|---|---|---|---|---|---|
| | Non-administration group | | | 0.3 mg/kg administration group | | | 1 mg/kg administration group | | |
| Individual No. | 1 | 2 | 3 | 1 | 2 | 3 | 1 | 2 | 3 |
| Spleen | | | | | | | | | |
| Appearance of focus of extramedullary hematopoiesis*[1] | 2 | 2 | 3 | 2 | 3 | 2 | 5 | 2 | 5 |
| Lymph follicle atrophy | 0 | 0 | 0 | 0 | 0 | 0 | 0 | 0 | 0 |
| Necrotic focus | 0 | 0 | 0 | 0 | 0 | 0 | 0 | 0 | 0 |
| Hemorrhagic focus of red pulp | 0 | 0 | 0 | 0 | 0 | 0 | 0 | 0 | 0 |
| Liver | | | | | | | | | |
| Invasive hepatocyte void formation*[2] | 5 | 3 | 2 | 5 | 4 | 3 | 3 | 5 | 2 |
| Inflammatory cell cluster | 1 | 0 | 1 | 0 | 0 | 1 | 0 | 0 | 0 |
| Increased hepatocyte mitosis | 0 | 0 | 0 | 0 | 0 | 0 | 0 | 0 | 0 |
| Necrotic focus | 0 | 0 | 0 | 0 | 0 | 0 | 0 | 0 | 0 |
| Fibrosing | 0 | 0 | 0 | 0 | 0 | 0 | 0 | 0 | 0 |
| Hemorrhagic focus | 0 | 0 | 0 | 0 | 0 | 0 | 0 | 0 | 0 |

0: No abnormalities,
1: Very slight change,
2: Slight change,
3: Moderate change
4: Moderate to high change,
5: High change

*[1]The appearance of focus of extramedullary hematopoiesis was recognized in rodents even in the non-administration group.
*[2]The invasive hepatocyte void was formed by storage of glycogen during feeding.

The results are shown in Table 3. In the 0.3 mg siRNA/kg administration group and the 1 mg siRNA/kg administration group, no conspicuous findings were recognized compared to the non-administration group. Based on these results, it became clear that CL4H6-LNP has excellent safety.

INDUSTRIAL APPLICABILITY

The lipid compound of the present invention can provide a lipid membrane structure that can achieve excellent efficiency of delivering a delivery target substance such as siRNA while also achieving high safety, and thereby making it possible to overcome a decrease in activity when delivering siRNA or the like which is associated with a decrease in a particle diameter of LNPs. In addition, the lipid membrane structure including the lipid compound of the present invention has biodegradability, excellent endosomal escape ability, and LNP stabilization ability, and thereby it can efficiently deliver siRNA and the like into an immune cell such as a dendritic cell.

The invention claimed is:

1. A lipid compound represented by Formula (I) or a salt thereof,

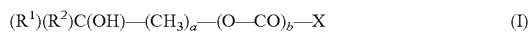  (I)

wherein in the formula, a represents an integer of 3 to 5; b represents an integer of 0 or 1; and $R^1$ and $R^2$ each independently represents a group represented by Formula (A):

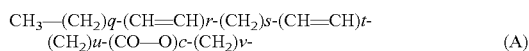  (A)

wherein in the formula, q represents an integer of 1 to 9; r represents 0 or 1; s represents an integer of 1 to 3; t represents 0 or 1; u represents an integer of 1 to 8; c represents 0 or 1; and v represents an integer of 4 to 12, where, a case in which q is an integer of 3 to 5, r and t are 1, s is 1, and u+v is an integer of 6 to 10 is excluded in a case where both b and c are 0; and X represents a 5- to 7-membered non-aromatic heterocyclic group, where the group is bonded to $(O-CO)_b$ by a carbon atom, and one or two $C_{1-4}$ alkyl groups or $C_{2-4}$ alkenyl groups may be substituted on the ring, or X represents a group represented by Formula (B):

  (B)

wherein in the formula, d represents an integer of 0 to 3, and $R^3$ and $R^4$ each independently represents a $C_{1-4}$ alkyl group or a $C_{2-4}$ alkenyl group, where the $C_{1-4}$ alkyl group or $C_{2-4}$ alkenyl group may be substituted by one or two phenyl groups, or $R^3$ and $R^4$ may be bonded to each other to form a 5- to 7-membered non-aromatic heterocycle, where one or two $C_{1-4}$ alkyl groups or $C_{2-4}$ alkenyl groups may be substituted on the heterocycle ring.

2. The lipid compound or a salt thereof according to claim 1, wherein r and t are 0, and q+s+u is an integer of 8 to 18.

3. The lipid compound or a salt thereof according to claim 1, wherein r is 1, t is 0, q is an integer of 5 to 9, and s+u is an integer of 5 to 9.

4. The lipid compound or a salt thereof according to claim 1, wherein v is an integer of 5 to 12.

5. The lipid compound or a salt thereof according to claim 1, wherein a is 4, and b is 0 or 1.

6. The lipid compound or a salt thereof according to claim 1, wherein in Formula (I), b is 0, and X is a group represented by Formula (B), in Formula (B), d is 0, $R^3$ represents a $C_{1-4}$ alkyl group which may be substituted by one phenyl group, $R^4$ represents a $C_{1-4}$ alkyl group, and $R^3$ and $R^4$ may form, by being bonded to each other, a 1-pyrrolidinyl group, a 1-piperidinyl group, a 1-morpholinyl group, or a 1-piperazinyl group, which may be substituted by one $C_{1-4}$ alkyl group.

7. The lipid compound or a salt thereof according to claim 1, wherein in Formula (I), b is 1, and X is a group represented by Formula (B), and in Formula (B), d is integer of 0 to 3, $R^3$ represents a $C_{1-4}$ alkyl group which may be substituted by one phenyl group, $R^4$ represents a $C_{1-4}$ alkyl group, and $R^3$ and $R^4$ may form, by being bonded to each other, a 1-pyrrolidinyl group, a 1-piperidinyl group, a 1-morpholinyl group, or a 1-piperazinyl group which may be substituted by one or two same or different $C_{1-4}$ alkyl groups.

8. The lipid compound or a salt thereof according to claim 1, wherein in Formula (I), b is 1, and X is a pyrrolidinyl group, a piperidinyl group, a morpholinyl group, or a piperazinyl group, which may be substituted by one or two same or different $C_{1-4}$ alkyl groups.

9. The lipid compound or a salt thereof according to claim 1, which is used as a lipid component of a lipid membrane structure for delivering siRNA into a cell.

10. A lipid membrane structure comprising the lipid compound or a salt thereof according to claim 1 as a lipid component.

11. The lipid membrane structure according to claim 10, which is a liposome.

12. The lipid membrane structure according to claim 10, wherein siRNA is sealed therein.

13. A gene knock-down method, comprising
introducing the lipid membrane structure according to claim 12, into a cell to knock down a target gene.

14. The gene knock-down method according to claim 13, wherein the cell is an immune cell or a cancer cell.

15. An immunotherapy, comprising:
separating and collecting dendritic cells from a patient,
knocking down a target gene in the dendritic cells in vitro by the gene knock-down method according to claim 13, and
administering the dendritic cells in which a target gene has been knocked down to the patient.

16. The lipid compound or a salt thereof according to claim 2, wherein r and t are 0, and q+s+u is an integer of 10 to 16.

* * * * *